United States Patent [19]

Roberts et al.

[11] Patent Number: 4,722,056
[45] Date of Patent: Jan. 26, 1988

[54] REFERENCE DISPLAY SYSTEMS FOR SUPERIMPOSING A TOMAGRAPHIC IMAGE ONTO THE FOCAL PLANE OF AN OPERATING MICROSCOPE

[75] Inventors: David W. Roberts, Hanover, N.H.; John W. Strohbehn, Norwich, Vt.; John F. Hatch, Shrewsbury, Mass.

[73] Assignee: Trustees of Dartmouth College, Hanover, N.H.

[21] Appl. No.: 830,140

[22] Filed: Feb. 18, 1986

[51] Int. Cl.$^4$ .......................................... G06F 15/42
[52] U.S. Cl. ................................................. 364/413
[58] Field of Search .............................. 364/413, 415; 128/303.1, 303 R; 350/515; 367/99

[56] References Cited

PUBLICATIONS

Glaser, E. M. et al., "The Image-Combining Computer Microscope-An Interactive Instrument for Morphometry of the Nervous System", *Journal of Neuroscience Methods*, vol. 8, No. 1, 1983, 17–32.

Primary Examiner—Jerry Smith
Assistant Examiner—Clark A. Jablon
Attorney, Agent, or Firm—Robert Shaw

[57] ABSTRACT

A reference display system that receives information from an imaging system (e.g., a CT scanner or the like), that extracts or derives three-dimensional anatomical and/or pathological information about a part of a body (e.g., the brain or other organ) of a patient. The information is digitized in the imaging system and is introduced to a computer that is programmed to reformat the digitized information to provide as output electric signal representative of the digitized information. An optical display system (e.g., a cathode ray tube, CRT, and related circuitry) is connected to receive the output of the computer and is operable to present the reformatted information at a determined plane during an operative procedure. An operating microscope is freely located in the operative location relative to the patient during the operative procedure, the focal plane of the microscope establishing the determined plane. A way is provided to establish the spatial relationship among the imaging system, the patient, and the focal plane of the microscope; and a mechanism is provided to project the reformatted imaging system information into the optics and onto the focal plane of the operating microscope during the operative procedure, the reformatted image being displayed as an overlay upon the optical image of the body part on which the operation is being performed.

33 Claims, 17 Drawing Figures

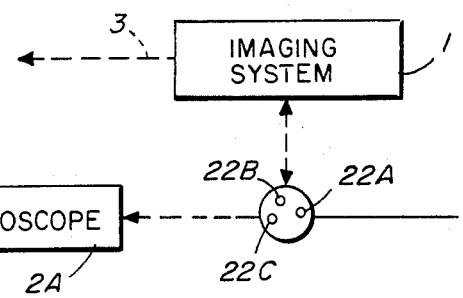
FIG. IC
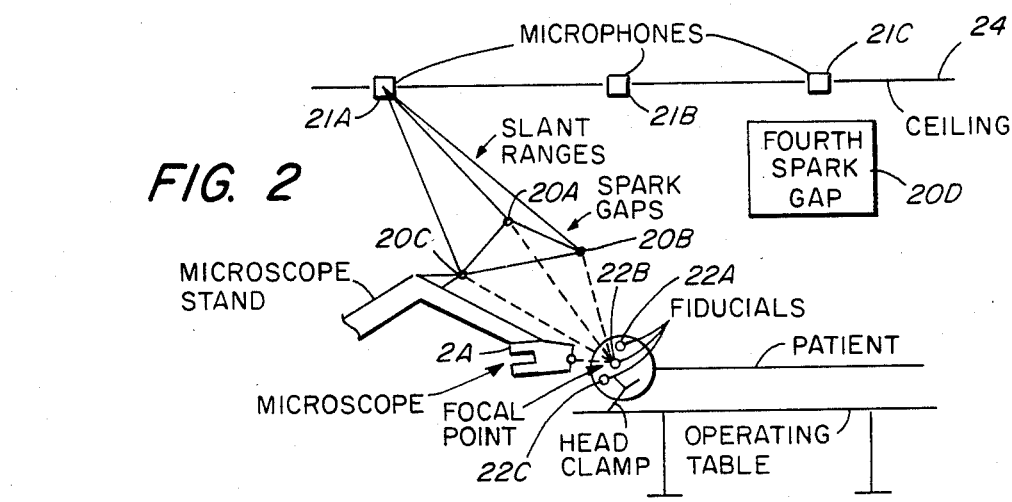
FIG. 2
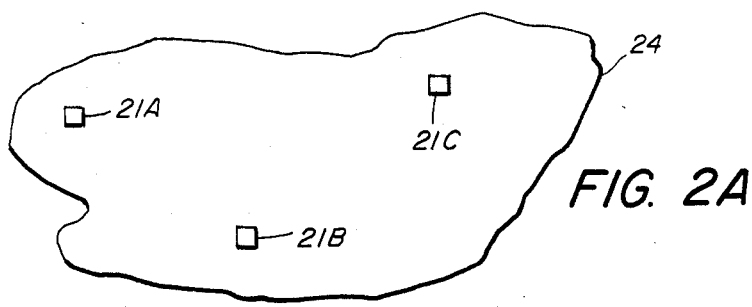
FIG. 2A
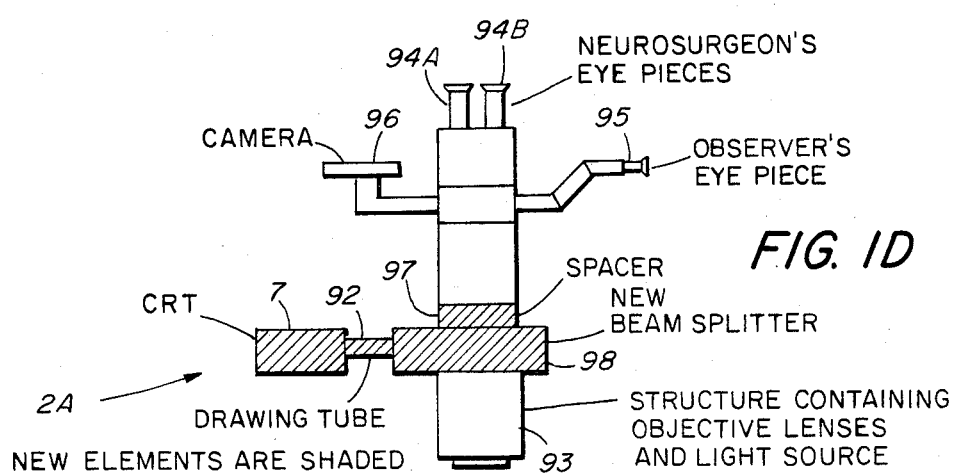
FIG. ID

REFERENCE DISPLAY SYSTEMS FOR SUPERIMPOSING A TOMAGRAPHIC IMAGE ONTO THE FOCAL PLANE OF AN OPERATING MICROSCOPE

The present invention relates to reference display systems that may be used to integrate information from three-dimensional imaging devices and an operating microscope during an operative procedure on a patient.

Annexed hereto are appendices containing detailed software to perform the mathematical calculations referred to later herein; the software is incorporated herein to reduce unnecessary details in the explanation that follows.

Although the present system is useful in other operating contexts, it is discussed herein mostly in the context of neurosurgery, e.g., a craniotomy.

Three technologies—computer tomographic imaging, stereotaxy, and microsurgery—have rapidly evolved as important tools in clinical neurosurgery. Advances in imaging techniques (CT, PET, MRI . . . ) now provide three-dimensional information about anatomic and pathologic structures previously not realized. Stereotaxy, through use of a three-dimensional coordinate system and a mechanical frame, now allows the delivery of a probe to an intracranial target with great accuracy. The operating microscope provides the magnification and illumination to enable surgeons to work with significantly greater precision and safety. The present invention integrates CT and computer technology with stereotactic principles and the operating microscope to develop a computer-based optical system for use during microneurosurgical procedures. This technique has the capability to incorporate the available computer technology with the operating room environment and many neurosurgical procedures.

At present, a neurosurgeon's ability to perform intracranial procedures for tumor, vascular disease or functional disorder is dependent upon his mental integration of the visualized operative field with his knowledge of neuroanatomy and the available radiologic studies such as CT scans. Available technology of the type herein disclosed greatly improves that mental process and achieves a far superior degree of operative precision and safety.

Conventional CT scans are oriented transversely to the body axis and as the operative approach is rarely along the axis of conventional scanning, the ability to reconstruct a CT scan to match the surgical perspective is highly appealing. A major objective of the present invention is to provide a system that will superpose reconstructed CT images over the field of view of the operating microscope. The neurosurgeon will then see, for example, the outline of a tumor (reconstructed by a computer) superposed on the operative field.

There are a number of advantages of this reconstruction/projection system:

1. There need be no dependence on the surgeon's mental reorientation of CT scanner information;

2. The information can be displayed such that it will not interfere with the neurosurgeon's procedure or require the reading of x-rays off a light screen some distance away;

3. A computer-based anatomical atlas can be developed that will superpose on the operative field important, but otherwise unseen, structures such as normal neuronal pathways and nuclei and major vascular structures; and 4. The neurosurgeon can use the superposed image as a map accurately guiding operative procedures with greater precision than presently possible.

CT scanning and reconstruction have become an integral and important part of modern medicine; the procedure used involves primarily image processing software and computer graphics. Adaptation of stereotactic technique to CT technology has been approached in a number of ways. One useful technique developed by others utilizes an adapted metal frame fixed to the patient's head at the time of scanning. Stereotactic coordinates, relating the target position of CT-demonstrated pathology to the stereotactic instrument, are generated directly from the scans and the patient is then transported to the operating room. Other developed techniques are adequate but often more cumbersome. All of these enable stereotactic procedures generally characterized by "blind" insertion of needle-like instruments through small openings utilizing previously obtained CT-determined landmarks. This has been a vital development and a foundation for the present invention. Earlier developments have not generally been amenable to "open" procedures such as craniotomy for tumor or vascular disease and, as previously noted, do not allow access to CT data after selection of a target. The CT information utilized is limited to the coordinates of a point. All instruments select a target and set the instrument accordingly; the present invention, operating in reverse, allows free positioning of the microscope with subsequent stereotactic positioning of the CT data.

The operating microscope has been incorporated into CT stereotactic work described in two formal articles: "A Stereotactic Approach to Deep-Seated Central Nervous System Neoplasms Using the Carbon Dioxide Laser" (*Surg-Neurol,* 15: 331-334, 1981, Kelly et al.); and "A Microstereotactic Approach to Deep-Seated Arteriovenous Malformations," (*Surg-Neurol,* 17: 260-262, 1982, Kelly et al.). The Kelly et al. development has also employed surgical laser instrumentation and shows the feasibility of achieving a synthesis of technologies and the prospects of refining neurosurgical operative techniques. Their technique of linking the operating microscope and the stereotactic reference system requires utilization of a large stereotactic frame and does not employ a projection system. It is a further objective of the present invention to eliminate the encumbrance of such a frame and in doing so permit a potentially widespread applicability to general neurosurgery.

Another objective of the present invention is to provide a system that will superpose appropriately reformatted, three-dimensional imaging information on the surgical field as visualized through the operating microscope.

A still further objective is to provide the capability to present information of structure lying directly below the focal plane of the microscope so the surgeon can find the location on the surface directly above the region of interest.

Another objective is to present to the surgeon accurate information on the boundary between different tissues so the surgeon can locate such boundaries accurately; for example, the surgeon may be debulking a tumor and wish to know where the edge of the tumor is relative to normal brain tissue.

An additional objective is to overlay on the visual field of the microscope, generic information from an atlas of information about functional purposes of different regions of the brain.

These and still further objectives are addressed hereinafter.

The foregoing objectives are attained generally in a reference display system (and method) for integrating information from a three-dimensional imaging device and an operating microscope during an operative procedure on a patient, that includes: an imaging system (e.g., CT, MRI, PET, or ultrasound scanners) that contains three-dimensional anatomical and/or pathological information about a part of the body (e.g., the brain or other organs) of the patient; means to digitize the information; a computer connected to receive the digitized information (e.g., stored on tape, direct transmission, or other ways), the computer being programmed to reformat the stored information to present the same at a determinable plane; an operating microscope positioned in the operative location relative to the patient, the focal plane of the microscope establishing said determinable plane; means for determining the spatial relationships of the imaging system, the patient, and the focal plane of the microscope with respect to one another; and means to project the reformatted imaging system information into the optics of the operating microscope.

The invention is hereafter described with reference to the accompanying drawing in which:

FIG. 1C shows diagrammatically a few of the units shown in FIG. 1;

FIG. 1D is a diagrammatic view, partly cutaway, of a commercially available operating microscope to which has been added a beam splitter and other optical elements needed to practice the present invention;

FIG. 2 shows schematically a portion of the system of FIG. 1 wherein the reference system in FIG. 1 employs acoustic transducers, including three microphones, and three spark gaps;

FIG. 2A shows the three microphones in FIG. 2 disposed in a nonlinear configuration (i.e., at the apices of a triangle);

Figure 6A:
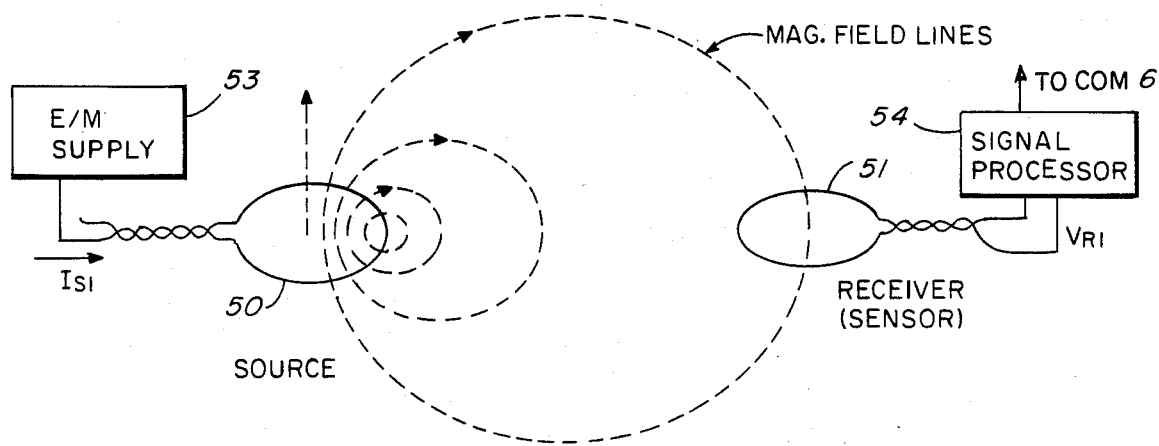
Figure 6B:
Figure 6C:
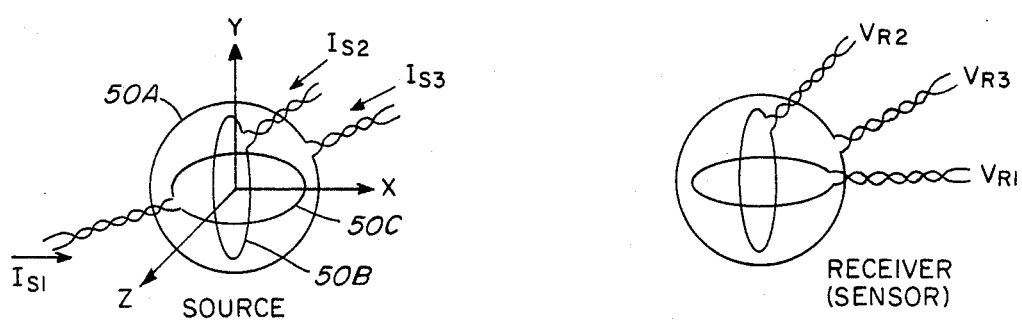

FIGS. 6A, 6B, and 6C show schematically an electromagnetic system (e.g., in the low frequency region of the electromagnetic spectrum) to replace or augment the acoustic system in FIG. 2; and FIGS. 7A, 7B, 7C, and 7D are vector diagrams of several coordinate systems which must be interrelated to register the various images in accordance with the present teachings.

Figure 1:
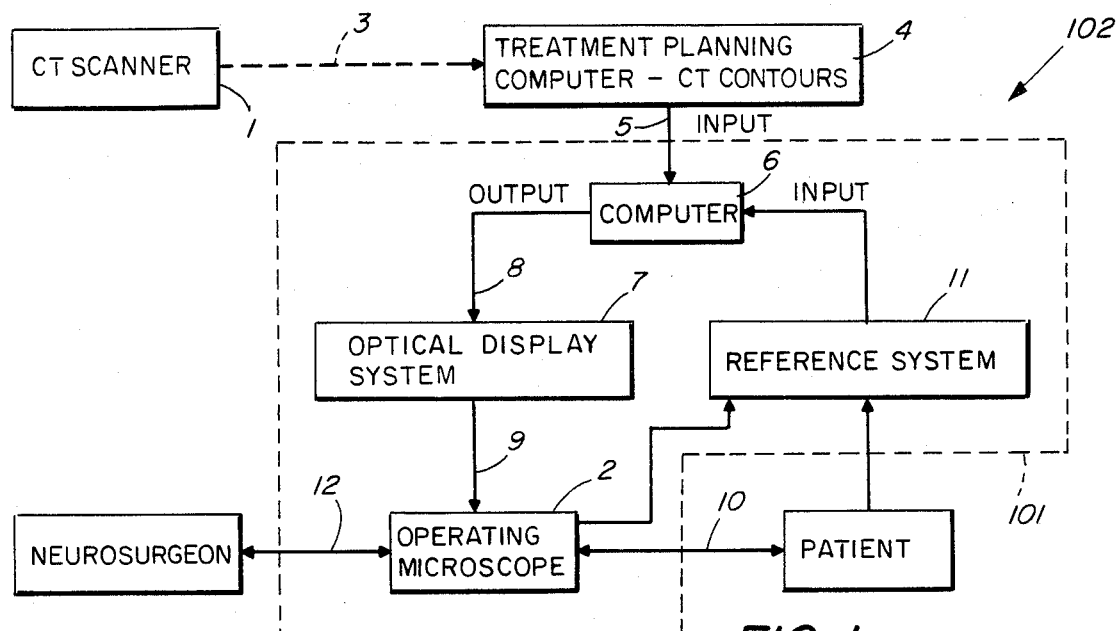
FIG. 1 is a block diagram of a system embodying the present inventive concepts, and including a reference system and an operating microscope.

In FIG. 1 the label 102 designates the important aspects of an operating room scene. It includes, in addition to a patient and a neurosurgeon, a reference display system of the present invention shown to include the block diagram elements within the broken line enclosure labeled 101. The reference display system 101 receives information from a three-dimensional imaging device 1 (e.g., a CT, an MRI, or a PET scanner or an ultrasonic imaging device) and it includes an operating microscope 2. The function of the system 101 is to extract information concerning a region of the brain of the patient by a CT scan, for example, and to present that information in the form of an image at the focal plane (labeled 99 in FIG. 1A) of the microscope 2 during an operation, at the same time as the same region of the brain is displayed as an optical image at the focal plane 99. In this way the surgeon can view simultaneously the actual brain region as well as a reconstruction of the brain region which highlights a problem area such as a tumor which is to be removed. (The CT scanner 1 and the treatment planning computer 4 actually used by the inventors are commercially available systems.)

To simplify this explanation, the three-dimensional imaging device 1 will be considered to be images from a a CT scanner. The interacting elements in the system 101 serve to integrate three-dimensional anatomical and/or pathological information derived from the brain, or other organ or body part, by the scanner 1 with the surgical field as visualized through the microscope 2 to present a composite view at the focal plane 99 to the surgeon. The scanner 1 provides image information that is stored, e.g., on x-ray film or digital tape or by a first computer 4. If not in digital form, the information is digitized and the digitized information is connected as input at 3 to the first computer 4 that acts as a treatment planning computer that provides an output 5 that is transferred to a second computer 6. (The computers 4 and 6 can, in fact, be the same or different computers.) The scanner 1 can provide real time data to the computer 4, but, typically, the information is stored on magnetic tape and, later, it is introduced to the computer 4 for processing. The computer 6 takes the information from the computer 4 and information from reference system 11 that identifies the microscope focal plane in the digitized information from the computer 4. The computer 6 is programmed to reformat the digitized information and to provide an output signal at 8 representing the reformatted information. The information at 8 eventually is fed to an optical display system 7 (i.e., a cathode ray tube or CRT) which forms an image that is displayed at a determined plane (which is at the focal plane 99 in FIG. 1A) of the microscope 2, as now explained.

Figure 1A:
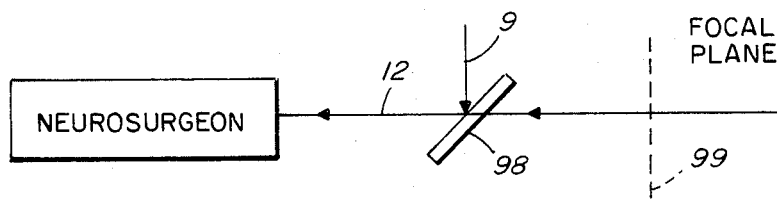
FIG. 1A shows schematically some of the optics of the operating microscope including a beam splitter.

Assuring that the image of the brain region generated by the computer 6 and displayed by CRT 7 registers with the image of the same brain region at the focal plane 99 in FIG. 1A is a nontrivial problem and is a most important aspect of the present invention, as discussed later, but first there follows an explanation of the mechanism used to present the reformatted information as an image at the focal plane 99. Whereas the signals at 3, 5, and 8 are electrical signals (i.e., either analog or binary), the signal output at 9 of the CRT 7 is an optical signal which conveys the reformatted information as an image to the microscope 2 which receives another image at 10 from the patient. The neurosurgeon can see both images since they are superposed upon one another.

Figure 1B:
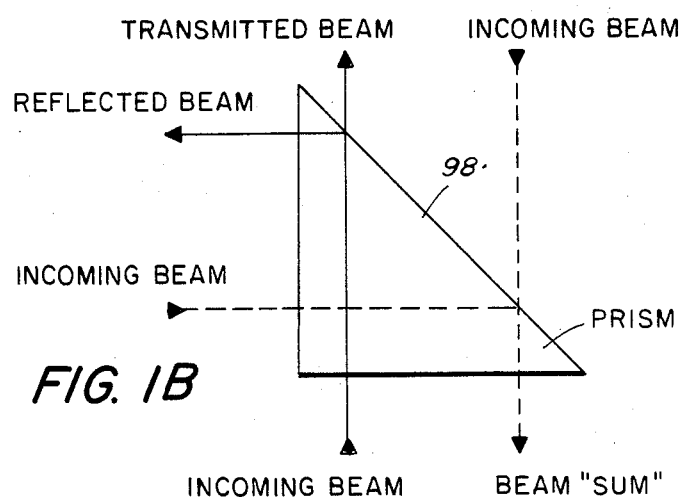
FIG. 1B shows the beam splitter of FIG. 1A diagrammatically.

The superposed views that radiate to the neurosurgeon at 12 in FIGS. 1 and 1A are achieved by using a beam splitter 98 in FIG. 1A, which is within and is part of the microscope 2 and is introduced into the optical path of the microscope. The beam splitter 98 may be a prism (see FIG. 1B) or other beam-splitting device that is used to superpose or add the two images. A few properties of the beam splitter used are important. It must have a reflection-transmission coefficient ratio such that the superposed images are not washed out or faded by the illuminated operative field. The beam-splitting optics must not introduce any visually disturbing glare or aberration. The additional optical path length ideally should be less than five centimeters to maintain an acceptable surgeon eye-to-hand distance. There are also weight and physical size constraints.

The computer-generated image, then, is displayed on the display or video screen of the CRT and provides one image that the surgeon sees. The display screen must be bright enough to provide an acceptable superposed image on the image from the illuminated operative field. The CRT also has size constraints since it, too, is mounted on the microscope 2.

The operating microscope used in experimental work was an OPMI-1H (marketed by Carl Zeiss, Inc., One Zeiss Drive, Thornwood, N.Y. 10594). The beam splitter was #474622 of the same company. The CRT used was model #vf-1900, marketed by J.V.C. Corporation of Maspeth, N.Y.

The beam splitter-CRT assembly must be attached to the standard operating room microscope so that the beam splitter is in the optical path of the microscope. In the present configuration the beam splitter-CRT assembly, consisting of the CRT 7 and the beam splitter 98 in FIG. 1D, is inserted between the beam-splitter mount used for attaching cameras (e.g., a camera 96) and holding the observer's eyepieces labeled 94A and 94B and the structure shown at 93 in FIG. 1D containing the objective lens and light source. The function of the beam splitter 98 has already been described. A spacer 97 is inserted to provide a proper mechanical fit and to permit proper operation of the focusing knob on the microscope. The CRT 7, whose function has been described, is attached to the beam splitter 98 through the drawing tube 92. The drawing tube 92 contains two lenses that can be adjusted to ensure the proper scale and focus of the CRT image in the surgeon's eyepieces 94A and 94B. It will be observed from the above explanation and FIG. 1D that the cutaway portion (i.e., the cross-hatched portion) of the figure contains the elements added to the commercially available microscope.

It will be appreciated, on the basis of the foregoing explanation, that the computer-generated image of the brain region of the patient can be precisely located at the focal plane of the microscope because the CRT and the beam splitter are rigidly attached to the microscope. It remains, therefore, to bring the optical image of that same brain region to the focal plane to effect registration of the images. This requires precise knowledge as to the spatial location of the microscope and of the patient relative to the microscope, as explained below, but first there is a brief explanation with reference to FIG. 3 of how the microscope is manipulated, it being preliminarily noted that such systems are well-known in the art to which the present invention pertains.

Figure 3:
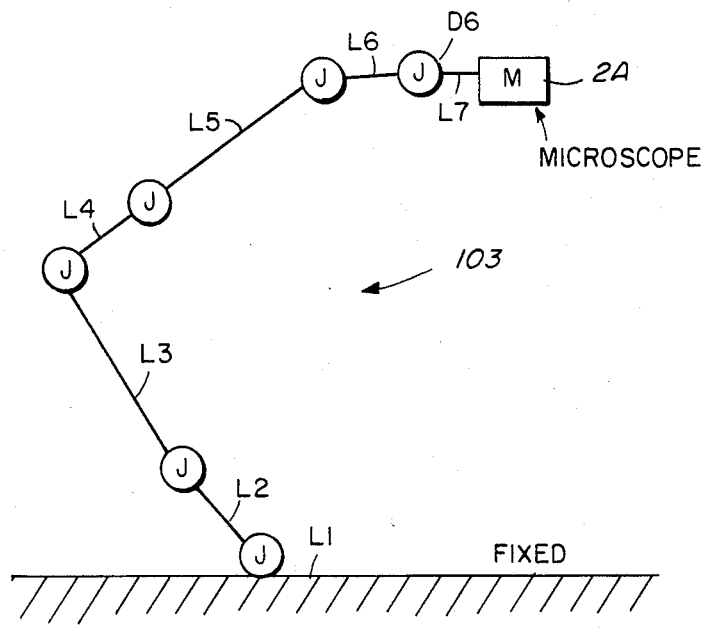
FIG. 3 is a schematic representation of an articulated structure to position the microscope of FIG. 1.

Movement of the microscope marked 2A in FIG. 3 is effected by a six-degree of freedom, articulated structure 103 consisting of arms L1–L7 with joints J therebetween. The articulated structure 103 permits movement of the microscope 2A to a desired location for performing the operative procedure.

As is indicated above, the articulated structure 103 is a commercially available structure; the microscope 2A is the microscope 2 of FIG. 1 with the optical display system 7 (FIG. 1) and other attachments incorporated therein, as shown in FIG. 1D and elsewhere. The remainder of this specification is directed mostly to a scheme for registering a computer-generated image with the image derived from the same part of the brain (or other body part) and viewed in the microscope, the aim being to present to the surgeon a computer-generated or reformatted image (from a CT scan or other imaging system) superposed (in proper orientation and scale) upon the direct optical image from the brain being operated on (or a reformatted image of the direct optical image), at the image screen of the microscope. It is toward that precise superposition that this invention is directed, that is, establishing the spatial relationship among the imaging system, the patient, and the focal plane of the microscope.

The imaging system, as above explained, may be a CT scan, an MRI scan, a PET scan, an ultrasonic imaging device, or the like. The mechanism to introduce to the focal (image) plane 99 of the microscope 2A in FIG. 5 the computer-generated image derived from the particular imaging system is described above. The mechanism to present at that focal plane the appropriately reformatted computer-generated image is now discussed.

Figure 5:
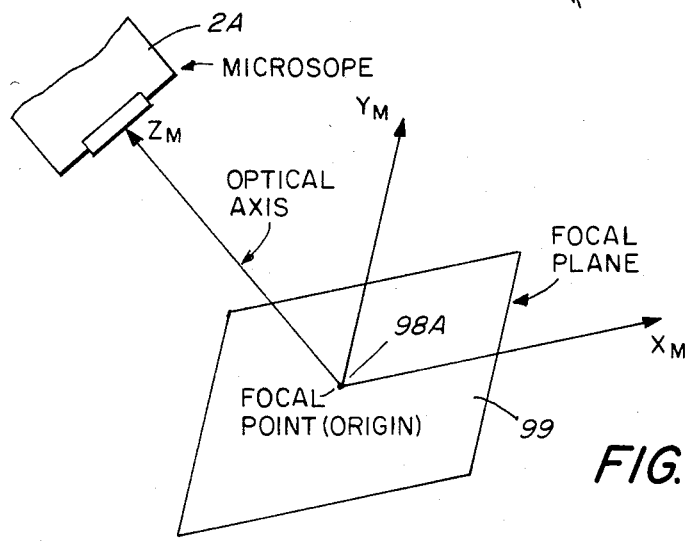
FIG. 5 shows diagrammatically the microscope of FIG. 1 and its focal plane.

Superposition of these images requires microscope, patient, and image data. This is accomplished by spatially relating both the imaging data and the operating microscope to the same points (hereinafter called fiducials) on the patient. The general registration procedure involves CT scanning the patient with at least three fiducials 22A–22C (FIG. 2) attached to the head of the patient (the patient may be supine, as shown in FIG. 2, or seated). The fiducials are composed of a material (e.g., glass), that is physically detectable by the imaging system (i.e., the CT scan at this part of the explanation) during scanning as well as visually to the microscope 2A; they are attached at a position observable by the microscope to permit focusing the microscope on the fiducials (i.e., at the focal point marked 98A in the focal plane of the microscope, as shown in FIG. 5) to achieve registration of the computer-generated image from the CT scan with the optical image of the same region of the patient at the focal plane of the microscope, as now discussed in greater detail.

A preferred way to establish the spatial relationship between the microscope and the fiducials, as well as to track any subsequent movement of the microscope, includes an ultrasonic range finder (typically using 50–60 kHz ultrasonic wave energy) or reference system 11 in FIG. 1 whose output is digitized. As shown in FIGS. 2 and 2A, the ultrasonic range finder includes at least three spark gaps 20A–20C (in a nonlinear configuration) that serves as sources of acoustic wave energy. Each gap emits the energy in the form of sound pulses which are received by (at least) three microphones 21A–21C whose positions are nonlinear and fixed in the operating room (e.g., in the ceiling marked 24 of the room). The spark gaps are located on the microscope, again marked 2A in FIG. 2, a fixed distance from the focal plane of the scope. (In practice the spark gaps 20A–20C may be removed from attachment to the microscope 2A, in which instance their position and orientation relative to the focal plane 99 must be re-established for each operation.) The use of three spark gaps allows unique delineation of both the position and the orientation of the microscope 2A with respect to the three microphones 21A–21C.

Figure 4:
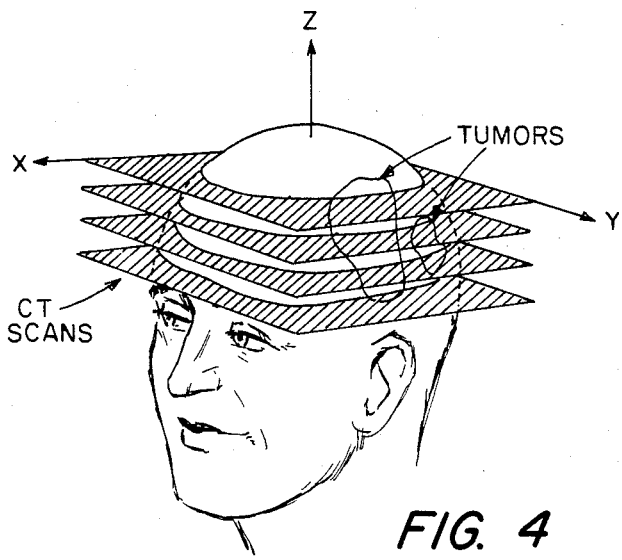
FIG. 4 shows diagrammatically the head of a patient scanned in horizontal slices to provide feedback information to the microscope.

To understand the details of the algorithms for calculating the proper reformatted image at 9 in FIG. 1 to project into the focal plane 99 in FIG. 1A of the microscope 2 in FIG. 1, it is useful to discuss three separate coordinate systems and the relationships amongst them. When three-dimensional image information of a patient is taken, e.g., a set of CT scans, an imaging coordinate system (the first of the three coordinate systems) can be established, as shown in FIG. 4 (called $X_{CT}$, $Y_{CT}$, $Z_{CT}$ hereinafter). For convenience the z-axis can be taken as parallel to the longitudinal axis of the patient and the x and y axes in the transverse plane. All initial image data is referred to this, the first, coordinate system. A second orthogonal coordinate system can be defined in the focal plane of the microscope z; let it be called ($X_M$, $Y_M$, $Z_M$). The relationships between the image (or CT coordinate system) coordinate system ($X_{CT}$, $Y_{CT}$, $Z_{CT}$) and the focal plane coordinate system ($X_M$, $Y_M$, $Z_M$) is shown in FIG. 7A. While the image (or CT coordinate system) is fixed with respect to the patient, the focal plane (or microscope) coordinate system ($X_M$, $Y_M$, $Z_M$) moves through space relative to the CT coordinate system as the microscope 2 is moved. To reformat properly the image data, a mathematical transformation that relates the image data to the focal plane must be found. The information necessary to determine this mathematical relationship is found by the ultrasonic (or magnetic or other) range finding system disclosed herein. The details for one implementation of the ultrasonic range finding system are given next. Other equivalent methods are possible and well-known in the art.

The information needed to reconstruct and display the image information can be divided into three parts: (1) the equation of the focal plane in FIG. 7A in CT coordinates is necessary to determine the appropriate reconstructed image; (2) the CT coordinates of the focal plane must be determined such that the center of the focal plane and the reconstructed slice will be properly displayed; and (3) the three direction cosines ($a_X$, $a_Y$, $a_Z$ in FIG. 7A) of the $Y_M$ axis of the microscope coordinate system with respect to the $X_{CT}$, $Y_{CT}$, and $Z_{CT}$ axes must be known to properly orient the CT image date.

Figure 7C:
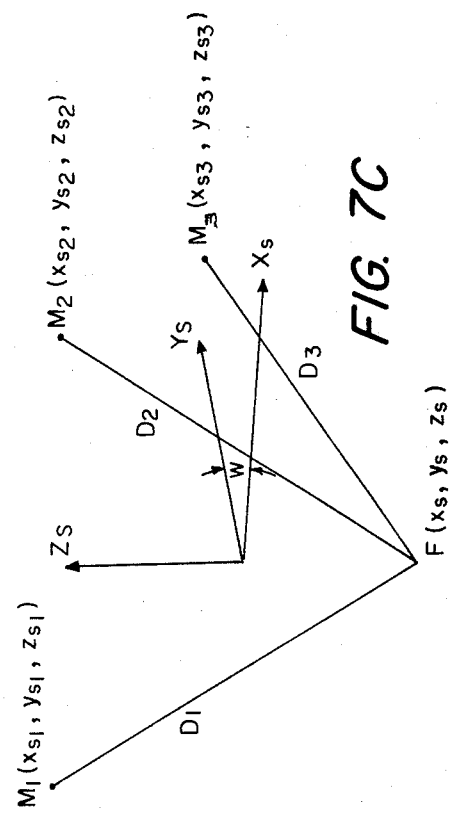
Figure 7D:
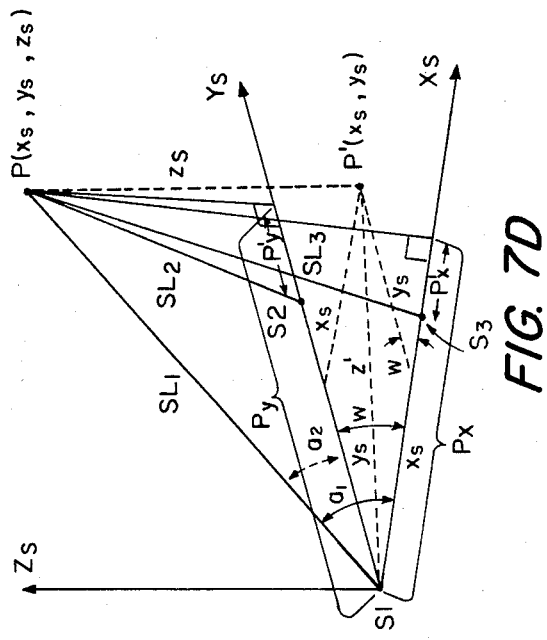
Figure 7A:
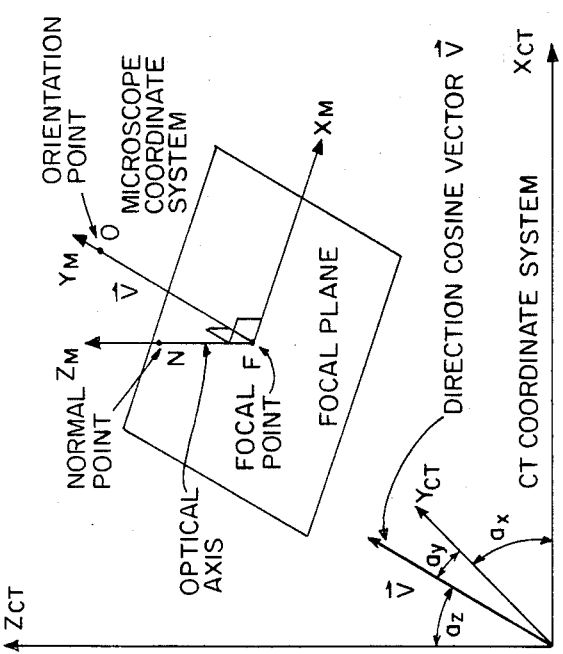
Figure 7B:
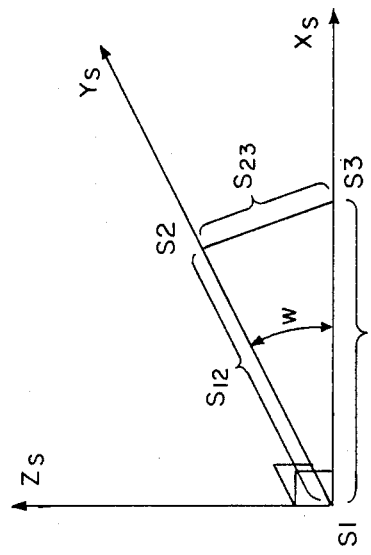

A third coordinate system, the oblique spark gap coordinate system ($X_S$, $Y_S$, $Z_S$) as shown in FIG. 7B, can also be defined to help determine the proper relationships. The coordinate system in FIG. 7B is defined by the location of the spark gaps on the microscope, i.e., by the points 20A, 20B, and 20C in FIG. 2. The focal point of the microscope and the microscope coordinate system are fixed relative to the oblique spark gap coordinate system.

To determine the oblique spark gap coordinates of the focal point, the following procedure can be used. Position a fourth spark gap (e.g., 20D in FIG. 2) at a fixed position underneath the microphones labeled $M_1$, $M_2$, and $M_3$ in FIG. 7C (that correspond to the microphones 21A, 21B and 21C in FIG. 2), fire the fourth spark gap 20D, and, using the ultrasonic digitizer, measure the slant ranges from the fourth spark gap to the three microphones, $M_1$, $M_2$, and $M_3$, which are located at distances $D_1$, $D_2$, $D_3$, respectively, from focal point F, where $D_1$ equals the distance from any microphone $M_1$ to the focal point (see FIG. 7C). Then focus the microscope 2 on the tip of the fourth spark gap 20D and fire the three spark gaps (20A, 20B, 20C in FIG. 2) on the microscope 2. Let P ($X_S$, $Y_S$, $Z_S$), represent the location of any one microphone, e.g., $M_1$, in the spark gap coordinate system (see FIG. 7D). The slant ranges, $SL_1$, $SL_2$, and $SL_3$ to the point P ($X_S$, $Y_S$, $Z_S$), are known from the ultrasonic digitizer measurements. To determine the location of the microphone ($X_S$, $Y_S$, $Z_S$) from the slant ranges, $SL_1$, $SL_2$, $SL_3$, the following equations are used.

$$P_X = (S_{31}^2 + SL_1^2 - SL_3^2)/2S_{31}$$

$$P_Y = (S_{12}^2 + SL_1^2 - SL_2^2)/2S_{12}$$

$$X_S = (P_X - P_Y \cos w)/\sin^2 w$$

$$Y_S = (P_Y - P_X \cos w)/\sin^2 w$$

$$A_S = (SL_1^2 - X_S^2 - Y_S^2 - 2X_S \cos w)^{\frac{1}{2}}$$

All quantities are defined in FIG. 7D. The quantities $S_{31}$, $S_{21}$, and w are assumed known and in practice obtained by direct measurement with precision mechanical calipers, where $S_{31}$ is the distance between the first spark gap (e.g., the spark gap 20A in FIG. 2) and the third spark gap (e.g., the spark gap 20C in FIG. 1), $S_{21}$ the distance between the first and second spark gaps, and w the angle between the line $S_{31}$ and $S_{21}$. Therefore, if $SL_1$, $SL_2$, and $SL_3$ are the slant ranges to microphone $M_1$, ($X_{S1}=X_S$, $Y_{S1}=Y_S$, $Z_{S1}=Z_S$) are the coordinates of the microphone $M_1$ in the oblique spark gap coordinate system. The coordinates of microphone $M_2$ ($X_{S2}$, $Y_{S2}$, $Z_{S2}$) are determined similarly. Hence, the location of all microphones in the spark gap coordinate system is now known.

If one lets the coordinates of the focal point in the oblique spark gap system be denoted by ($X_{fp}$, $Y_{fp}$, $Z_{fp}$), the relationship between ($D_1$, $D_2$, $D_3$) which have been measured, and ($X_{fp}$, $Y_{fp}$, $Z_{fp}$) are $$D_i^2 = (X_{fp} - X_{si})^2 + (Y_{fp} - Y_{si})^2 + (Z_{fp} - Z_{si})^2 + 2(X_{fp} - X_{si})(Y_{fp} - Y_{si})\cos w$$

i = 1,2,3

This gives three equations in the three unknowns and can be solved for $X_{fp}$, $Y_{fp}$, $Z_{fp}$ by any standard algorithm, which is well-known to those skilled in the art, for example, by using an interactive Newton method. Hence, the coordinates of the focal point in the oblique spark gap coordinate system is determined by ultrasonic range finding measurements. (It should be noted that $X_{fp}$, $Y_{fp}$, $Z_{fp}$ can be obtained more directly by measurement of the distance from the focal point to the three spark gaps. However, this measurement may not be convenient to perform in the sterile environment of the operating room, since the spark gaps and their holder must be sterilized.)

Once the coordinates of the focal point are known in the oblique spark gap coordinate system, it is necessary to determine the position and orientation of the focal plane. This information can be obtained several ways. One procedure for accomplishing this step is to focus the microscope on three known points (e.g., the fiducials 22A, 22B, and 22C herein) located at the origin and on the X and Y axes of an orthogonal coordinate system. At each of these locations the spark gaps are fired and the slant ranges recorded and stored in the computer. The microscope is then carefully positioned so the optical axis is perpendicular to the plane defined by the X-Y axis. (This operation is made possible by a knob on the microscope mounting system which moves the microscope only along this axis.) The spark gaps are again fixed and the new slant ranges are stored. Using equations well-known to those skilled in the art of mechanics and essentially equivalent to those presented above, the equation for the focal plane, properly oriented, can be determined.

As is noted above, the spatial location of the spark gaps relative to the focal plane 99 and the relative orientation of the plane defined by the three spark gaps 20A–20C and the focal plane 99 are established. The patient is placed within the view of the microscope 2A with the three (or more) fiducials in place and the patient's head is fixed. The microscope is then focused on each fiducial individually to establish the position of the information stored in the computer 6 with the location and orientation of the microscope relative to the patient. As the position of each fiducial is determined relative to the focal point 98A (FIG. 5), the spark gaps are fired to establish position and orientation with respect to the CT information stored in the computer 6 relative to the patient, thereby establishing (when all fiducials have been located) the positions of the patient's head or other body part, the fiducials and the CT scan information.

The fiducials are critical to registration of the reconstructed CT image (or the "computer-generated image" as it is also called herein) derived by the imaging system 1 in FIG. 1 with the optical image derived by the microscope 2A at the focal plane of the microscope. The spark gaps 20A–20C (FIG. 2), as above noted, are mounted on and in fixed spatial relationship to the microscope, and the microphones 21A–21C are mounted on and in fixed spatial relationship to the ceiling labeled 24 (the operating table labeled 25 is also fixed spatially within the operating room); hence, with the patient's head rigidly clamped to the table 25, the position of the fiducials 22A–22C relative to the microphones can be determined. The positions of the microphones 21A–21C with respect to the CT scan slices (FIG. 4) are then determined by focusing on each fiducial separately and the coordinates of each microphone in the CT coordinate system is established.

Once these steps are completed the system is registered and the precise spatial relationships between the fiducials located on the patient, the microphones, and the CT data stored in the computer 6 are uniquely established and the system is ready for use during a surgical procedure. After normal surgical preparation, the surgeon positions the microscope over the region of interest. When the microscope is fixed in position and not moving, the surgeon has the sparks 20A–20C fired and, using the algorithms described above, the position of the focal plane is determined in CT coordinate space. This information is passed to the image reformatting routines in the computer 6 and the CT image for the focal plane (or, at the neurosurgeon's discretion, the image of a plane at any distance below the focal plane, or the projection of an object of interest, e.g., a tumor, onto the focal plane) is calculated and displayed by the optical display system 7 in FIG. 1. Each time the microscope is repositioned the above procedure is repeated, i.e., the sparks are fired again, and a new reformatted image is calculated and displayed. There now follows a discussion of a preferred way to establish the coordinates of the microscope in the context of the operating room.

Returning now to FIG. 2, the mechanism to establish the coordinate system of the microscope 2A (and hence, coordinates of the focal plane which is what is needed) includes the spark gaps 20A–20C and the microphones 21A–21C which form part of an ultrasonic range finder (typically, acoustic wave energy of about 50–60 kHz is used) whose output is digitized. The spark gaps 20A–20C serve as a source of sound pulses; the gaps are located on the microscope 2A a fixed distance from its focal plane. The position of the microphones is fixed (and known) with respect to the operating room. The range finder notes the time elapsed between emission of each acoustic pulse by each spark gap and its reception by each of the three microphones 21A–21C. Since the speed of acoustic propagation is known, the distance, often called the slant range, between each spark gap and microphone is known. From this data the position of each spark gap relative to the fixed position of the microphones can be found. (In the context of this explanation, the ultrasonic range finder includes the spark gaps 20A–20C, the acoustic receiver or microphones 21A–21C and the computer 6 in FIG. 1.)

It should be noted that the speed of propagation of acoustic energy is affected by both temperature and humidity, but, for present purposes, humidity effects can be neglected and corrections are made in the system herein for temperature. Also, using three (or more) spark gaps and three (or more) microphones (or other transducer-receivers) in a nonlinear array permits not only the determination of position of the focal plane of the microscope 2A, it also permits determination of the orientation thereof. Some general comments now follow.

The reconstructed CT scan, as above indicated, must eventually be displayed in the microscope as a two-dimensional CRT image. This involves converting the reconstructed slice from a matrix of image data in three coordinates to one of two coordinates (x, y). A microscope coordinate system could represent the focal plane as x and y, normal to the optical axis with the origin at the focal point (see FIG. 5). This technique requires a transformation of coordinates because the microscope coordinate system will be constantly changing with respect to the location of the microphones and CT scan data of the patient as the surgeon moves the microscope. Regardless of the reference frame used for reconstructing the slice, in order to display the proper image, the slice must be transformed into microscope coordinates. The advantage of transforming all the data and performing the calculations in the microscope coordinate system is that if the surgeon moves the microscope only slightly or along the optical axis, the reconstruction calculations can be greatly reduced and allow the surgeon to quickly call up new slices for viewing. A discussion of the reference system 11, in FIG. 1, now follows.

The reference system 11 must determine the position of the microscope and its focal plane with respect to the patient's head and CT scans given the distances between spark gaps 20A–20C and microphones 21A–21C. The purpose of this explanation is to determine the appropriate placement and orientation of the spark gaps given the constraints of the ultrasonic digitizer.

As mentioned earlier, at least six pieces of information must be known about a rigid body (microscope) to locate it in a fixed coordinate system (CT). It is easier to determine the coordinates of three points (nine pieces of information) rather than the coordinates of a point and three relative angles position of the microscope. Therefore, three spark gaps are needed in addition to at least three microphones. Physical and aseptic constraints in the operating room prevent mounting either the microphones or the spark gaps on the patient's head to determine the relative microscope-CT scan positions.

The general registration procedure involves CT scanning the patient with at least three fiducials attached to the head. With the spark gaps mounted on the microscope and microphones mounted on the ceiling, the patient's head will be placed in a rigid clamp which anchors the position of the fiducials with respect to the microphones (see FIG. 2). The positions of the microphones 21A-21C with respect to the CT scans are then determined by focusing on each fiducial, as is discussed elsewhere herein.

The acoustic system described above can be replaced by an electromagnetic position and orientation measurement system, e.g., the system developed by Polhomus Navigation Sciences Division, McDonnell Douglas Electronics Company, PO Box 560, Colchester, Vt. 05446. The basic principle behind this system is to measure the back EMF (electromotive force) created in a coil 51 by a magnetic field generated by a source coil 50. The coil 51 is called the receiver or sensor coil or tracker as shown in FIG. 6A. Since the magnetic field generated by a source coil can be calculated, the voltage or back EMF induced in the second coil can also be calculated. This voltage is dependent on the source current, $I_{S1}$, the number of turns in the coils 50 and 51, the coil geometry (shown as circular in this figure), and the separation and relative orientation of the two coils 50 and 51. A single sensor and receiver coil will not uniquely determine the separation and orientation of the two coils, or even the magnetic field generated by the sensor coil at the receiving end. Since a magnetic field has three spatial components, if three receiving coils are used, as shown in FIG. 6B, the magnetic field generated by the source coil at the receiving system (consisting of three receiving coils 51A, 51B, and 51C), can be measured, and hence, the magnetic field generated by the source coil 50 in FIG. 6B is known.

To uniquely determine the position and orientation of the receiver system with respect to the source system, three source coils 50A, 50B, and 50C must be used, as shown in FIG. 6C. To determine the position and orientation of the receiver with respect to the source, the following procedure is used. First, an alternating current $I_{S1}$ is generated, and three receiving voltages ($V_{R1, 1}$, $V_{R2, 1}$, $V_{R3, 1}$) are measured and recorded. The first current is then turned off, and the second source current, $I_{S2}$ is turned on. This current generates the three voltages ($V_{R1, 2}$, $V_{R2, 2}$, $V_{R3, 2}$) which are measured and recorded. Current $I_{S2}$ is then turned off, and current $I_{S3}$ turned on, the voltages ($V_{R1, 3}$, $V_{R2, 3}$, $V_{R3, 3}$) are then measured and recorded. From knowledge of the three currents ($I_{S1}$, $I_{S2}$, $I_{S3}$) and the nine voltages ($V_{R1, 1}$, $V_{R2, 1}$, $V_{R3, 1}$, $V_{R1, 2}$, $V_{R2, 2}$, $V_{R3, 2}$, $V_{R1, 3}$, $V_{R2, 3}$, $V_{R3, 3}$), plus the number of turns for each coil and its physical dimensions, and a basic knowledge of physics, the position and orientation of the sensor coil and the receiving coil can be uniquely determined. An electromagnetic supply 53 furnishes current to the coil 50 (or 50A, 50B, and 50C) and a signal processing circuit 54 measures $V_{R1} \ldots$ ; outputs of the processor 54 are connected to the computer 6. The system in FIGS. 6A-6C provides exactly the same information as the acoustic spark-microphone system, and hence, the acoustic system can be replaced by the magnetic system.

An optical system can be used as an alternative to the acoustic system described earlier.

Further modifications of the invention herein disclosed will occur to persons skilled in the art and all such modifications are deemed to be within the scope of the invention as defined by the appended claims.

*Appendix A*

```
10 '
20 ' APPENDIX C
30 '
40 ' THESIS TITLE: REFERENCE - DISPLAY SYSTEM FOR THE INTEGRATION OF CT
50 ' SCANNING AND THE OPERATING MICROSCOPE
60 '
70 ' FILENAME: FPL
80 '
90 ' PROGRAMMER: JOHN F. HATCH
100 ' DATE: AUGUST, 1984
110 '
120 ' NOTE: REFER TO CHAPTER 6 IN THESIS FOR EQUATIONS.
130 ' AND REFERENCE 10 FOR ALGORITHMS.
140 '
150 ' THIS FILE DETERMINES THE COORDINATES OF THE FOCAL,
160 ' NORMAL AND ORIENTATION POINTS IN OBLIQUE SPARK GAP COORDINATES
170 ' FOR BOTH THE SITTING AND SUPINE SPARK GAP BRACKETS, AND STORES
180 ' THEM IN FILES SIT AND SUP.
190 '
200 OPTION BASE 1      ' SET LOWER ARRAY INDEX TO 1 FOR CONVENIENCE
210 '
220 ' ALLOCATE SPACE FOR ARRAYS
230 ' NOTE: ARRAY NAMES FOLLOWED BY A "#" SIGN ARE DOUBLE PRECISION
```

```
240 '
250 DIM J#(3,3)        ' JACOBIAN MATRIX COEFFICIENTS
260 DIM I#(3,3)        ' JACOBIAN MATRIX INVERSE
270 DIM SRMEAN(3,3)    ' MEAN SLANT RANGES
280 DIM SDATA(4,3,3)   ' SLANT RANGE DATA
290 DIM FOCAL(3,3)     ' OBLIQUE SPARK GAP COORDINATES OF THE FOCAL, NORMAL
300 '                    AND ORIENTATION POINTS
310 DIM NSOL(3,3)      ' COORDINATE SOLUTIONS TO NEWTON
320 DIM FX(3,3)        ' FIXED GRID COORDINATE SYSTEM
330 DIM MV#(3)         ' ITERATION VARIABLE (N-1)
340 DIM M#(100,3)      ' ITERATION VARIABLES
350 DIM SL(3)          ' SLANT RANGE DATA
360 DIM T(3)           ' ITERATION ERRORS
370 DIM DIST(3,3)      ' MICROPHONE-FOCAL POINT DISTANCES
380 DIM MIKE(3,3)      ' MICROPHONE COORDINATES IN FIXED GRID COORDINATE SYSTEM
390 DIM NPOINT(3)      ' NORMAL POINT COORDINATES IN FIXED GRID COORDINATE SYS.
400 DIM OPOINT(3)      ' ORIENTATION POINT COORDINATES IN FIXED GRID SYSTEM
410 DIM GRID(3,3)      ' COORDINATES OF MICROPHONE PLANE GRID
420 DIM SLANT(150,3)   ' SLANT RANGES
430 DIM F#(4)          ' ITERATIVE SOLUTION TO NEWTON
431 DIM CLASS(7)       'HISTOGRAM CLASSES
432 DIM MICE(4,3)      'MICROPHONE ARRAY
433 DIM SMEAN(3)       'STANDARD DEVIATIONS OF SLANTRANGES
434 DIM BAD(3)         'SLANTRANGES > 245CM
435 DIM SD(3)          'STANDARD DEVIATIONS OF SLANTRANGES
436 MICE(1,1)=3: MICE(1,2)=4: MICE(1,3)=2: MICE(2,1)=1: MICE(2,2)=3
437 MICE(2,3)=4: MICE(3,1)=4: MICE(3,2)=2: MICE(3,3)=1: MICE(4,1)=3
438 MICE(4,2)=1: MICE(4,3)=2
439 SCALL = 0
443 '
450 ' MEASURED DISTANCES BETWEEN SPARK GAPS IN CM.
460 S12=30.041         ' SPARK GAP 1 - SPARK GAP 2
470 S23=29.995         ' SPARK GAP 2 - SPARK GAP 3
480 S31=29.657         ' SPARK GAP 3 - SPARK GAP 1
490 '
500 CW=(S12^2+S31^2-S23^2)/(2*S12*S31)  ' COSINE OF ANGLE W, S2-S1-S3 EQN. 6.1
510 S2W=1-CW*CW                         ' SINE SQUARED OF ANGLE W, S2-S1-S3
511 '
512 SPT = 1
513 PRINT"IF FPL FAILED PREVIOUSLY THEN YOU CAN RESUME AT ANY STAGE."
514 PRINT"ANSWER 'Y' IF YOU WANT TO RESUME, ANSWER 'N' IF THIS IS THE"
515 PRINT"FIRST RUN OR YOU WANT TO REDO FPL COMPLETELY";
516 INPUT ANSWER$
517 IF ANSWER$="N" THEN GOTO 550
518 IF ANSWER$<>"Y" THEN GOTO 513
519 PRINT
520 PRINT"ENTER THE NUMBER OF THE GRIDPOINT FROM WHICH YOU WANT TO RESTART";
521 INPUT SPT
522 OPEN "RESUME.DAT" FOR INPUT AS #3
523 INPUT #3, MNOT
524 INPUT #3, NUMSPAR
525 FOR LOOP1 = 1 TO 3
526    INPUT #3, FOCAL(1,LOOP1)
527 NEXT LOOP1
528 FOR LOOP1 = 1 TO SPT
529    FOR LOOP2 = 1 TO 3
530       FOR LOOP3 = 1 TO 3
531          INPUT #3, SDATA(LOOP1,LOOP2,LOOP3)
532       NEXT LOOP3
533    NEXT LOOP2
534 NEXT LOOP1
535 CLOSE #3
536 SCALL = SPT + 1: ITER = 35
537 OPEN "FPL.LOG" FOR OUTPUT AS #2
538 GOTO 2010
550 '
560 PRINT
570 PRINT"WHICH MICROPHONE SHOULD BE SHUT OFF ?";
580 INPUT MNOT
590 '
660 PRINT
670 PRINT"TURN ON DIGITIZER AND SPARK GAP MULTIPLEXER."
680 PRINT
690 PRINT"NOTE:  THE DIGITIZER/COMPUTER COMMUNICATIONS MAY FAIL INITIALLY."
700 PRINT"DO NOT WORRY - THIS IS NORMAL.  JUST RETYPE 'FPL' WITHOUT TURNING"
710 PRINT"OFF THE DIGITIZER AND YOU SHOULD HAVE NO PROBLEM."
720 '
730 ' CALL SUBROUTINE FPLANE TO DETERMINE THE OBLIQUE SPARK GAP COORDINATES
740 ' OF THE FOCAL, NORMAL AND ORIENTATION POINTS
750 '
760 GOSUB 1170 ' CALL FPLANE
770 '
```

```
780 ' NOW THAT THE RELATIONSHIP BETWEEN THE SPARK GAPS AND THE FOCAL PLANE
790 ' HAS BEEN ESTABLISHED, STOP THE PROGRAM.
800 '
810 STOP
820 '
830 ' SUBROUTINE: DISTANCE
840 '
850 ' THIS SUBROUTINE CALCULATES THE DISTANCE FROM THE FOCAL POINT IN OBLIQUE
860 ' SPARK GAP COORDINATES AND THE MICROPHONES.
870 '
880 ' INPUTS: FOCAL(1,COORD) - OBLIQUE SPARK GAP COORDINATES OF FOCAL POINT;
890 '         SL(POINT) - SLANT RANGE DISTANCE TO MICROPHONES;
900 '         CW - COSINE OF ANGLE W, S2-S1-S3 (SPARK GAPS);
910 '         S2W - SINE SQUARED OF ANGLE W, S2-S1-S3 (SPARK GAPS)
920 ' OUTPUT: D - DISTANCE FROM FOCAL POINT TO MICROPHONE
930 '
940 ' POINT 1 - OBLIQUE MICROPHONE COORDINATES
950 '
960 ' CALCULATE PROJECTIONS OF SLANT 1 ON X AND Y SPARK AXES
970 XP1=(SL(1)^2+S31^2-SL(3)^2)/(2*S31)    ' EQN. 6.3
980 YP1=(SL(1)^2+S12^2-SL(2)^2)/(2*S12)    ' EQN. 6.4
990 '
1000 ' CALCULATE OBLIQUE COORDINATES OF POINT 1
1010 X1=(XP1-YP1*CW)/S2W                   ' EQN. 6.8
1020 Y1=(YP1-XP1*CW)/S2W                   ' EQN. 6.9
1030 Z1=(SL(1)^2-X1^2-Y1^2-2*X1*Y1*CW)^.5  ' EQN. 6.12
1040 '
1050 ' POINT 2 - FOCAL POINT COORDINATES
1060 '
1070 X2=FOCAL(1,1)
1080 Y2=FOCAL(1,2)
1090 Z2=FOCAL(1,3)
1100 '
1110 ' CALCULATE DISTANCE D USING OBLIQUE DISTANCE FORMULA, EQN 6.14
1120 '
1130 D=(X2-X1)^2+(Y2-Y1)^2+(Z2-Z1)^2+2*(X2-X1)*(Y2-Y1)*CW
1140 '
1150 RETURN
1160 '
1170 ' SUBROUTINE: FPLANE
1180 '
1190 ' THIS SUBROUTINE DETERMINES THE OBLIQUE SPARK GAP COORDINATES OF THE
1200 ' FOCAL, NORMAL AND ORIENTATION POINTS FOR THE SITTING OR SUPINE SPARK
1210 ' BRACKET.
1220 '
1230 ' OUTPUT: FOCAL(POINT,COORD) - OBLIQUE SPARK GAP COORDINATES OF THE FOCAL,
1240 '           NORMAL AND ORIENTATION POINTS
1250 ' SUBROUTINES NEEDED: SRINP, NEWTON, STORE, DISTANCE
1255 OPEN "FPL.LOG" FOR OUTPUT AS #2
1260 '
1261 PRINT
1262 PRINT"HOW MANY SPARKS DO YOU WANT TO FIRE (MAX. 150) ?";
1263 INPUT NUMSPAR
1264 IF (NUMSPAR>150) OR (NUMSPAR<1) THEN GOTO 1261
1265 PRINT
1270 PRINT
1280 PRINT"ANCHOR THE FOURTH SPARK GAP UNDER THE MICROPHONES SUCH THAT IT CAN"
1290 PRINT"BE EASILY FOCUSED UPON.  CONNECT THE SPARK GAP TO THE 'SPARK GAP 1'"
1300 PRINT"OUTPUT ON THE SPARK GAP MULTIPLEXER. MAKE SURE MICROSCOPE IS OUT OF"
1310 PRINT"THE WAY.  DO NOT MOVE OR DISTURB THIS SPARK GAP WITH RESPECT TO THE"
1320 PRINT"MICROPHONES ONCE IT HAS BEEN ACTIVATED (FIRED) BY THE DIGITIZER!"
1330 '
1340 ' SET SPARK GAP FLAG TO 1 INDICATING ONLY ONE SPARK GAP MUST BE FIRED
1350 SFLAG=1
1360 '
1370 ' FIRE FOURTH SPARK GAP TO DETERMINE THE DISTANCES BETWEEN THE FOCAL POINT
1380 ' AND THE MICROPHONES.
1390 '
1399 SCALL = SCALL + 1
1400 GOSUB 4070 ' CALL SRINP
1410 '
1420 ' STORE THE SQUARED SLANT RANGES IN ARRAY DIST TO BE USED BY NEWTON
1430 FOR MK=1 TO 3                   ' STEP THROUGH EACH MICROPHONE
1440   DIST(MK,1)=(SRMEAN(MK,1))^2   ' MICROPHONE - FOCAL POINT DISTANCES
1450 NEXT MK                          ' NEXT MICROPHONE
1460 '
1470 PRINT
1480 PRINT"CONNECT ALL THREE SPARK GAPS TO THE SPARK GAP MULTIPLEXER AND THEN"
1490 PRINT"FOCUS THE MICROSCOPE, AT THE HIGHEST MAGNIFICATION (2.5), ON THE"
1500 PRINT"TIP OF THE FOURTH SPARK GAP, MAKING SURE THE FOURTH SPARK GAP IS"
1510 PRINT"NOT DISTURBED."
1520 '
```

```
1530 ' COLLECT SLANT RANGES FOR FOCUSED MICROSCOPE
1539 SCALL = SCALL + 1
1540 GOSUB 4070       ' CALL SRINP
1550 '
1560 ' CALCULATE THE OBLIQUE SPARK GAP COORDINATES OF THE THREE MICROPHONES
1570 ' GIVEN THEIR SLANT RANGES.
1580 '
1590 FOR MK=1 TO 3      ' STEP THROUGH EACH MICROPHONE
1600 '
1610 ' CALCULATE PROJECTIONS OF SLANT RANGE 1 ON THE X AND Y SPARK GAP AXES
1620 '
1630   XP=(SRMEAN(MK,1)^2+S31^2-SRMEAN(MK,3)^2)/(2*S31)  ' EQN. 6.3
1640   YP=(SRMEAN(MK,1)^2+S12^2-SRMEAN(MK,2)^2)/(2*S12)  ' EQN. 6.4
1650 '
1660 ' CALCULATE THE OBLIQUE COORDINATES OF MICROPHONE MK
1670   FX(MK,1)=(XP-YP*CW)/S2W       ' EQN. 6.8
1680   FX(MK,2)=(YP-XP*CW)/S2W       ' EQN. 6.9
1690   FX(MK,3)=(SRMEAN(MK,1)^2-FX(MK,1)^2-FX(MK,2)^2-2*FX(MK,1)*FX(MK,2)*CW)^.5
1700 ' EQN. 6.12
1710 '
1720 NEXT MK            ' NEXT MICROPHONE
1730 '
1740 ' CALCULATE COORDINATES OF FOCAL POINT IN SPARK GAP COORDINATES BY SOLVING
1750 ' THREE NONLINEAR DISTANCE EQUATIONS FOR THE THREE COORDINATES.
1760 '
1770 ' CALL SUBROUTINE NEWTON WITH NFLAG=1 WHICH WILL TAKE THE OBLIQUE
1780 ' MICROPHONE COORDINATES STORED IN ARRAY FX, AND THE DISTANCES STORED IN
1790 ' ARRAY DIST AND SOLVE EQN. 6.13.
1800 '
1810 NFLAG=1   ' SET FLAG TO 1 SUCH THAT NEWTON SOLVES EQUATIONS 6.13.
1820 GOSUB 5530 ' CALL NEWTON
1821 OPEN "FOCAL.LOG" FOR OUTPUT AS #3
1822 PRINT #3,"OBLIQUE FOCAL POINT COORDINATES"
1823 PRINT #3,"X-COORD:",NSOL(1,1)
1824 PRINT #3,"Y-COORD:",NSOL(1,2)
1825 PRINT #3,"Z-COORD:",NSOL(1,3)
1826 CLOSE #3
1827 '
1830 '
1840 ' STORE THE OBLIQUE COORDINATES OF THE FOCAL POINT, FROM SUBROUTINE NEWTON
1841 ' IN ARRAY FOCAL.
1842 '
1843 PRINT"THE OBLIQUE FOCAL POINT COORDINATES DETERMINED BY FPL ARE:"
1844 PRINT"X:",NSOL(1,1)," Y:",NSOL(1,2)," Z:",NSOL(1,3)
1847 PRINT
1848 PRINT"ANSWER 'O' IF YOU WANT TO USE THE COORDINATES DETERMINED BY"
1849 PRINT"FPL; ANSWER 'M' IF YOU WANT TO USE THE MEASURED COORDINATES";
1850 INPUT ANS$
1851 IF ANS$="M" THEN PRINT"ENTER THE X,Y,Z COORDINATES OF THE FOCAL POINT": INPUT NSOL(1,1),
     NSOL(1,2),NSOL(1,3)  GOTO 1861
1852 IF ANS$<>"O" THEN GOTO 1848
1853 '
1861 OPEN "RESUME.DAT" FOR OUTPUT AS #3
1862 PRINT #3,MNOT
1863 PRINT #3,NUMSPAR
1870 FOR COORD=1 TO 3              ' STEP THROUGH X,Y,Z
1880   FOCAL(1,COORD)=NSOL(1,COORD)  ' STORE COORDINATE
1881   PRINT #3,NSOL(1,COORD)
1890 NEXT COORD                    ' NEXT COORDINATE
1891 CLOSE #3
1900 '
1910 ' COLLECT THE SLANT RANGE DATA FOR THE GRID COORDINATE SYSTEM (FIG 9.1).
1920 ' THIS DATA IS THE DISTANCES FROM EACH OF THE THREE SPARK GAPS TO
1930 ' THE THREE MICROPHONES FOR GRID POINTS 1, 2 AND 3 (NORMAL TO THE
1940 ' Z AXIS OF THE GRID COORDINATE SYSTEM), AND THE NORMAL POINT ALONG
1950 ' THE OPTICAL AXIS.
1960 '
1970 PRINT"LOCATE THE GRID COORDINATE SYSTEM WITH THE PROTRACTOR, RESET THE"
1980 PRINT"PROTRACTOR TO 0 DEGREES AND ANCHOR IT UNDER THE MICROSCOPE."
1990 PRINT
2000 '
2010 ' STORE FIXED CARTESIAN GRID COORDINATES
2020 GRID(1,1)=0:  GRID(1,2)=10.246: GRID(1,3)=0
2030 GRID(2,1)=10.114: GRID(2,2)=0: GRID(2,3)=0
2040 GRID(3,1)=0: GRID(3,2)=0: GRID(3,3)=0
2050 '
2060 FOR PT=SPT TO 4         ' STEP THROUGH EACH POINT
2070   IF PT=1 THEN PRINT"FOCUS ON PT. 1"
2080   IF PT=2 THEN PRINT"FOCUS ON PT. 2"
2090   IF PT=3 THEN PRINT"FOCUS ON PT. 3 NORMAL TO GRID WITH THE CROSSHAIRS"
```

```
2100  IF PT=3 THEN PRINT"IN THE MICROSCOPE ALIGNED WITH THOSE OF THE"
2110  IF PT=3 THEN PRINT"PROTRACTOR SET AT 0 DEGREES. MAKE SURE THAT THE"
2120  IF PT=3 THEN PRINT"FOCUSING KNOB IS TURNED SUCH THAT THE MICROSCOPE IS"
2130  IF PT=3 THEN PRINT"AS CLOSE TO THE GRID COORDINATE SYSTEM AS POSSIBLE."
2140  IF PT=4 THEN PRINT"MOVE MICROSCOPE ALONG OPTICAL AXIS, AWAY FROM GRID"
2150  IF PT=4 THEN PRINT"BY TURNING THE MICROSCOPE FOCUSING KNOB."
2160  '
2170  ' COLLECT SLANT RANGE DATA
2179  SCALL = SCALL + 1
2180  GOSUB 4070         ' CALL SRINP
2190  '
2200  FOR MK=1 TO 3                  ' STEP THROUGH EACH MICROPHONE
2210   FOR SPK=1 TO 3                ' STEP THROUGH EACH SPARK GAP
2220  ' STORE SLANT RANGE DATA IN ARRAY SDATA
2230     SDATA(PT,MK,SPK)=SRMEAN(MK,SPK)
2240    NEXT SPK                     ' NEXT SPARK GAP
2250   NEXT MK                       ' NEXT MICROPHONE
2251  OPEN "RESUME.DAT" FOR OUTPUT AS #3
2252  PRINT #3,MNOT
2253  PRINT #3,NUMSPAR
2254  FOR LOOP1=1 TO 3
2255     PRINT#3,FOCAL(1,LOOP1)
2256  NEXT LOOP1
2257  FOR LOOP1=1 TO PT
2258     FOR LOOP2=1 TO 3
2259        FOR LOOP3=1 TO 3
2260           PRINT#3,SDATA(LOOP1,LOOP2,LOOP3)
2261        NEXT LOOP3
2262     NEXT LOOP2
2263  NEXT LOOP1
2264  CLOSE #3
2265  '
2278  NEXT PT                        ' NEXT GRID POINT
2279  '
2280  ' CALCULATE DISTANCES FROM GRID POINTS 1, 2 AND 3 TO MICROPHONES
2290  '
2300  FOR PT=1 TO 3        ' STEP THROUGH EACH GRID POINT
2310   FOR MK=1 TO 3       ' STEP THROUGH EACH MICROPHONE
2320    FOR SPK=1 TO 3     ' STEP THROUGH EACH SPARK GAP
2330  ' STORE SLANT RANGES IN VECTOR SL
2340     SL(SPK)=SDATA(PT,MK,SPK)
2350    NEXT SPK           ' NEXT SPARK GAP
2360  '
2370  ' CALCULATE THE DISTANCES FROM THE FOCAL POINT (POINTS 1, 2 AND 3)
2380  ' TO THE MICROPHONES BY CALLING SUBROUTINE DISTANCE GIVEN SLANT RANGES
2390  ' STORED IN VECTOR SL
2400  '
2410    GOSUB 830          ' CALL DISTANCE
2420  '
2430  ' STORE SQUARED DISTANCES BETWEEN FOCAL POINT AND MICROPHONES IN ARRAY
2440  ' DIST FOR SUBROUTINE NEWTON.
2450  '
2460    DIST(PT,MK)=D
2470   NEXT MK             ' NEXT MICROPHONE
2480  NEXT PT              ' NEXT GRID POINT
2490  '
2500  ' STORE GRID COORDINATES IN FIXED ARRAY FOR SUBROUTINE NEWTON
2510  FOR PT=1 TO 3                  ' STEP THROUGH EACH GRID POINT
2520   FOR COORD=1 TO 3              ' STEP THROUGH X,Y,Z
2530    FX(PT,COORD)=GRID(PT,COORD)  ' STORE GRID COORDINATES IN ARRAY FX
2540   NEXT COORD                    ' NEXT COORDINATE
2550  NEXT PT                        ' NEXT GRID POINT
2560  '
2570  ' CALCULATE MICROPHONE COORDINATES
2580  '
2590  PRINT"CALCULATING MICROPHONE COORDINATES..."
2600  '
2610  NFLAG=0    ' SET NFLAG TO 0 SUCH THAT NEWTON WILL SOLVE EQUATIONS 6.15.
2620  GOSUB 5530    ' CALL NEWTON TO SOLVE FOR THE GRID MICROPHONE COORDINATES
2630  '
2640  ' STORE MICROPHONE COORDINATES
2650  '
2651  OPEN "MIKE.LOC" FOR OUTPUT AS #3
2652  PRINT #3, MNOT
2660  FOR MK=1 TO 3                  ' STEP THROUGH EACH MICROPHONE
2661    PRINT #3, NSOL(MK,1), NSOL(MK,2), NSOL(MK,3)
2670   FOR COORD=1 TO 3              ' STEP THROUGH X,Y,Z
2680    MIKE(MK,COORD)=NSOL(MK,COORD) ' STORE NEWTON SOLUTIONS IN ARRAY MIKE
2690   NEXT COORD                    ' NEXT COORDINATE
2700  NEXT MK                        ' NEXT MICROPHONE
2701  CLOSE #3
2710  '
```

```
2720 ' CALCULATE THE DISTANCES FROM THE NORMAL POINT (DETERMINED WHEN THE
2730 ' MICROSCOPE WAS MOVED ALONG THE OPTICAL AXIS AWAY FROM THE X-Y PLANE
2740 ' OF THE GRID COORDINATE SYSTEM) TO EACH OF THE THREE MICROPHONES BY
2750 ' CALLING SUBROUTINE DISTANCE.
2760 '
2770 FOR MK=1 TO 3                   ' STEP THROUGH EACH MICROPHONE
2780  FOR SPK=1 TO 3                 ' STEP THROUGH EACH SPARK GAP
2790   SL(SPK)=SDATA(4,MK,SPK)       ' STORE SLANT RANGE DATA IN VECTOR SL
2800  NEXT SPK                       ' NEXT SPARK GAP
2810 '
2820 ' CALL SUBROUTINE DISTANCE TO DETERMINE THE DISTANCES BETWEEN THE
2830 ' NORMAL POINT AND THE MICROPHONES.
2840 '
2850  GOSUB 830    ' CALL DISTANCE
2860 '
2870 ' STORE THE SQUARE OF THE DISTANCE IN ARRAY DIST
2880 '
2890  DIST(MK,1)=D
2900 '
2910 NEXT MK                         ' NEXT MICROPHONE
2920 '
2930 ' STORE MICROPHONE COORDINATES IN ARRAY FX FOR SUBROUTINE NEWTON
2940 '
2950 FOR MK=1 TO 3                   ' STEP THROUGH EACH MICROPHONE
2960  FOR COORD=1 TO 3               ' STEP THROUGH X,Y,Z
2970   FX(MK,COORD)=MIKE(MK,COORD)   ' STORE COORDINATES
2980  NEXT COORD                     ' NEXT COORDINATE
2990 NEXT MK                         ' NEXT MICROPHONE
3000 '
3010 ' CALCULATE THE NORMAL POINT COORDINATES IN THE FIXED GRID COORD. SYSTEM
3020 '
3030 PRINT"CALCULATING NORMAL POINT COORDINATES..."
3040 '
3050 NFLAG=2    ' SET NFLAG TO 2 SUCH THAT NEWTON WILL SOLVE EQUATIONS 6.16
3060 GOSUB 5530    ' CALL NEWTON
3070 '
3080 ' STORE NORMAL POINT GRID COORDINATES IN VECTOR NPOINT
3090 '
3100 FOR COORD=1 TO 3                ' STEP THROUGH X,Y,Z
3110  NPOINT(COORD)=NSOL(1,COORD)    ' STORE GRID COORDINATES
3120 NEXT COORD                      ' NEXT COORDINATE
3130 '
3140 ' THE NEXT STEP IS TO CALCULATE THE COORDINATES OF THE MICROPHONES IN THE
3150 ' OBLIQUE SPARK GAP COORDINATE SYSTEM (WITH THE MICROSCOPE AT THE NORMAL
3160 ' POINT.) WITH THESE COORDINATES IN ARRAY FX, AND THE DISTANCES FROM EACH
3170 ' MICROPHONE TO THE NORMAL POINT KNOWN BY APPLYING EQUATION 6.15 TO THE
3180 ' COORDINATES IN ARRAY MIKE AND VECTOR NPOINT, SUBROUTINE NEWTON WILL
3190 ' SOLVE THE THREE NONLINEAR EQUATIONS OF EQUATION 6.17 FOR THE OBLIQUE
3200 ' SPARK GAP COORDINATES OF THE NORMAL POINT.
3210 '
3220 FOR MK=1 TO 3         ' STEP THROUGH EACH MICROPHONE
3230 '
3240 ' CALCULATE PROJECTION OF SLANT RANGE 1 ONTO THE X AND Y SPARK AXES.
3250 '
3260  XP=(SDATA(3,MK,1)^2+S31^2-SDATA(3,MK,3)^2)/(2*S31)  ' EQN. 6.3
3270  YP=(SDATA(3,MK,1)^2+S12^2-SDATA(3,MK,2)^2)/(2*S12)  ' EQN. 6.4
3280 '
3290 ' CALCULATE THE OBLIQUE SPARK GAP COORDINATES OF EACH MICROPHONE AND
3300 ' STORE IN ARRAY FX FOR SUBROUTINE NEWTON.
3310 '
3320  FX(MK,1)=(XP-YP*CW)/S2W        ' EQN. 6.8
3330  FX(MK,2)=(YP-XP*CW)/S2W        ' EQN. 6.9
3340  FX(MK,3)=(SDATA(3,MK,1)^2-FX(MK,1)^2-FX(MK,2)^2-2*FX(MK,1)*FX(MK,2)*CW)^.5
3350 ' EQN  6.12
3360 '
3370 ' CALCULATE THE DISTANCE BETWEEN THE NORMAL POINT AND EACH MICROPHONE IN
3380 ' THE GRID COORDINATE SYSTEM.
3390 '
3400  DIST(MK,1)=(MIKE(MK,1)-NPOINT(1))^2+(MIKE(MK,2)-NPOINT(2))^2+(MIKE(MK,3)-NPOINT(3))^2
3410 '
3420 NEXT MK              ' NEXT MICROPHONE
3430 '
3440 ' SOLVE FOR THE OBLIQUE COORDINATES OF THE NORMAL POINT BY CALLING
3450 ' SUBROUTINE NEWTON.
3460 '
3470 NFLAG=1 ' SET NFLAG TO 1 SUCH THAT NEWTON SOLVES EQUATIONS 6.17.
3480 GOSUB 5530 ' CALL NEWTON
3490 '
3500 ' STORE OBLIQUE NORMAL POINT COORDINATES IN ARRAY FOCAL.
3510 '
3520 FOR COORD=1 TO 3                'STEP THROUGH X,Y,Z
3530  FOCAL(2,COORD)=NSOL(1,COORD)   ' STORE COORDINATE
3540 NEXT COORD                      ' NEXT COORDINATE
```

```
3550 '
3560 PRINT"CALCULATING ORIENTATION POINT COORDINATES..."
3570 '
3580 ' CALCULATE THE COORDINATES OF THE PROJECTED GRID POINT 1 ONTO THE FOCAL
3590 ' PLANE - WHICH IS THE ORIENTATION POINT, STORED IN VECTOR OPOINT.
3600 '
3610 KK=NPOINT(1)^2+NPOINT(2)^2+NPOINT(3)^2
3620 T=(-NPOINT(1)*GRID(1,1)-NPOINT(2)*GRID(1,2)-NPOINT(3)*GRID(1,3))/KK
3630 ' EQN  6.26
3640 '
3650 FOR COORD=1 TO 3                        ' STEP THROUGH X,Y,Z
3660   OPOINT(COORD)=NPOINT(COORD)*T+GRID(1,COORD)
3670 NEXT COORD                              ' NEXT COORDINATE
3680 '
3690 ' AS WITH THE NORMAL POINT, THE OBLIQUE SPARK GAP COORDINATES OF THE
3700 ' ORIENTATION POINT MUST BE KNOWN.  FIRST THE OBLIQUE COORDINATES OF THE
3710 ' MICROPHONES MUST BE DETERMINED WITH THE MICROSCOPE FOCUSED ON THE GRID
3720 ' ORIGIN.   THEN THE DISTANCES BETWEEN THE MICROPHONES AND THE ORIENTATION
3730 ' POINT MUST BE CALCULATED, AND THIS INFORMATION USED WITH THE SUBROUTINE
3740 ' NEWTON TO CALCULATE THE OBLIQUE SPARK GAP COORDINATES OF THE ORIENTATION
3750 ' POINT.
3760 '
3770 FOR MK=1 TO 3         ' STEP THROUGH EACH MICROPHONE
3780 '
3790 ' CALCULATE THE DISTANCE BETWEEN THE ORIENTATION POINT AND THE MICROPHONES
3800 DIST(MK,1)=(MIKE(MK,1)-OPOINT(1))^2+(MIKE(MK,2)-OPOINT(2))^2+(MIKE(MK,3)-OPOINT(3))^2
3810 NEXT MK               ' NEXT MICROPHONE
3820 '
3830 ' SUBROUTINE NEWTON WILL THEN SOLVE EQUATIONS 6.27 FOR THE OBLIQUE
3840 ' SPARK GAP COORDINATES OF THE ORIENTATION POINT.
3850 '
3860 NFLAG=1 ' SET NFLAG TO 1 SUCH THAT NEWTON WILL SOLVE EQUATIONS 6.27.
3870 GOSUB 5530  ' CALL NEWTON
3880 '
3890 ' STORE OBLIQUE ORIENTATION POINT COORDINATES IN ARRAY FOCAL
3900 '
3910 FOR COORD=1 TO 3              ' STEP THROUGH X,Y,Z
3920   FOCAL(3,COORD)=NSOL(1,COORD) ' STORE COORDINATE
3930 NEXT COORD                    ' NEXT COORDINATE
3940 '
3950 PRINT
3960 PRINT"THE OBLIQUE COORDINATES OF THE FOCAL, NORMAL AND ORIENTATION"
3970 PRINT"POINTS HAVE BEEN DETERMINED AND STORED IN ARRAY - ";BRACK$
3980 PRINT
3990 PRINT"READY TO RUN FILE: REG"
4000 CLOSE #2
4010 '
4020 GOSUB 7250 'STORE FOCAL PLANE DATA
4030 PRINT"CHANGE NAME OF FILE FPL.LOG TO AVOID OVERWRITING"
4031 PRINT
4040 '
4050 RETURN
4060 '
4070 ' SUBROUTINE: SRINP
4080 '
4090 ' THIS FILE OPENS THE RS-232 PORT FOR DIGITIZER COMMUNICATIONS,
4100 ' CONTROLS THE SPARK GAP MULTIPLEXER, STORES THE SLANT RANGES
4110 ' IN AN ARRAY, AND DETERMINES THE STANDARD DEVIATIONS AND MEANS.
4120 '
4130 ' INPUT: MNOT - IGNORED MICROPHONE
4140 ' OUTPUT: SRMEAN(MIKE,SKGAP) - AVERAGE SLANT RANGES FOR EACH SPARK GAP
4150 '
4160 PRINT
4170 PRINT "*****PRESS ANY KEY WHEN FOCUSED/READY*****"
4180 PRINT
4190 '
4200 ' PAUSE UNTIL ANY KEY IS DEPRESSED
4210 P$=INKEY$: IF P$="" THEN 4210
4220 '
4230 IF SFLAG=1 THEN SMAX=0 ELSE SMAX=2  ' SET NUMBER OF SPARK GAPS
4240 '
4250 FOR SGAP=0 TO SMAX    ' SET MULTIPLEXER THROUGH PARALLEL PORT
4260 ' CHANGE SGAP TO SGAP1 FOR PROPER MULTIPLEXER SEQUENCING
4270   IF SGAP=0 THEN SGAP1=0
4280   IF SGAP=1 THEN SGAP1=2
4290   IF SGAP=2 THEN SGAP1=1
4300 '
4310 ' WRITE THE BINARY CODE FOR SGAP1 TO THE PARALLEL PORT ADDRESS 3BC HEX
4320   OUT &H3BC,SGAP1
4330 '
4340 ' OPEN RS-232 PORT, SET BAUD RATE AND PARITY
4350   OPEN "COM1:9600,0,7,1" AS #1
4360 '
```

```
4370    FLAG=1          ' INITIALIZE CHARACTER FLAG
4380    WHILE FLAG      ' SEARCH CHARACTER INPUT FOR ASCII LINE FEED IF FLAG=1
4390     S$=INPUT$(1,#1)
4400      IF ASC(S$)=10 THEN FLAG=0 ELSE FLAG=1
4410    WEND
4420 '
4430 W$=INPUT$(26,#1)   ' IGNORE FIRST VALUES (FROM LAST SLANT RANGES)
4440 '
4460 FOR I=1 TO NUMSPAR   ' FIRE EACH SPARK GAP 150 TIMES
4470 '
4480 ' MONITOR COMM. BUFFER, IF >40 CHARACTERS IN BUFFER TURN OFF DIGITIZER
4490 ' BY WRITING BINARY CODE 10 TO ADDRESS 3FC HEX - THE RS-232 PORT
4500 '
4510    IF LOC(1)>40 THEN OUT &H3FC,10 ELSE OUT &H3FC,11
4520 '
4530 ' INPUT SLANT RANGES AND INSERT DECIMAL POINTS TO READ DISTANCES IN CM.
4540 '
4550    A$=INPUT$(26,#1)    ' INPUT 26 CHARACTER STRING (4 SLANT RANGES)
4560 '
4570    C$=MID$(A$,1,6): CL$=LEFT$(C$,3): CR$=RIGHT$(C$,3): CC$=CL$+"."+CR$
4580    D$=MID$(A$,7,6): DL$=LEFT$(D$,3): DR$=RIGHT$(D$,3): DD$=DL$+"."+DR$
4590    E$=MID$(A$,13,6): EL$=LEFT$(E$,3): ER$=RIGHT$(E$,3): EE$=EL$+"."+ER$
4600    F$=MID$(A$,19,6): FL$=LEFT$(F$,3): FR$=RIGHT$(F$,3): FF$=FL$+"."+FR$
4610 '
4620 ' STORE THE VALUE OF EACH CHARACTER STRING FOR EACH SLANT RANGE IN G1-4
4630    G1=VAL(CC$): G2=VAL(DD$): G3=VAL(EE$): G4=VAL(FF$)
4640 '
4650 ' IGNORE SLANT RANGE DATA FROM MICROPHONE MNOT AND STORE REMAINING
4660 ' SLANT RANGES IN P1-3
4670 '
4680    IF MNOT=1 THEN P1=G3: P2=G4: P3=G2
4690    IF MNOT=2 THEN P1=G1: P2=G3: P3=G4
4700    IF MNOT=3 THEN P1=G4: P2=G2: P3=G1
4710    IF MNOT=4 THEN P1=G3: P2=G1: P3=G2
4720 '
4730 ' STORE SLANT RANGES IN ARRAY SLANT
4740    SLANT(I,1)=P1: SLANT(I,2)=P2: SLANT(I,3)=P3
4750 '
4760 NEXT I     ' GET NEXT SET OF FOUR SLANT RANGES
4770 '
4780 CLOSE #1   ' SUPPRESS DIGITIZER COMMUNICATION
4790 '
4800 ' CALCULATE MEAN SLANT RANGE VALUES
4810 '
4820 C1=0: C2=0: C3=0              ' INITIALIZE SLANT RANGE SUM
4830 BAD(1)=0: BAD(2)=0: BAD(3)=0   ' INITIALIZE BAD DATA COUNTER
4840 CNT1=0: CNT2=0: CNT3=0        ' INITIALIZE NUMBER OF SLANT RANGES
4850 '
4860 FOR I=1 TO NUMSPAR             'STEP THROUGH EACH SLANT RANGE
4870 '
4880 ' TEST EACH SLANT RANGE. IF LESS THAN MAX VALUE OF 245 CM. ADD TO SUM.
4890 ' IF A VALUE IS GREATER THAN 245 CM., INCREMENT BAD COUNTER AND IGNORE
4900 ' THE BAD DATA.  IF 5 BAD VALUES ARE DETECTED, THE MICROPHONE IN ERROR
4910 ' MIGHT BE BLOCKED, AN ERROR MESSAGE IS DISPLAYED AND SRINP IS RECALLED.
4920 '
4930    IF SLANT(I,1)<245 THEN C1=C1+SLANT(I,1): CNT1=CNT1+1: ELSE BAD(1)=BAD(1)+1
4940 '
4960 '
4970    IF SLANT(I,2)<245 THEN C2=C2+SLANT(I,2): CNT2=CNT2+1: ELSE BAD(2)=BAD(2)+1
4980 '
5000 '
5010    IF SLANT(I,3)<245 THEN C3=C3+SLANT(I,3): CNT3=CNT3+1: ELSE BAD(3)=BAD(3)+1
5020 '
5040 '
5050 NEXT I    ' TEST NEXT SET OF SLANT RNAGES
5060 '
5070 ' CALCULATE THE AVERAGE SLANT RANGE VALUES
5080 SMEAN(1)=C1/CNT1: SMEAN(2)=C2/CNT2: SMEAN(3)=C3/CNT3
5090 '
5100 ' CALCULATE STANDARD DEVIATIONS OF SLANT RANGE VALUES TO DETERMINE IF
5110 ' THERE IS UNACCEPTABLE VARIATION IN THE DATA, IE. A AIR DISTURBANCE.
5120 '
5130 C1=0: C2=0: C3=0              ' INITIALIZE SLANT RANGE SUM
5140 CNT1=0: CNT2=0: CNT3=0        ' INITIALIZE NUMBER OF SLANT RANGES
5150 '
5160 FOR I=1 TO NUMSPAR             ' STEP THROUGH EACH SLANT RANGE
5170 '
5180    IF SLANT(I,1)<245 THEN C1=C1+(SLANT(I,1)-SMEAN(1))^2: CNT1=CNT1+1
5190    IF SLANT(I,2)<245 THEN C2=C2+(SLANT(I,2)-SMEAN(2))^2: CNT2=CNT2+1
5200    IF SLANT(I,3)<245 THEN C3=C3+(SLANT(I,3)-SMEAN(3))^2: CNT3=CNT3+1
5210 '
5220 NEXT I    ' TEST NEXT SET OF SLANT RNAGES
```

```
5230 '
5240 ' LET N1-3 EQUAL THE TOTAL NUMBER OF VALUES-1
5250 N1=CNT1-1: N2=CNT2-1: N3=CNT3-1
5260 '
5270 ' CALCULATE STANDARD DEVIATIONS
5280 SD(1)=(C1/N1)^.5: SD(2)=(C2/N2)^.5: SD(3)=(C3/N3)^.5
5290 '
5295 GOSUB 8000 'CALL SUBROUTINE STATISTICS LOG
5300 ' ACCEPTABILITY.
5310 '
5320 SDLIMIT=.1      ' SET STANDARD DEVIATION LIMIT
5330 '
5331 IF BAD(1)>=5 THEN PRINT,BAD(1),"SLANTRANGES BETWEEN SPARKGAP",SGAP+1," AND MIKE",MICE
     (MNOT,1)," EXCEEDED 245cm": PRINT"TRY AGAIN": GOTO 4170
5332 IF BAD(2)>=5 THEN PRINT,BAD(2),"SLANTRANGES BETWEEN SPARKGAP",SGAP+1," AND MIKE",MICE
     (MNOT,2)," EXCEEDED 245cm": PRINT"TRY AGAIN": GOTO 4170
5333 IF BAD(3)>=5 THEN PRINT,BAD(3),"SLANTRANGES BETWEEN SPARKGAP",SGAP+1," AND MIKE",MICE
     (MNOT,3)," EXCEEDED 245cm": PRINT"TRY AGAIN": GOTO 4170
5340 IF SD(1)>SDLIMIT THEN PRINT"TOO MUCH VARIANCE IN SLANTRANGES BETWEEN SPARKGAP",SGAP+1,
     " AND MIKE",MICE(MNOT,1): PRINT"TRY AGAIN": GOTO 4170
5350 IF SD(2)>SDLIMIT THEN PRINT"TOO MUCH VARIANCE IN SLANTRANGES BETWEEN SPARKGAP",SGAP+1,
     " AND MIKE",MICE(MNOT,2): PRINT"TRY AGAIN": GOTO 4170
5360 IF SD(3)>SDLIMIT THEN PRINT"TOO MUCH VARIANCE IN SLANTRANGES BETWEEN SPARKGAP",SGAP+1,
     " AND MIKE",MICE(MNOT,3): PRINT"TRY AGAIN": GOTO 4170
5370 '
5380 ' ADD THE COUNTER DELAY EQUIVALENT OF 4.45 CM. TO EACH MEAN SLANT RANGE
5390 SMEAN(1)=SMEAN(1)+4.45: SMEAN(2)=SMEAN(2)+4.45: SMEAN(3)=SMEAN(3)+4.45
5400 '
5410 SP=SGAP+1      ' INCREMENT SRMEAN ARRAY POINTER
5420 '
5430 'STORE MEAN VALUES IN ARRAY SRMEAN(MIKE#,SPARK#)
5440 '
5450 SRMEAN(1,SP)=SMEAN(1): SRMEAN(2,SP)=SMEAN(2): SRMEAN(3,SP)=SMEAN(3)
5460 '
5470 NEXT SGAP      ' FIRE NEXT SPARK GAP
5480 '
5490 SFLAG=0        ' RESET SFLAG TO 0
5500 '
5510 RETURN
5520 '
5530 ' SUBROUTINE: NEWTON
5540 '
5550 ' THIS SUBROUTINE SOLVES 3 SETS OF 3 NONLINEAR EQUATIONS FOR 3 UNKNOWNS.
5560 ' USING AN ITERATIVE NEWTON'S METHOD.  DEPENDING ON THE VALUE OF
5570 ' NFLAG, CW1 IS SET TO ZERO OR TO CW SUCH THAT EQUATIONS 6.15 OR 6.13
5580 ' CAN BE SOLVED, RESPECTIVELY.
5590 ' THE OUTPUT IS THE COORDINATES STORED IN ARRAY NSOL.
5600 '
5610 ' INPUTS: FX(POINT,COORD)- FIXED COORDINATES;
5620 '         DIST(POINT,3) - DISTANCES BETWEEN POINTS;
5630 '         CW - COSINE OF ANGLE W, S2-S1-S3 (SPARK GAPS);
5640 '         NFLAG - 1 TO SOLVE EQN. 6.15, 0 TO SOLVE EQN. 6.13
5650 ' OUTPUT: NSOL(POINT,COORD) - COORDINATE SOLUTIONS
5660 ' SUBROUTINE NEEDED: INVERSE
5670 '
5680 ' EVALUATE THE STATUS OF NFLAG AND SET APPROPRIATE VARIABLES.
5690 ' EQNUM - NUMBER OF SETS OF EQUATIONS TO BE SOLVED;
5700 ' INIT - INITIAL VALUES FOR ITERATIVE SOLUTION.
5710 '
5720 IF NFLAG=0 THEN CW1=0: EQNUM=3: INIT=15
5730 IF NFLAG=1 THEN CW1=CW: EQNUM=1: INIT=-30
5740 IF NFLAG=2 THEN CW1=0: EQNUM=1: INIT=10
5750 '
5760 ' SET ITERATIVE TOLERANCE AND NUMBER OF ITERATIVE STEPS
5770 E=.001
5780 ITERNUM = 35
5790 ' LOOP THROUGH EACH SET OF EQUATIONS UP TO EQNUM
5800 FOR MK=1 TO EQNUM
5810 '
5820 ' STORE INITIAL SOLUTIONS
5830   FOR COORD=1 TO 3          ' STEP THROUGH X,Y,Z
5840     M#(1,COORD)=ITER         ' STORE INITAL SOLUTION
5850   NEXT COORD                 ' NEXT COORDINATE
5860 '
5870 ' LOOP THROUGH UP TO 35 ITERATIONS
5880   FOR ITER=2 TO ITERNUM
5890 '
5900 ' STORE ITER-1 SOLUTION
5910     FOR COORD=1 TO 3         ' STEP THROUGH X,Y,Z
5920       MV#(COORD)=M#(ITER-1,COORD)  ' STORE PREVIOUS SOLUTION
5930     NEXT COORD                ' NEXT COORDINATE
5940 '
5950 ' CALCULATE JACOBIAN MATRIX COEFFICIENTS FROM THE DERIVATIVES OF THE
```

```
5960 ' EQUATIONS.
5970 '
5980   FOR I=1 TO 3
5990     FOR J=1 TO 2
6000       IF J=1 THEN J1=2
6010       IF J=2 THEN J1=1
6020       J#(I,J)=2*(MV#(J)-FX(I,J))+2*CW1*(MV#(J1)-FX(I,J1))
6030     NEXT J
6040     J#(I,3)=2*(MV#(3)-FX(I,3))
6050   NEXT I
6060 '
6070 ' INVERT THE JACOBIAN MATRIX
6080   GOSUB 6420   ' CALL INVERSE
6090 '
6100 ' DETERMINE SOLUTION ITER
6110   FOR I=1 TO 3
6120   F#(I)=(MV#(1)-FX(I,1))^2+(MV#(2)-FX(I,2))^2+(MV#(3)-FX(I,3))^2+2*(MV#(1)-FX(I,1))*
       (MV#(2)-FX(I,2))*CW1-DIST(I,MK)
6130   NEXT I
6140 '
6150   FOR I=1 TO 3
6160     M#(ITER,I)=MV#(I)-I#(I,1)*F#(1)-I#(I,2)*F#(2)-I#(I,3)*F#(3)
6170   NEXT I
6180 '
6190 ' CALCULATE ITERATIVE ERROR AND SEE IF IT IS WITHIN THE SET TOLERANCE TOL
6200   FOR I=1 TO 3
6210     T(I)=ABS(M#(ITER,I)-MV#(I))/ABS(M#(ITER,I))
6220   NEXT I
6230 '
6240 ' IF ERROR IS WITHIN TOL STORE SOLUTION OR CONTINUE TO NEXT ITERATION
6250   IF (T(1)<E) AND (T(2)<E) AND (T(3)<E) THEN 6340
6260 '
6270   NEXT ITER    ' NEXT ITERATION
6280 '
6290 ' IF NO SOLUTION IS REACHED AFTER 35 ITERATIONS PRINT ERROR MESSAGE
6300 ' AND STORE LAST ITERATION.
6310   PRINT "NO SOLUTION FOR POINT #";MK: ITER=35
6311 PRINT"THE RELATIVE ERRORS ARE:"
6312 PRINT"X-COORDINATE:",T(1):PRINT"Y-COORDINATE:",T(2)
6313 PRINT"Z-COORDINATE:",T(3)
6314 PRINT
6315 PRINT"IF YOU WANT TO DO SOME MORE ITERATIONS,ENTER HOW MUCH"
6316 PRINT"MORE, ELSE ENTER '0'";
6317 INPUT  ITERNUM
6318 IF ITERNUM<>0 THEN ITERNUM=ITERNUM+2: GOTO 5870
6319 '
6320 '
6330 ' STORE SOLUTIONS IN ARRAY NSOL
6340   FOR I=1 TO 3
6350     NSOL(MK,I)=M#(ITER,I)
6360   NEXT I
6370 '
6380 NEXT MK        ' NEXT SET OF EQUATIONS
6390 '
6400 RETURN
6410 '
6420 ' FILENAME: INVERSE
6430 '
6440 ' THIS SUBROUTINE INVERTS THE JACOBIAN MATRIX USING THE CROUT ALGORITHM
6450 '
6460 ' INPUT: J#(3,3) - JACOBIAN MATRIX
6470 ' OUTPUT: I#(3,3) - INVERTED MATRIX
6480 '
6490 ' SET INVERSION CRITEREA BY STORING THE IDENTITY MATRIX SOLUTIONS
6500 FOR I=1 TO 3
6510  FOR J=1 TO 3
6520   IF I=J THEN I#(I,J)=1 ELSE I#(I,J)=0
6530  NEXT J
6540 NEXT I
6550 '
6560 TOL#=1E-09      ' SET ZERO TOLERANCE FOR MATRIX SINGULARITY
6570 '
6580 FOR I=1 TO 3    ' SEARCH FOR LARGEST ELEMENT IN A COLUMN
6590   X=-1
6600 '
6610  FOR K=1 TO 3   ' SEARCH BELOW MAIN DIAGONAL
6620   IF ABS(J#(K,I))<=X THEN 6640
6630   Q=K: X=ABS(J#(K,I))     ' Q IS ROW OF LARGEST ELEMENT
6640  NEXT K         ' X IS LARGEST ELEMENT
6650 '
6660 ' TEST FOR SINGULAR MATRIX AND STOP IF NECESSARY
6670 IF X>=0 THEN 6690 ELSE PRINT"SINGULAR MATRIX": STOP
6680 '
```

```
6690  IF I=Q THEN 6790        'INTERCHANGE IF NEEDED
6700 '
6710  FOR J=1 TO 3       ' NO. SWITCH ROWS I AND Q
6720    T=J#(I,J): J#(I,J)=J#(Q,J): J#(Q,J)=T
6730  NEXT J
6740 '
6750  FOR J=1 TO 3
6760    T=I#(I,J): I#(I,J)=I#(Q,J): I#(Q,J)=T  ' SWITCH RIGHT HAND SIDE
6770  NEXT J
6780 '
6790  FOR J=1 TO 3              ' ELIMINATE ON THAT ONE ROW
6800 '
6810    IF I<J THEN M1=I-1 ELSE M1=J-1
6820    S=0                ' FIND INNER PRODUCT OF ROW I AND COLUMN J = S
6830 '
6840    FOR K=1 TO M1
6850      S=S+J#(I,K)*J#(K,J)
6860    NEXT K
6870 '
6880    J#(I,J)=J#(I,J)+S
6890 ' STOP HERE IF BELOW MAIN DIAGONAL. CHECK FOR SINGULARITY ELSE NORMALIZE
6900    IF I>=J THEN 6950
6910 '
6920    IF ABS(J#(I,I))<TOL# THEN PRINT"SINGULAR MATRIX": STOP
6930 '
6940    J#(I,J)=-J#(I,J)/J#(I,I)    'ELSE NORMALIZE
6950  NEXT J       ' NEXT COLUMN
6960 NEXT I        ' NEXT COLUMN
6970 '
6980 'REDUCE RIGHT HAND SIDE
6990 '
7000 FOR J=1 TO 3        ' FOR EACH SET OF CONSTANTS
7010  FOR I=1 TO 3       ' LOOK DOWN EACH COLUMN
7020    S=0
7030 '
7040    FOR K=1 TO I-1
7050      S=S+J#(I,K)*I#(K,J) ' TAKE PARTIAL INNER PRODUCT
7060    NEXT K
7070 '
7080    I#(I,J)=-(I#(I,J)+S)/J#(I,I)
7090 '
7100  NEXT I
7110 '
7120  FOR I=3 TO 1 STEP -1   ' WORK BACK UP COLUMN
7130    S=0                  ' TAKE PARTIAL INNER PRODUCTS
7140 '
7150    FOR K=I+1 TO 3
7160      S=S+J#(I,K)*I#(K,J)
7170    NEXT K
7180 '
7190    I#(I,J)=-I#(I,J)+S
7200 '
7210  NEXT I
7220 NEXT J
7230 '
7240 RETURN
7250 '
7260 ' SUBROUTINE: STORE-SIT
7270 '
7280 ' THIS SUBROUTINE STORES THE OBLIQUE SPARK GAP COORDINATES OF THE FOCAL,
7290 ' NORMAL AND ORIENTATION POINTS IN FILE "SIT".
7300 '
7310 OPEN "SIT" FOR OUTPUT AS #1        ' OPEN FILE SIT TO STORE COORDINATES
7311 PRINT #1, MNOT
7320  FOR PNT=1 TO 3                    ' STEP THROUGH EACH POINT
7330    FOR COORD=1 TO 3                ' STEP THROUGH X,Y,Z
7340      PRINT #1,FOCAL(PNT,COORD)     ' WRITE THE COORDINATE TO THE FILE
7350    NEXT COORD                      ' NEXT COORDINATE
7360  NEXT PNT                          ' NEXT POINT
7370 '
7380 CLOSE #1                           ' CLOSE FILE SIT
7390 '
7400 RETURN
7500 '
8000 ' SUBROUTINE: STATISTICAL LOG
8010 '
8012 '
8020 FOR L1 = 1 TO 3
8030 '
8040    FOR L2 = 1 TO 7
8050      CLASS(L2) = 0
8060    NEXT L2
8070 '
```

```
8080      MIN = SLANT(1,L1): MAX = SLANT(1,L1)
8090  '
8100      FOR L2 = 1 TO NUMSPAR
8110          IF SLANT(L2,L1) > 245 THEN GOTO 8210
8120          IF SLANT(L2,L1) > MAX THEN MAX = SLANT(L2,L1)
8130          IF SLANT(L2,L1) < MIN THEN MIN = SLANT(L2,L1)
8140          IF SLANT(L2,L1) >(SMEAN(L1)+.06)THEN CLASS(1)=CLASS(1)+1: GOTO 8210
8150          IF SLANT(L2,L1) >(SMEAN(L1)+.03)THEN CLASS(2)=CLASS(2)+1: GOTO 8210
8160          IF SLANT(L2,L1) >(SMEAN(L1)+.01)THEN CLASS(3)=CLASS(3)+1: GOTO 8210
8170          IF SLANT(L2,L1) >(SMEAN(L1)-.01)THEN CLASS(4)=CLASS(4)+1: GOTO 8210
8180          IF SLANT(L2,L1) >(SMEAN(L1)-.03)THEN CLASS(5)=CLASS(5)+1: GOTO 8210
8190          IF SLANT(L2,L1) >(SMEAN(L1)-.06)THEN CLASS(6)=CLASS(6)+1: GOTO 8210
8200          CLASS(7) = CLASS(7) + 1
8210      NEXT L2
8220  '
8230      IF SFLAG = 1 THEN PRINT#2,"SLANTRANGES BETWEEN SPARKGAP 4 AND MIKE",MICE(MNOT,L1)
8240      IF SFLAG=1 AND SCALL=1 THEN PRINT#2,"FOURTH SPARKGAP FIRED"
8250      IF SFLAG=0 AND SCALL=2 THEN PRINT#2,"FOCUSED ON FOURTH SPARKGAP"
8260      IF SFLAG=0 AND SCALL=3 THEN PRINT#2,"FOCUSED ON GRIDPOINT 1"
8270      IF SFLAG=0 AND SCALL=4 THEN PRINT#2,"FOCUSED ON GRIDPOINT 2"
8280      IF SFLAG=0 AND SCALL=5 THEN PRINT#2,"FOCUSED ON GRIDPOINT 3, LOW POSITION"
8290      IF SFLAG=0 AND SCALL=6 THEN PRINT#2,"FOCUSED ON GRIDPOINT 3, HIGH POSITION"
8300  '
8310      PRINT#2,"SPARKGAP:",SGAP+1," MIKE:",MICE(MNOT,L1)," SPARKS: ",NUMSPAR
8320      PRINT#2,"MEAN: ",SMEAN(L1)," STANDARD DEVIATION: ",SD(L1)
8330      PRINT#2,"SLANTRANGES > 245cm:",BAD(L1)
8340      PRINT#2,"MIN: ",MIN," MAX: ",MAX
8350  '
8360      FOR L2 = 1 TO 7
8370          PRINT #2,CLASS(L2)
8380      NEXT L2
8390      PRINT #2," "
8400  NEXT L1
8410  PRINT #2," "
8420  RETURN
```

*Appendix B*

```
10   '
20   ' APPENDIX C
30   '
40   ' THESIS TITLE: REFERENCE - DISPLAY SYSTEM FOR THE INTEGRATION OF CT
50   ' SCANNING AND THE OPERATING MICROSCOPE
60   '
70   ' FILENAME: REG
80   '
90   ' PROGRAMMER: JOHN F. HATCH
100  ' DATE: AUGUST, 1984
110  '
120  ' NOTE: REFER TO CHAPTER 6 IN THESIS FOR EQUATIONS,
130  '       AND REFERENCE 10 FOR ALGORITHMS.
140  '
150  ' THIS FILE IS THE DRIVER FOR THE REGISTRATION PROCEDURE.
160  '
170  OPTION BASE 1       ' SET THE LOWER ARRAY INDEX TO 1 FOR CONVENIENCE
180  '
190  ' ALLOCATE SPACE FOR ARRAYS
200  ' NOTE: ARRAY NAMES FOLLOWED BY A "#" SIGN ARE DOUBLE PRECISION
210  '
220  DIM J#(3,3)         ' JACOBIAN MATRIX COEFFICIENTS
230  DIM I#(3,3)         ' JACOBIAN MATRIX INVERSE
240  DIM SRMEAN(3,3)     ' MEAN SLANT RANGES
250  DIM SDATA(3,3,3)    ' SLANT RANGE DATA
```

```
260 DIM FOCAL(3,3)    ' FOCAL, NORMAL AND ORIENTATION POINT COORDINATES
270 DIM NSOL(3,3)     ' NEWTON SOLUTIONS
280 DIM FX(3,3)       ' FIXED COORDINATE SYSTEM
290 DIM MV#(3)        ' ITERATION VARIABLE (N-1)
300 DIM M#(100,3)     ' ITERATION VARIABLES
310 DIM SL(3)         ' SLANT RANGE DATA
320 DIM F#(4)         ' ITERATIVE SOLN TO NEWTON
330 DIM DIST(3,3)     ' DISTANCES USED IN NEWTON
340 DIM D(3)          ' DISTANCES USED IN DISTANCE
350 DIM T(3)          ' ITERATION ERRORS
360 DIM MIKE(3,3)     ' MICROPHONE COORDINATES
370 DIM FPOINT(3)     ' FOCAL POINT COORDINATES
380 DIM FPLANE(4)     ' FOCAL PLANE COEFFICIENTS
390 DIM SLANT(150,3)  ' SLANT RANGES
391 DIM CLASS(7)      'CLASSES FOR HISTOGRAM OF SLANTRANGES
392 DIM MICE(4,3)     'MICROPHONE ARRAY
393 DIM SMEAN(3)      'MEAN VALUES OF SLANT RANGES
394 DIM BAD(3)        '# OF SLANTRANGES > 245 cm
395 DIM SD(3)         'STANDARD DEVIATIONS OF SLANTRANGES
396 MICE(1,1)=2: MICE(1,2)=4: MICE(1,3)=3: MICE(2,1)=1: MICE(2,2)=3
397 MICE(2,3)=4: MICE(3,1)=4: MICE(3,2)=2: MICE(3,3)=1: MICE(4,1)=3
398 MICE(4,2)=1: MICE(4,3)=2
399 STFL = 1          'STATISTICS FLAG
400 OPEN "REG.LOG" FOR OUTPUT AS #2
410 ' MEASURED DISTANCES BETWEEN SPARK GAPS IN CM.
420 S12=30.041        ' SPARK GAP 1 - SPARK GAP 2
430 S23=29.995        ' SPARK GAP 2 - SPARK GAP 3
440 S31=29.657        ' SPARK GAP 3 - SPARK GAP 1
450 '
460 CW=(S12^2+S31^2-S23^2)/(2*S12*S31)    ' COSINE OF ANGLE W, S2-S1-S3 EQ. 6.1
470 S2W=1-CW*CW                            ' SINE SQUARED OF ANGLE W, S2-S1-S3
480 '
490 OPEN "RSLANT.MEA" FOR OUTPUT AS #3
710 GOSUB 7230
711 PRINT "MICROPHONE #",MNOT," IS CURRENTLY SHUT OFF."
712 PRINT "IF ANOTHER MICROPHONE SHOULD BE SHUT OFF, FPL HAS TO BE"
713 PRINT "DONE FOR THE NEW CONFIGURATION."
714 PRINT "ANSWER 'Y' IF YOU NEED TO DO FPL, 'N' IF NOT";
715 INPUT ANSWER$
716 IF ANSWER$ = "Y" THEN STOP
717 IF ANSWER$ = "N" THEN GOTO 720 ELSE GOTO 711
720 '
721 PRINT
722 PRINT"HOW MANY SPARKS DO YOU WANT TO FIRE (MAX. 150)";
723 INPUT NUMSPAR
724 IF (NUMSPAR>150) OR (NUMSPAR<1) THEN GOTO 721
725 PRINT #3, MNOT
726 FOR I=1 TO 4
727   PRINT #3, NUMSPAR
728 NEXT I
760 PRINT
770 PRINT "TURN ON DIGITIZER AND SPARK GAP MULTIPLEXER."
780 PRINT
790 '
800 ' IF COMPUTER FAILS AFTER REGISTRATION RECALL MICROPHONE COORDINATES
810 PRINT"DID THE COMPUTER FAIL AFTER FOCUSING ON THE FIDUCIALS, YES (Y)"
820 PRINT"OR NO (N)? ANSWER 'NO' TO THIS QUESTION IF THIS IS THE FIRST TIME"
830 PRINT"RUNNING THIS PROGRAM.";
840 INPUT FAIL$
850 '
860 HFLAG=0
870 IF FAIL$="Y" THEN GOSUB 7540: GOTO 900
880 IF FAIL$<>"N" THEN GOTO 810
890 '
900 CFLAG=0    ' SET CALIBRATION FLAG
910 '
920 PRINT
930 PRINT "DO YOU WANT TO TEST THE REGISTRATION SYSTEM (Y OR N)";
940 INPUT TST$
950 PRINT
960 PRINT"PRESS CTRL BREAK TO STOP AT ANY TIME"
970 PRINT
980 '
990 IF TST$="Y" THEN GOSUB 6470: GOTO 920    ' CALL TEST
1000 IF TST$<>"N" THEN GOTO 920
1010 '
1020 ' DETERMINE MICROPHONE COORDINATES IN CT COORDINATE SYSTEM
1030 '
1040 IF HFLAG=1 THEN GOTO 1080
1050 '
1060 GOSUB 4220    ' CALL REGISTER
1070 '
1080 PRINT
```

```
1090 PRINT " BEGIN PROCEDURE - BREAK TO STOP"
1100 PRINT
1110 '
1120 ' STORE MICROPHONE COORDINATES (IN ARRAY MIKE) IN ARRAY FX FOR NEWTON
1130 '
1140 FOR MK=1 TO 3                    ' STEP THROUGH EACH MICROPHONE
1150  FOR COORD=1 TO 3                ' STEP THROUGH X,Y,Z
1160   FX(MK,COORD)=MIKE(MK,COORD)    ' STORE COORDINATE
1170  NEXT COORD                      ' NEXT COORDINATE
1180 NEXT MK                          ' NEXT MICROPHONE
1190 '
1200 ' CALL SUBROUTINE SLICE TO TAKE THE COORDINATES OF THE MICROPHONES IN CT
1210 ' COORDINATES AND THE SLANT RANGE DISTANCES AND CALCULATE THE COORDINATES
1220 ' OF THE FOCAL POINT, EQUATION OF THE FOCAL PLANE AND THE THREE DIRECTION
1230 ' COSINES.
1240 '
1250  GOSUB 5080     ' CALL SLICE
1260 '
1270 ' DISPLAY THE COORDINATES OF THE FOCAL POINT, THE EQUATION OF THE FOCAL
1280 ' PLANE AND THE THREE DIRECTION COSINES.
1290 '
1300  PRINT
1310  PRINT"FOCAL POINT COORDINATES (X,Y,Z)"
1320  PRINT
1330  PRINT FPOINT(1),FPOINT(2),FPOINT(3)
1340  PRINT
1350  PRINT"FOCAL PLANE COEFFICIENTS (A,B,C,D)"
1360  PRINT
1370  PRINT FPLANE(1),FPLANE(2),FPLANE(3),FPLANE(4)
1380  PRINT
1390  PRINT"X DIRECTION COSINE=";DCOSX
1400  PRINT"Y DIRECTION COSINE=";DCOSY
1410  PRINT"Z DIRECTION COSINE=";DCOSZ
1411 '
1412 CLOSE #2
1413 CLOSE #3
1420 '
1430 GOSUB 7850        ' CALL OUTPUT-RECI.DAT
1440 '
1441 PRINT
1442 PRINT"*** DON'T FORGET TO RENAME FILE REG.LOG TO AVOID OVERWRITING ***"
1443 PRINT"RENAME FILE RSLANT.MEA"
1450 STOP
1460 '
1470 ' SUBROUTINE: SRINP
1480 '
1490 ' THIS FILE OPENS THE RS-232 PORT FOR DIGITIZER COMMUNICATIONS,
1500 ' CONTROLS THE SPARK GAP MULTIPLEXER, STORES THE SLANT RANGES
1510 ' IN AN ARRAY, AND DETERMINES THE STANDARD DEVIATIONS AND MEANS.
1520 '
1530 ' INPUT: MNOT - IGNORED MICROPHONE
1540 ' OUTPUT: SRMEAN(MIKE,SKGAP) - AVERAGE SLANT RANGES FOR EACH SPARK GAP
1550 '
1560 PRINT
1570 PRINT "*****PRESS ANY KEY WHEN FOCUSED/READY*****"
1580 PRINT
1590 '
1600 ' PAUSE UNTIL ANY KEY IS DEPRESSED
1610 P$=INKEY$: IF P$="" THEN 1610
1620 '
1630 FOR SGAP=0 TO 2    ' SET MULTIPLEXER THROUGH PARALLEL PORT
1640 ' CHANGE SGAP TO SGAP1 FOR PROPER MULTIPLEXER SEQUENCING
1650  IF SGAP=0 THEN SGAP1=0
1660  IF SGAP=1 THEN SGAP1=2
1670  IF SGAP=2 THEN SGAP1=1
1680 '
1690 ' WRITE THE BINARY CODE FOR SGAP1 TO THE PARALLEL PORT ADDRESS 3BC HEX
1700  OUT &H3BC,SGAP1
1710 '
1720 ' OPEN RS-232 PORT, SET BAUD RATE AND PARITY
1730  OPEN "COM1:9600,0,7,1" AS #1
1740 '
1750  FLAG=1           ' INITIALIZE CHARACTER FLAG
1760  WHILE FLAG       ' SEARCH CHARACTER INPUT FOR ASCII LINE FEED IF FLAG=1
1770   S$=INPUT$(1,#1)
1780    IF ASC(S$)=10 THEN FLAG=0 ELSE FLAG=1
1790  WEND
1800 '
1810  W$=INPUT$(26,#1)    ' IGNORE FIRST VALUES (FROM LAST SLANT RANGES)
1820 '
1840  FOR I=1 TO NUMSPAR   ' FIRE EACH SPARK GAP 150 TIMES
1850 '
1860 ' MONITOR COMM BUFFER, IF >40 CHARACTERS IN BUFFER TURN OFF DIGITIZER
```

```
1870 ' BY WRITING BINARY CODE 10 TO ADDRESS 3FC HEX - THE RS-232 PORT
1880 '
1890    IF LOC(1)>40 THEN OUT &H3FC,10 ELSE OUT &H3FC,11
1900 '
1910 ' INPUT SLANT RANGES AND INSERT DECIMAL POINTS TO READ DISTANCES IN CM.
1920 '
1930    A$=INPUT$(26,#1)     ' INPUT 26 CHARACTER STRING (4 SLANT RANGES)
1940 '
1950    C$=MID$(A$,1,6):  CL$=LEFT$(C$,3):  CR$=RIGHT$(C$,3):  CC$=CL$+"."+CR$
1960    D$=MID$(A$,7,6):  DL$=LEFT$(D$,3):  DR$=RIGHT$(D$,3):  DD$=DL$+"."+DR$
1970    E$=MID$(A$,13,6): EL$=LEFT$(E$,3):  ER$=RIGHT$(E$,3):  EE$=EL$+"."+ER$
1980    F$=MID$(A$,19,6): FL$=LEFT$(F$,3):  FR$=RIGHT$(F$,3):  FF$=FL$+"."+FR$
1990 '
2000 ' STORE THE VALUE OF EACH CHARACTER STRING FOR EACH SLANT RANGE IN G1-4
2010    G1=VAL(CC$): G2=VAL(DD$): G3=VAL(EE$): G4=VAL(FF$)
2020 '
2030 ' IGNORE SLANT RANGE DATA FROM MICROPHONE MNOT AND STORE REMAINING
2040 ' SLANT RANGES IN P1-3
2050 '
2060    IF MNOT=1 THEN P1=G3: P2=G4: P3=G2
2070    IF MNOT=2 THEN P1=G1: P2=G3: P3=G4
2080    IF MNOT=3 THEN P1=G4: P2=G2: P3=G1
2090    IF MNOT=4 THEN P1=G3: P2=G1: P3=G2
2100 '
2110 ' STORE SLANT RANGES IN ARRAY SLANT
2120    SLANT(I,1)=P1: SLANT(I,2)=P2: SLANT(I,3)=P3
2130 '
2140 NEXT I    ' GET NEXT SET OF FOUR SLANT RANGES
2150 '
2160 CLOSE #1  ' SUPPRESS DIGITIZER COMMUNICATION
2170 '
2180 ' CALCULATE MEAN SLANT RANGE VALUES
2190 '
2200 C1=0: C2=0: C3=0              ' INITIALIZE SLANT RANGE SUM
2210 BAD(1)=0: BAD(2)=0: BAD(3)=0  ' INITIALIZE BAD DATA COUNTER
2220 CNT1=0: CNT2=0: CNT3=0        ' INITIALIZE NUMBER OF SLANT RANGES
2230 '
2240 FOR I=1 TO NUMSPAR            'STEP THROUGH EACH SLANT RANGE
2250 '
2260 ' TEST EACH SLANT RANGE. IF LESS THAN MAX VALUE OF 245 CM. ADD TO SUM.
2270 ' IF A VALUE IS GREATER THAN 245 CM., INCREMENT BAD COUNTER AND IGNORE
2280 ' THE BAD DATA.  IF 5 BAD VALUES ARE DETECTED, THE MICROPHONE IN ERROR
2290 ' MIGHT BE BLOCKED, AN ERROR MESSAGE IS DISPLAYED AND SHINP IS RECALLED.
2300 '
2310 IF SLANT(I,1)<245 THEN C1=C1+SLANT(I,1): CNT1=CNT1+1: ELSE BAD1=BAD1+1
2320 '
2340 '
2350 IF SLANT(I,2)<245 THEN C2=C2+SLANT(I,2): CNT2=CNT2+1: ELSE BAD2=BAD2+1
2360 '
2380 '
2390 IF SLANT(I,3)<245 THEN C3=C3+SLANT(I,3): CNT3=CNT3+1: ELSE BAD3=BAD3+1
2400 '
2420 '
2430 NEXT I    ' TEST NEXT SET OF SLANT RNAGES
2440 '
2450 ' CALCULATE THE AVERAGE SLANT RANGE VALUES
2460 SMEAN(1)=C1/CNT1: SMEAN(2)=C2/CNT2: SMEAN(3)=C3/CNT3
2470 '
2480 ' CALCULATE STANDARD DEVIATIONS OF SLANT RANGE VALUES TO DETERMINE IF
2490 ' THERE IS UNACCEPTABLE VARIATION IN THE DATA, IE. A AIR DISTURBANCE.
2500 '
2510 C1=0: C2=0: C3=0              ' INITIALIZE SLANT RANGE SUM
2520 CNT1=0: CNT2=0: CNT3=0        ' INITIALIZE NUMBER OF SLANT RANGES
2530 '
2540 FOR I=1 TO NUMSPAR            ' STEP THROUGH EACH SLANT RANGE
2550 '
2560 IF SLANT(I,1)<245 THEN C1=C1+(SLANT(I,1)-SMEAN(1))^2: CNT1=CNT1+1
2570 IF SLANT(I,2)<245 THEN C2=C2+(SLANT(I,2)-SMEAN(2))^2: CNT2=CNT2+1
2580 IF SLANT(I,3)<245 THEN C3=C3+(SLANT(I,3)-SMEAN(3))^2: CNT3=CNT3+1
2590 '
2600 NEXT I    ' TEST NEXT SET OF SLANT RNAGES
2610 '
2620 ' LET N1-3 EQUAL THE TOTAL NUMBER OF VALUES-1
2630 N1=CNT1-1: N2=CNT2-1: N3=CNT3-1
2640 '
2650 ' CALCULATE STANDARD DEVIATIONS
2660 SD(1)=(C1/N1)^.5: SD(2)=(C2/N2)^.5: SD(3)=(C3/N3)^.5
2670 GOSUB 9000 'CALL SUBROUTINE STATISTICAL LOG
2680 ' COMPARE STANDARD DEVIATIONS TO SDLIMIT TO DETERMINE SLANT RANGE
2690 ' ACCEPTABILITY.
2700 '
2710 SDLIMIT=.1     ' SET STANDARD DEVIATION LIMIT
2720 '
```

```
2721 IF BAD(1)>=5 THEN PRINT,BAD(1),"SLANTRANGES BETWEEN SPARKGAP",SGAP+1," AND MIKE",MICE
     (MNOT,1)," EXCEEDED 245cm": PRINT"TRY AGAIN": GOTO 1570
2722 IF BAD(2)>=5 THEN PRINT,BAD(2),"SLANTRANGES BETWEEN SPARKGAP",SGAP+1," AND MIKE",MICE
     (MNOT,2)," EXCEEDED 245cm": PRINT"TRY AGAIN": GOTO 1570
2723 IF BAD(3)>=5 THEN PRINT,BAD(3),"SLANTRANGES BETWEEN SPARKGAP",SGAP+1," AND MIKE",MICE
     (MNOT,3)," EXCEEDED 245cm": PRINT"TRY AGAIN": GOTO 1570
2730 IF SD(1)>SDLIMIT THEN PRINT"TOO MUCH VARIANCE IN SLANTRANGES BETWEEN SPARKGAP",SGAP+1,
     " AND MIKE",MICE(MNOT,1): PRINT"TRY AGAIN": GOTO 1570
2740 IF SD(2)>SDLIMIT THEN PRINT"TOO MUCH VARIANCE IN SLANTRANGES BETWEEN SPARKGAP",SGAP+1,
     " AND MIKE",MICE(MNOT,2): PRINT"TRY AGAIN": GOTO 1570
2750 IF SD(3)>SDLIMIT THEN PRINT"TOO MUCH VARIANCE IN SLANTRANGES BETWEEN SPARKGAP",SGAP+1,
     " AND MIKE",MICE(MNOT,3): PRINT"TRY AGAIN": GOTO 1570
2760 '
2770 ' ADD THE COUNTER DELAY EQUIVALENT OF 4.45 CM. TO EACH MEAN SLANT RANGE
2780 SMEAN(1)=SMEAN(1)+4.45: SMEAN(2)=SMEAN(2)+4.45: SMEAN(3)=SMEAN(3)+4.45
2790 '
2800 SP=SGAP+1        ' INCREMENT SRMEAN ARRAY POINTER
2810 '
2820 'STORE MEAN VALUES IN ARRAY SRMEAN(MIKE#,SPARK#)
2830 '
2840 SRMEAN(1,SP)=SMEAN(1): SRMEAN(2,SP)=SMEAN(2): SRMEAN(3,SP)=SMEAN(3)
2850 '
2860 NEXT SGAP     ' FIRE NEXT SPARK GAP
2870 '
2880 RETURN
2890 '
2900 ' SUBROUTINE. DISTANCE
2910 '
2920 ' THIS SUBROUTINE DETERMINES THE DISTANCE BETWEEN TWO POINTS IN OBLIQUE
2930 ' SPARK GAP COORDINATES.
2940 '
2950 ' INPUTS. FOCAL(POINT,COORD) - OBLIQUE SPARK GAP COORDINATES OF FOCAL,
2960 '         NORMAL AND ORIENTATION POINTS;
2970 '         SL(POINT) - SLANT RANGE DISTANCES FOR EACH POINT;
2980 '         CW - COSINE OF ANGLE W, S2-S1-S3 (SPARK GAPS);
2990 '         S2W - SINE OF ANGLE W SQUARED)
3000 '         PFLAG - FLAG TO INDICATE REGISTRATION PROCEDURE
3010 ' OUTPUT: D(POINT) - DISTANCES FROM FOCAL, NORMAL AND ORIENTATION POINTS
3020 '
3030 ' POINT 1
3040 ' CALCULATE PROJECTIONS OF SLANT 1 ON X AND Y SPARK AXES
3050 '
3060 XP1=(SL(1)^2+S31^2-SL(3)^2)/(2*S31)       ' EQN. 6.3
3070 YP1=(SL(1)^2+S12^2-SL(2)^2)/(2*S12)       ' EQN. 6.4
3080 '
3090 ' CALCULATE OBLIQUE COORDINATES OF POINT 1
3100 '
3110 X1=(XP1-YP1*CW)/S2W                       ' EQN. 6.8
3120 Y1=(YP1-XP1*CW)/S2W                       ' EQN. 6.9
3130 Z1=(SL(1)^2-X1^2-Y1^2-2*X1*Y1*CW)^.5      ' EQN. 6.12
3140 '
3150 ' POINT 2
3160 '
3170 ' FOR REGISTRATION PROCEDURE, ONLY THE FOCAL POINT IS NEEDED SO
3180 ' PTS=1.  THIS IS DETERMINED BY PFLAG.
3190 '
3200 IF PFLAG=1 THEN PTS=1 ELSE PTS=3
3210 '
3220 FOR I=1 TO PTS  ' STEP THROUGH FOCAL, NORMAL AND ORIENT. POINT COORDS.
3230 '
3240 ' RECALL FOCAL, NORMAL AND ORIENTATION POINT COORDINATES
3250 '
3260 X2=FOCAL(I,1)
3270 Y2=FOCAL(I,2)
3280 Z2=FOCAL(I,3)
3290 '
3300 ' CALCULATE DISTANCE D USING OBLIQUE DISTANCE FORMULA, EQN. 6.14
3310 '
3320 D(I)=(X2-X1)^2+(Y2-Y1)^2+(Z2-Z1)^2+2*(X2-X1)*(Y2-Y1)*CW
3330 '
3340 NEXT I
3350 '
3360 RETURN
3370 '
3380 ' FILENAME: INVERSE
3390 '
3400 ' THIS SUBROUTINE INVERTS THE JACOBIAN MATRIX USING THE CROUT ALGORITHM
3410 '
3420 ' INPUT: J#(3,3) - JACOBIAN MATRIX
3430 ' OUTPUT: I#(3,3) - INVERTED MATRIX
3440 '
3450 ' SET INVERSION CRITEREA BY STORING THE IDENTITY MATRIX SOLUTIONS
3460 FOR I=1 TO 3
```

```
3470   FOR J=1 TO 3
3480     IF I=J THEN I#(I,J)=1 ELSE I#(I,J)=0
3490   NEXT J
3500 NEXT I
3510 '
3520 TOL#=1E-09        ' SET ZERO TOLERANCE FOR MATRIX SINGULARITY
3530 '
3540 FOR I=1 TO 3     ' SEARCH FOR LARGEST ELEMENT IN A COLUMN
3550   X=-1
3560 '
3570   FOR K=I TO 3    ' SEARCH BELOW MAIN DIAGONAL
3580     IF ABS(J#(K,I))<=X THEN 3600
3590     Q=K: X=ABS(J#(K,I))    ' Q IS ROW OF LARGEST ELEMENT
3600   NEXT K          ' X IS LARGEST ELEMENT
3610 '
3620 ' TEST FOR SINGULAR MATRIX AND STOP IF NECESSARY
3630   IF X>=0 THEN 3650 ELSE PRINT"SINGULAR MATRIX": STOP
3640 '
3650   IF I=Q THEN 3750     'INTERCHANGE IF NEEDED
3660 '
3670   FOR J=1 TO 3        ' NO. SWITCH ROWS I AND Q
3680     T=J#(I,J): J#(I,J)=J#(Q,J): J#(Q,J)=T
3690   NEXT J
3700 '
3710   FOR J=1 TO 3
3720     T=I#(I,J): I#(I,J)=I#(Q,J): I#(Q,J)=T  ' SWITCH RIGHT HAND SIDE
3730   NEXT J
3740 '
3750   FOR J=1 TO 3              ' ELIMINATE ON THAT ONE ROW
3760 '
3770     IF I<J THEN M1=I-1 ELSE M1=J-1
3780     S=0              ' FIND INNER PRODUCT OF ROW I AND COLUMN J  = S
3790 '
3800     FOR K=1 TO M1
3810       S=S+J#(I,K)*J#(K,J)
3820     NEXT K
3830 '
3840     J#(I,J)=J#(I,J)+S
3850 ' STOP HERE IF BELOW MAIN DIAGONAL, CHECK FOR SINGULARITY ELSE NORMALIZE
3860     IF I>=J THEN 3910
3870 '
3880     IF ABS(J#(I,I))<TOL# THEN PRINT"SINGULAR MATRIX": STOP
3890 '
3900     J#(I,J)=-J#(I,J)/J#(I,I)     'ELSE NORMALIZE
3910   NEXT J         ' NEXT COLUMN
3920 NEXT I           ' NEXT COLUMN
3930 '
3940 'REDUCE RIGHT HAND SIDE
3950 '
3960 FOR J=1 TO 3       ' FOR EACH SET OF CONSTANTS
3970   FOR I=1 TO 3     ' LOOK DOWN EACH COLUMN
3980     S=0
3990 '
4000     FOR K=1 TO I-1
4010       S=S+J#(I,K)*I#(K,J)  ' TAKE PARTIAL INNER PRODUCT
4020     NEXT K
4030 '
4040     I#(I,J)=-(I#(I,J)+S)/J#(I,I)
4050 '
4060   NEXT I
4070 '
4080   FOR I=3 TO 1 STEP -1   ' WORK BACK UP COLUMN
4090     S=0                  ' TAKE PARTIAL INNER PRODUCTS
4100 '
4110     FOR K=I+1 TO 3
4120       S=S+J#(I,K)*I#(K,J)
4130     NEXT K
4140 '
4150     I#(I,J)=-I#(I,J)+S
4160 '
4170   NEXT I
4180 NEXT J
4190 '
4200 RETURN
4210 '
4220 ' SUBROUTINE: REGISTER
4230 '
4240 ' THIS SUBROUTINE CALCULATES THE COORDINATES OF THE THREE MICROPHONES
4250 ' IN THE CT COORDINATE SYSTEM AND STORES THEM IN FILE MIKE.
4260 '
4270 ' INPUT: FOCAL(1,COORD) - OBLIQUE SPARK GAP COORDINATES OF FOCAL POINT
4280 ' OUTPUT: MIKE(MK,AX) - CT COORDINATES OF MICROPHONES
```

```
4290 ' SUBROUTINES NEEDED: SRINP, NEWTON
4300 '
4310 PFLAG=1      ' SET FOCAL POINT ONLY FLAG FOR SUBROUTINE DISTANCE
4320 '
4330 ' COLLECT THE FIDUCIAL DATA IF NECESSARY ELSE READ THE
4340 ' DATA FROM THE FILE FIDUCIALS
4350 '
4360 ' FIND OUT IF THE FIDUCIAL POSITION HAS BEEN ALTERED SINCE THE
4370 ' LAST TIME THIS PROGRAM WAS EXECUTED.
4380 PRINT
4390 PRINT "THE FIDUCIALS MUST BE RESET FOR A NEW PATIENT(POSITION)"
4400 PRINT "DO YOU WANT TO RESET THE FIDUCIALS (Y OR N)";
4410 INPUT RESFID$
4420 IF RESFID$="Y" THEN STFL=2: GOSUB 8030: GOTO 4440
4430 IF RESFID$="N" THEN STFL=3: GOSUB 8310: ELSE GOTO 4380
4440 '
4450 '
4460 PRINT
4470 PRINT"CALCULATING MICROPHONE COORDINATES..."
4480 PRINT
4490 ' CALCULATE DISTANCES BETWEEN MICROPHONES AND FIDUCIALS
4500 '
4510 FOR FID=1 TO 3                ' STEP THROUGH EACH FIDUCIAL
4520  FOR MK=1 TO 3                ' STEP THROUGH EACH MICROPHONE
4530   FOR SPK=1 TO 3              ' STEP THROUGH EACH SPARK GAP
4540    SL(SPK)=SDATA(FID,MK,SPK)   ' STORE SLANT RANGE DATA IN VECTOR SL
4550   NEXT SPK                    ' NEXT SPARK GAP
4560 '
4570 ' CALCULATE THE DISTANCES BETWEEN THE FIDUCIALS (FOCAL POINT) AND THE
4580 ' MICROPHONES.
4590 '
4600   GOSUB 2900   ' CALL DISTANCE
4610 '
4620 ' STORE DISTANCES TO FOCAL POINT IN ARRAY DIST
4630 '
4640   DIST(FID,MK)=D(1)
4650 '
4660  NEXT MK                      ' NEXT MICROPHONE
4670 NEXT FID                      ' NEXT FIDUCIAL
4680 '
4690 ' IF TESTING THE REGISTRATION PROCEDURE, FIDUCIAL COORDINATES ARE
4700 ' KNOWN SO DO NOT ENTER COORDINATES.
4710 '
4720 IF CFLAG=1 THEN 4810
4730 '
4740 ' ENTER FIDUCIAL COORDINATES
4750 '
4760 PRINT
4770 PRINT "LOADING CT COORDINATES OF THE FIDUCIALS FROM FIDOUT.DAT"
4780 '
4790 GOSUB 7680              'CALL RECALL-FIDOUT.DAT
4800 '
4810 ' CALCULATE MICROPHONE COORDINATES BY SOLVING THREE NONLINEAR EQUATIONS
4820 ' FOR THREE UNKNOWNS USING NEWTONS METHOD.  EQN. 6.15.
4830 '
4840 GOSUB 5730    ' CALL NEWTON
4850 '
4860 ' STORE MICROPHONE COORDINATES IN ARRAY MIKE
4870 '
4880 FOR MK=1 TO 3                ' STEP THROUGH EACH MICROPHONE
4890  FOR COORD=1 TO 3            ' STEP THROUGH X,Y,Z
4900   MIKE(MK,COORD)=NSOL(MK,COORD) ' STORE COORDINATE
4910  NEXT COORD                  ' NEXT COORDINATE
4920 NEXT MK                      ' NEXT MICROPHONE
4930 '
4940 ' STORE CT COORDINATES OF MICROPHONES IN FILE MIKE
4950 '
4960 OPEN "MIKE" FOR OUTPUT AS #1 ' OPEN FILE MIKE FOR OUTPUT
4970  FOR MK=1 TO 3               ' LOOP THROUGH EACH MICROPHONE
4980   FOR COORD=1 TO 3           ' LOOP THROUGH X, Y AND Z
4990    PRINT #1,MIKE(MK,COORD)   ' WRITE EACH VALUE TO THE FILE
5000   NEXT COORD
5010  NEXT MK
5020 CLOSE #1                     ' CLOSE THE FILE
5030 '
5040 PFLAG=0                      ' RESET FOCAL POINT COORDINATE FLAG
5050 '
5060 RETURN
5070 '
5080 ' SUBROUTINE: SLICE
5090 '
5100 ' THIS SUBROUTINE CALCULATES THE CT COORDINATES OF THE FOCAL, NORMAL AND
5110 ' ORIENTATION POINTS TO DEFINE THE FOCAL PLANE.  IT ALSO DETERMINES
```

```
5120 ' THE FOCAL PLANE COEFFICIENTS AND THE THREE DIRECTION COSINES.
5130 '
5140 ' INPUTS: MIKE(MK,AX) - CT COORDINATES OF MICROPHONES;
5150 '         FOCAL(POINT,COORD) - OBLIQUE SPARK GAP COORDINATES OF THE FOCAL,
5160 '         NORMAL AND ORIENTATION POINTS.
5170 ' OUTPUTS: FPOINT(COORD) - FOCAL POINT COORDINATES;
5180 '          FPLANE(COEFF) - FOCAL PLANE COEFFICIENTS;
5190 '          DCOSX - X DIRECTION COSINE OF THE FOCAL - ORIENT. POINT VECTOR
5200 '          DCOSY - Y DIRECTION COSINE OF THE FOCAL - ORIENT. POINT VECTOR
5210 '          DCOSZ - Z DIRECTION COSINE OF THE FOCAL - ORIENT. POINT VECTOR
5220 ' SUBROUTINES NEEDED: SRINP, NEWTON
5230 '
5240 ' GET SLANT RANGES
5250 '
5260 GOSUB 1470      ' CALL SRINP
5261 FOR LOOP1=1 TO 3
5262  FOR LOOP2=1 TO 3
5263   PRINT #3, SRMEAN(LOOP2,LOOP1)
5264  NEXT LOOP2
5265 NEXT LOOP1
5270 '
5280 FOR MK=1 TO 3              ' STEP THROUGH EACH MICROPHONE
5290  FOR SPK=1 TO 3            ' STEP THROUGH EACH SPARK GAP
5300 ' STORE SLANT RANGE DATA IN VECTOR SL
5310   SL(SPK)=SRMEAN(MK,SPK)
5320  NEXT SPK                  ' NEXT SPARK GAP
5330 '
5340  GOSUB 2900 ' CALL DISTANCE
5350 '
5360  FOR PT=1 TO 3             ' STEP THROUGH EACH POINT
5370 ' STORE DISTANCES IN ARRAY
5380   DIST(MK,PT)=D(PT)
5390  NEXT PT                   ' NEXT POINT
5400 NEXT MK                    ' NEXT MICROPHONE
5410 '
5420 GOSUB 5740     ' CALL NEWTON - EQN. 6.28
5430 '
5440 ' STORE FOCAL POINT COORDINATES
5450 FOR COORD=1 TO 3   ' STEP THROUGH X,Y,Z
5460  FPOINT(COORD)=NSOL(1,COORD)
5470 NEXT COORD                 ' NEXT COORDINATE
5480 '
5490 FOR I=1 TO 3    ' CALCULATE AND STORE FOCAL PLANE COEFFICIENTS
5500  FPLANE(I)=NSOL(2,I)-FPOINT(I)
5510 NEXT I
5520 '
5530 FPLANE(4)=0
5540 FOR I=1 TO 3     ' STEP THROUGH EACH COEFFICIENT
5550  FPLANE(4)=FPLANE(4)+FPLANE(I)*FPOINT(I)
5560 NEXT I           ' NEXT COEFFICIENT
5570 '
5580 ' CALCULATE AND STORE X, Y AND Z DIRECTION COSINES
5590 '
5600 NORM=0           ' INITIALIZE VECTOR NORM
5610 '
5620 FOR COORD=1 TO 3    ' STEP THROUGH X,Y,Z
5630  NORM=NORM+(NSOL(3,COORD)-NSOL(1,COORD))^2    ' EQN. 6.29
5640 NEXT COORD          ' NEXT COORDINATE
5650 '
5660 NORM=NORM^.5
5670 '
5680 DCOSX=(NSOL(3,1)-NSOL(1,1))/NORM    ' EQN. 6.30
5690 DCOSY=(NSOL(3,2)-NSOL(1,2))/NORM    ' EQN. 6.31
5700 DCOSZ=(NSOL(3,3)-NSOL(1,3))/NORM    ' EQN. 6.32
5710 '
5720 'RETURN '
5730 '
5740 ' SUBROUTINE: NEWTON
5750 '
5760 ' THIS SUBROUTINE SOLVES 3 SETS OF 3 NONLINEAR EQUATIONS FOR 3 UNKNOWNS.
5770 ' USING AN ITERATIVE NEWTON'S METHOD. THE EQUATIONS ARE IN THE FORM OF
5780 ' DIST=((FX1-NSOL1)^2+(FX2-NSOL2)^2+(FX3-NSOL3)^2)^.5, WHERE DIST AND FX
5790 ' ARE KNOWN AND NSOL IS UNKNOWN.
5800 '
5810 ' INPUTS: FX(POINT,COORD)- FIXED COORDINATES;
5820 '         DIST(POINT,3) - DISTANCES BETWEEN POINTS;
5830 '         CW - COSINE OF ANGLE W, S2-S1-S3 (SPARK GAPS)
5840 ' OUTPUT: NSOL(POINT,COORD) - COORDINATE SOLUTIONS
5850 ' SUBROUTINE NEEDED: INVERSE
5860 '
5870 ' SET CONSTANTS
5880 E=.001: ITERNUM = 35    ' ITERATIVE TOLERANCE AND NUMBER OF ITERATIONS
5890 ' LOOP THROUGH EACH SET OF EQUATIONS
```

```
5900 FOR MK=1 TO 3
5910 '
5920 ' STORE INITIAL SOLUTIONS
5930   FOR PT=1 TO 3
5940     M#(1,PT)=15
5950   NEXT PT
5960 '
5970 ' LOOP THROUGH UP TO 35 ITERATIONS
5980   FOR ITER=2 TO ITERNUM
5990 '
6000 ' STORE ITER-1 SOLUTION
6010     FOR PT=1 TO 3
6020       MV#(PT)=M#(ITER-1,PT)
6030     NEXT PT
6040 '
6050 ' CALCULATE JACOBIAN MATRIX COEFFICIENTS FROM THE DERIVATIVES OF THE
6060 ' EQUATIONS.
6070     FOR I=1 TO 3
6080       FOR J=1 TO 3
6090         J#(I,J)=2*(MV#(J)-FX(I,J))
6100       NEXT J
6110     NEXT I
6120 '
6130 ' INVERT THE JACOBIAN MATRIX
6140     GOSUB 3380    ' CALL INVERSE
6150 '
6160 ' DETERMINE SOLUTION ITER
6170     FOR I=1 TO 3
6180       F#(I)=(MV#(1)-FX(I,1))^2+(MV#(2)-FX(I,2))^2+(MV#(3)-FX(I,3))^2-DIST(I,MK)
6190     NEXT I
6200 '
6210     FOR I=1 TO 3
6220       M#(ITER,I)=MV#(I)-I#(I,1)*F#(1)-I#(I,2)*F#(2)-I#(I,3)*F#(3)
6230     NEXT I
6240 '
6250 ' CALCULATE ITERATIVE ERROR AND SEE IF IT IS WITHIN THE SET TOLERANCE TOL
6260     FOR I=1 TO 3
6270       T(I)=ABS(M#(ITER,I)-MV#(I))/ABS(M#(ITER,I))
6280     NEXT I
6290 '
6300 ' IF ERROR IS WITHIN TOL STORE SOLUTION OR CONTINUE TO NEXT ITERATION
6310     IF (T(1)<E) AND (T(2)<E) AND (T(3)<E) THEN 6400
6320 '
6330   NEXT ITER    ' NEXT ITERATION
6340 '
6350 ' IF NO SOLUTION IS REACHED AFTER 35 ITERATIONS PRINT ERROR MESSAGE
6360 ' AND STORE LAST ITERATION.
6370   PRINT "NO SOLUTION FOR POINT #";MK: ITER=35
6371 PRINT"THE RELATIVE ERRORS ARE:":PRINT"X-COORDINATE:",T(1)
6372 PRINT"Y-COORDINATE:",T(2): PRINT"Z-COORDINATE:",T(3): PRINT
6373 PRINT"IF YOU WANT TO DO SOME MORE ITERATIONS, ENTER HOW MUCH"
6374 PRINT"MORE, ELSE ENTER '0'";
6375 INPUT  ITERNUM
6376 IF ITERNUM<>0 THEN ITERNUM=ITERNUM+2: GOTO 5970
6377 '
6380 '
6390 ' STORE SOLUTIONS IN ARRAY NSOL
6400   FOR I=1 TO 3
6410     NSOL(MK,I)=M#(ITER,I)
6420   NEXT I
6430 '
6440 NEXT MK      ' NEXT SET OF EQUATIONS
6450 '
6460 RETURN
6470 '
6480 ' SUBROUTINE: TEST
6490 '
6500 ' THIS SUBROUTINE IS USED TO TEST THE REFERENCE SYSTEM AND REQUIRES
6510 ' THE TEST PHANTOM WHOSE FIDUCIAL COORDINATES AND TEST POINTS ARE KNOWN.
6520 ' THE OUTPUT OF THE SUBROUTINE INCLUDES THE COORDINATES OF THE FOCAL
6530 ' POINT, THE FOCAL PLANE COEFFCIENTS, THE DIRECTION COSINES OF THE
6540 ' FOCAL - ORIENTATION POINT VECTOR AND THE ABSOLUTE ERROR AT THE FOCAL
6550 ' POINT.
6560 '
6570 ' SUBROUTINES NEEDED: REGISTER, SLICE
6580 '
6590 IF HFLAG=1 GOTO 6740
6600 PRINT
6610 PRINT"ANCHOR THE TEST PHANTOM BLOCK WITH RESPECT TO THE MICROPHONES. "
6620 PRINT
6630 '
6640 ' STORE FIDUCIAL COORDINATES
6650 FX(1,1)=0: FX(1,2)=0: FX(1,3)=0
```

```
6660 FX(2,1)=-1.671: FX(2,2)=7.62: FX(2,3)=4.854
6670 FX(3,1)=1.016: FX(3,2)=15.867: FX(3,3)=-1.75
6680 '
6690 ' SET CALIBRATION FLAG FOR SUBROUTINE DISTANCE
6700 CFLAG=1
6710 '
6720 GOSUB 4220 ' CALL REGISTER-DETERMINE MICROPHONE COORDINATES
6730 '
6740 FOR I=1 TO 3 ' STORE MICROPHONE COORDINATES IN ARRAY FX FOR NEWTON
6750   FOR J=1 TO 3
6760     FX(I,J)=MIKE(I,J)
6770   NEXT J
6780 NEXT I
6790 '
6800 ' LOOP THROUGH UP TO 100 TEST POINTS
6810 FOR TPOINT=1 TO 100
6820 '
6830   PRINT "ENTER TEST POINT # (1-5) OR FIDUCIAL # (F1-F3)";
6840   INPUT TPT$
6850 '
6860 ' LOOK UP KNOWN COORDINATES OF TEST POINT
6870   IF TPT$="1" THEN TX=-4.719: TY=7.62: TZ=.79: GOTO 6970
6880   IF TPT$="2" THEN TX=2.54: TY=0: TZ=0: GOTO 6970
6890   IF TPT$="3" THEN TX=5.949: TY=7.62: TZ=4.854: GOTO 6970
6900   IF TPT$="4" THEN TX=6.096: TY=8.247: TZ=0: GOTO 6970
6910   IF TPT$="5" THEN TX=1.016: TY=15.867: TZ=.226: GOTO 6970
6920   IF TPT$="F1" THEN TX=0: TY=0: TZ=0: GOTO 6970  ' FID 1
6930   IF TPT$="F2" THEN TX=-1.671: TY=7.62: TZ=4.854: GOTO 6970 ' FID 2
6940   IF TPT$="F3" THEN TX=1.016: TY=15.867: TZ=-1.75: GOTO 6970 ' FID 3
6950   GOTO 6830
6960 '
6970   GOSUB 5080  ' CALL SLICE TO CALCULATE VALUES
6980 '
6990 ' PRINT FOCAL PLANE COEFFICIENTS
7000 PRINT
7010 PRINT"FOCAL PLANE COEFFICIENTS (A,B,C,D)"
7020 PRINT
7030 PRINT FPLANE(1),FPLANE(2),FPLANE(3),FPLANE(4)
7040 '
7050 PRINT
7060 PRINT "DIRECTION COSINES (X,Y,Z)"
7070 PRINT
7080 PRINT DCOSX,DCOSY,DCOSZ
7090 PRINT
7100 '
7110 ' PRINT TRUE AND CALCULATED VALUES OF THE FOCAL POINT AND THE ERROR IN MM.
7120 PRINT"FOCAL POINT COORDINATES"
7130   PRINT
7140   PRINT "MEASURED-";FPOINT(1),FPOINT(2),FPOINT(3)
7150   PRINT "    TRUE-";TX,TY,TZ
7160   ER=10*((FPOINT(1)-TX)^2+(FPOINT(2)-TY)^2+(FPOINT(3)-TZ)^2)^.5
7170   PRINT "ERROR IN mm.=";ER
7180   PRINT
7190 '
7200 NEXT TPOINT
7210 '
7220 RETURN
7230 '
7240 ' SUBROUTINE: RECALL-SIT
7250 '
7260 ' THIS SUBROUTINE RECALLS THE COORDINATES OF THE FOCAL, NORMAL AND
7270 ' ORIENTATION POINTS FOR THE "SITTING" SPARK GAP BRACKET FROM THE
7280 ' FILE SIT AND STORES THE COORDINATES IN ARRAY FOCAL(POINT,COORDINATE).
7290 '
7300 OPEN "SIT" FOR INPUT AS #1      ' OPEN FILE "SIT" TO READ IN COORDINATES
7301 INPUT #1,MNOT 'READ MICROPHONE WHICH WAS SHUT OFF
7310   FOR PNT=1 TO 3                ' LOOP THROUGH FOCAL, NORMAL AND ORIENT PT.
7320     FOR COORD=1 TO 3            ' LOOP THROUGH X, Y AND Z COORDINATES
7330       INPUT #1,FOCAL(PNT,COORD) ' STORE DATA IN ARRAY FOCAL(POINT,COORD)
7340     NEXT COORD                  ' NEXT COORDINATE
7350   NEXT PNT                      ' NEXT POINT
7360 CLOSE #1                        ' CLOSE FILE
7370 RETURN
7530 '
7540 ' SUBROUTINE: RECALL-MIKE
7550 '
7560 ' THIS SUBROUTINE RECALLS THE CT COORDINATES OF THE MICROPHONES THAT WERE
7570 ' STORED IN CASE THE COMPUTER FAILED AFTER THE REGISTRATION PROCEDURE
7580 '
7590 OPEN "MIKE" FOR INPUT AS #1     ' OPEN FILE "MIKE" TO READ IN COORDINATES
7600   FOR MK=1 TO 3                 ' LOOP THROUGH THE MICROPHONES
7610     FOR COORD=1 TO 3            ' LOOP THROUGH X, Y AND Z COORDINATES
7620       INPUT #1,MIKE(MK,COORD)   ' STORE DATA IN ARRAY MIKE(MK,COORD)
```

```
7630     NEXT COORD
7640    NEXT MK
7650 CLOSE #1                              ' CLOSE FILE
7660 HFLAG=1                               ' SET RECALL FLAG EQUAL TO 1
7670 RETURN
7680 ' SUBROUTINE: RECALL-FIDOUT.DAT
7690 '
7700 '   THIS SUBROUTINE RECALLS THE FIDUCIALS IN CT COORDINATES THAT
7710 '   WERE STORED BY THE PROGRAM FIDUC.FOR
7720 '
7730 OPEN "FIDOUT.DAT" FOR INPUT AS #1
7740 LINE INPUT #1, JUNK$
7750 INPUT #1, TRASH
7760 INPUT #1, TRASH
7770 FOR FID=1 TO 3
7780 INPUT #1, TRASH, FX(FID,1), FX(FID,2), FX(FID,3)
7790 NEXT FID
7800 FOR FID=1 TO 3
7810 PRINT "FID = "; FX(FID,1), FX(FID,2), FX(FID,3)
7820 NEXT FID
7830 CLOSE #1
7840 RETURN
7850 ' SUBROUTINE:  OUTPUT-RECI.DAT
7860 '
7870 '   THIS SUBROUTINE OUTPUTS THE FOCAL PLANE COEFFICIENTS,
7880 '   FOCAL POINTS, AND DIRECTION COSINES INTO THE FILE RECI.DAT
7890 '
7900 OPEN "RECI.DAT" FOR OUTPUT AS #1
7910 FOR FID=1 TO 4
7920 PRINT #1, USING "####.########"; FPLANE(FID)
7930 NEXT FID
7940 FOR FID=1 TO 3
7950 PRINT #1, USING "####.########"; FPOINT(FID)
7960 NEXT FID
7970 PRINT #1, USING "####.########"; DCOSX
7980 PRINT #1, USING "####.########"; DCOSY
7990 PRINT #1, USING "####.########"; DCOSZ
8000 CLOSE #1
8010 RETURN
8020 '
8030 ' SUBROUTINE:    OUTPUT-FIDUCIALS
8040 '
8050 '   THIS SUBROUTINE COLLECTS FIDUCIAL DATA AND WRITES THE
8060 '   DATA GATHERED TO AN OUTPUT FILE CALLED FIDUCIAL
8070 '
8080 FOR FID = 1 TO 3
8090 PRINT
8100 PRINT "FOCUS ON FIDUCIAL POINT #"; FID
8110 GOSUB 1470              ' CALL SRINP
8111 FOR LOOP1=1 TO 3
8112   FOR LOOP2=1 TO 3
8113     PRINT #3, SRMEAN(LOOP2,LOOP1)
8114   NEXT LOOP2
8115 NEXT LOOP1
8120 ' STORE AVERAGE SLANT RANGE DATA IN ARRAY SDATA
8130 FOR MK = 1 TO 3
8140 FOR SPK = 1 TO 3
8150 SDATA(FID,MK,SPK) = SRMEAN(MK,SPK)
8160 NEXT SPK
8170 NEXT MK
8180 NEXT FID
8190 ' NOW STORE THE DATA IN THE OUTPUT FILE
8200 OPEN "FIDUCIAL" FOR OUTPUT AS #1
8210 FOR FID = 1 TO 3
8220 FOR MK = 1 TO 3
8230 FOR SPK = 1 TO 3
8240 PRINT #1, SDATA(FID,MK,SPK)
8250 NEXT SPK
8260 NEXT MK
8270 NEXT FID
8280 CLOSE #1
8285 IF TST$="Y" THEN STFL=1: ELSE STFL=3
8290 RETURN
8300 '
8310 ' SUBROUTINE:    RECALL-FIDUCIALS
8320 '
8330 '   THIS SUBROUTINE RECALLS THE ARRAY SDATA FROM A PREVIOUS
8340 '   FIDUCIAL COLLECTION RUN SAVING THE INPUT OF FIDUCIALS 1, 2, 3
8350 '   OVER AND OVER AGAIN.  THIS IS OK PROVIDED THE PATIENT IS
8360 '   NOT MOVED.
8370 '
8380 OPEN "FIDUCIAL" FOR INPUT AS #1
8390 FOR FID = 1 TO 3
```

```
8400 FOR MK = 1 TO 3
8410   FOR SPK = 1 TO 3
8420     INPUT #1,SDATA(FID,MK,SPK)
8430   NEXT SPK
8440 NEXT MK
8450 NEXT FID
8460 CLOSE #1
8470 RETURN
9000 ' SUBROUTINE: STATISTICAL LOG
9010 '
9012 '
9020 FOR L1 = 1 TO 3
9030 '
9040    FOR L2 = 1 TO 7
9050       CLASS(L2) = 0
9060    NEXT L2
9070 '
9090    MIN = SLANT(1,L1): MAX = SLANT(1,L1)
9095 '
9100    FOR L2 = 1 TO NUMSPAR
9110       IF SLANT(L2,L1) > 245 THEN GOTO 9210
9120       IF SLANT(L2,L1) > MAX THEN MAX = SLANT(L2,L1)
9130       IF SLANT(L2,L1) < MIN THEN MIN = SLANT(L2,L1)
9140       IF SLANT(L2,L1) >(SMEAN(L1)+.06)THEN CLASS(1)=CLASS(1)+1: GOTO 9210
9150       IF SLANT(L2,L1) >(SMEAN(L1)+.03)THEN CLASS(2)=CLASS(2)+1: GOTO 9210
9160       IF SLANT(L2,L1) >(SMEAN(L1)+.01)THEN CLASS(3)=CLASS(3)+1: GOTO 9210
9170       IF SLANT(L2,L1) >(SMEAN(L1)-.01)THEN CLASS(4)=CLASS(4)+1: GOTO 9210
9180       IF SLANT(L2,L1) >(SMEAN(L1)-.03)THEN CLASS(5)=CLASS(5)+1: GOTO 9210
9190       IF SLANT(L2,L1) >(SMEAN(L1)-.06)THEN CLASS(6)=CLASS(6)+1: GOTO 9210
9200       CLASS(7) = CLASS(7) + 1
9210    NEXT L2
9220 '
9230    IF STFL = 1 THEN PRINT #2,"TESTPOINT:",TPT$
9240    IF STFL = 2 THEN PRINT #2,"FIDUCIAL:",FID
9250    IF STFL = 3 THEN PRINT #2,"SLANTRANGES FOR DETERMINING FOCAL PLANE"
9300 '
9310    PRINT#2,"SPARKGAP:",SGAP+1," MIKE:",MICE(MNO1,L1)," SPARKS:",NUMSPAR
9320    PRINT#2,"MEAN:",SMEAN(L1)," STANDARD DEVIATION:",SD(L1)
9330    PRINT#2,"SLANTRANGES > 245cm:",BAD(L1)
9340    PRINT#2,"MIN:",MIN," MAX:",MAX
9350 '
9360    FOR L2 = 1 TO 7
9370       PRINT #2,CLASS(L2)
9380    NEXT L2
9390    PRINT #2," "
9400 NEXT L1
9410 PRINT #2," "
9420 RETURN
```

*Appendix C*

```
100 ' PROGRAM FocalPlaneDefinition (FPL)
110 '
120 ' This program determines the relative position of the operating microscope's
130 ' focal plane with respect to the triangle made up by the sparkgaps.
140 '
150 ' Programmer: John F. Hatch
160 '             Johann Kettenberger
170 '             William J. Murray
180 '
190 ' Date: September 11, 1985
200 '
210 ' Version: 0.1
220 '
230 OPTION Base 1                  'start array indices with 1 instead of 0
240 '
250 '*** Array Declarations ****************************************************
260 '
270 DIM MikeGapSlant(4,3,300)      'holds slantranges; 1.index: microphone,
280                                '2.index: sparkgap, 3.index: # of slantranges
290                                'to be collected (Max = 300)
300 DIM SlantMean(4,3)             'holds mean slantranges calculated from the
310                                'slantranges in MikeGapSlant; 1.index: micro-
320                                'phone, 2.index: sparkgap
330 DIM Class(7)                   'histogram classes for the statistical analysis
```

```
340                                       'of the slantrange distribution
350  DIM Focal(3)                         'coordinates of 4. sparkgap (focal point) in
360                                       'the microphone coordinate system
370  DIM MikeDist(4,3)                    'distances between microphones, 1.index: micro-
380                                       'phone being shut off, 2.index: 1=distance ori-
390                                       'gin microphone - X-axis microphone, 2=distance
400                                       'origin microphone - Y-axis microphone, 3= dis-
410                                       'tance X-axis - Y-axis microphone
420  DIM Index(4,3)                       'changes indices depending on which microphone
430                                       'is shut off. This allows to use the same for-
440                                       'mulas independent of the microphone being shut
450                                       'off. 1.index: microphone shut off, 2.index:
460                                       '1=X-axis microphone, 2=Origin microphone,
470                                       '3=Y-axis microphone
480  DIM CosA(4)                          'cosine of angle between X-axis and Y-axis mi-
490                                       'crophone at origin. Index: microphone shut off
500  DIM SinA(4)                          'sine of the angle described above
510  DIM GapCoord(3,3)                    'coordinates of sparkgaps in microphone system
520                                       '1.index: sparkgap, 2.index: coordinate (1=X,
530                                       '2=Y, 3=Z)
540  DIM GaptoCoG(3,3)                    'vector from a sparkgap to the midpoint of the
550                                       'opposite sparkgap triangle side through the
560                                       'center of gravity of the triangle
570                                       '1.index: sparkgap, 2.index: coordinates
580  DIM CoG(3)                           'coordinates of center of gravity of sparkgap
590                                       'triangle
600  DIM DisG(3)                          'distances from center of gravity to sparkgaps
610  DIM TriNorm(3)                       'normal vector of sparkgap triangle
620  DIM Vec1(3,3)                        'auxiliary vector needed for determining the
630                                       'correct positions of the sparkgaps
640                                       '1.index: sparkgap, 2.index: coordinates
650  DIM Vec2(3,3)                        'as Vec1
660  DIM NewGap(3,3,3)                    'set of corrected sparkgap coordinates
670                                       '1.index: sparkgap chosen to orient corrected
680                                       'sparkgap triangle, 2.index: sparkgap,
690                                       '3.index: coordinates
700  DIM NormVec1(3)                      'factors to normalize vectors Vec1
710  DIM NormVec2(3)                      'factors to normalize vectors Vec2
720  DIM Mike(4,3,3)                      'microphone coordinates depending on which one
730                                       'is shut off. 1.index: microphone shut off,
740                                       '2.index: 1=X-axis microphone, 2=Origin micro-
750                                       'phone, 3=Y-axis microphone, 3.index: coord's
760  DIM StoreGap(3,3)                    'sparkgap coordinates when microscope is
770                                       'focused on 4. sparkgap. 1.index: sparkgap,
780                                       '2.index: coordinate
790  DIM NewCoord(3,3)                    'improved sparkgap coordinates calculated from
800                                       'improved slantranges. 1.index: sparkgap,
810                                       '2.index: coordinates
820  DIM XAxis(3)                         'X-axis of oblique sparkgap based system to de-
830                                       'termine the relative position of focal, normal
840                                       'and orientation point. X-axis goes from spark-
850                                       'gap#1 (origin) to sparkgap#3
860  DIM YAxis(3)                         'goes from sparkgap#1 to sparkgap#2
870  DIM ZAxis(3)                         'cross product of XAxis x YAxis
880  DIM XFac(3)                          'factors with which XAxis,YAxis,ZAxis vectors
890  DIM YFac(3)                          'have to be multiplied to go from sparkgap#1
900  DIM ZFac(3)                          'to the focal(index=1), normal(index=2) or
910                                       'orientation point(index=3)
920  DIM Dif(3)                           'differences between successive calcu-
930                                       'lations of sparkgap coordinates
940  DIM Orient(3)                        'Orientation point coordinates
950  DIM Normal(3)                        'Normal vector of the focal plane
960  '
970  '*** Array Initializations and Constants ************************************
980  '
990  'Order of Index Permutation
1000 '
1010 Index(1,1)=4: Index(1,2)=3: Index(1,3)=2
1020 Index(2,1)=1: Index(2,2)=4: Index(2,3)=3
1030 Index(3,1)=2: Index(3,2)=1: Index(3,3)=4
1040 Index(4,1)=3: Index(4,2)=2: Index(4,3)=1
1050 '
1060 'Measured Microphone Distances
1070 '
1080 MikeDist(1,1)=96.243: MikeDist(1,2)=100.289: MikeDist(1,3)=137.754  '[cm]
1090 MikeDist(2,1)=101.965:MikeDist(2,2)=96.243:MikeDist(2,3)=140.962
1100 MikeDist(3,1)=95.697:MikeDist(3,2)=101.965:MikeDist(3,3)=137.754
1110 MikeDist(4,1)=100.289:MikeDist(4,2)=95.697:MikeDist(4,3)=140.962
1120 '
1130 'Cosine/Sine of Angle at Origin of Microphone Coordinate System
1140 '
1145 FOR Mik=1 TO 4
1150 CosA(Mik)=MikeDist(Mik,1)^2+MikeDist(Mik,2)^2-MikeDist(Mik,3)^2
1160 CosA(Mik)=CosA(Mik)/(2*MikeDist(Mik,1)*MikeDist(Mik,2))
1170 SinA(Mik)=SQR(1-CosA(Mik)*CosA(Mik))
1175 NEXT Mik
1180 '
1190 'Distances from the Center of Gravity of the Sparkgap Triangle to the Sparkgaps
1200 '
1210 DisG(1)=17.341285: DisG(2)=17.204482: DisG(3)=17.231647
1220 '
1230 'Angles needed to calculate corrected Sparkgap Positions
```

```
1240 '
1250 CosA12=0.4968336: SinA12=0.8678458
1260 CosA13=0.5038557 : SinA13=0.8637878
1270 CosA21=0.4926918 : SinA21=0.8702039
1280 CosA23=0.4959331: SinA23=0.8653607
1290 CosA31=0.5071646: SinA31=0.8618492
1300 CosA32=0.5031794: SinA32=0.864182
1310 '
1320 'Microphone Coordinates
1330 '
1335 FOR Mik=1 TO 4
1340 Mike(Mik,1,1)=MikeDist(Mik,1): Mike(Mik,1,2)=0: Mike(Mik,1,3)=0
1350 Mike(Mik,2,1)=0: Mike(Mik,2,2)=0: Mike(Mik,2,3)=0
1360 Mike(Mik,3,1)=MikeDist(Mik,2)*CosA(Mik): Mike(Mik,3,2)=MikeDist(Mik,2)*SinA(Mik): Mike(Mik,3,3)=0
1365 NEXT Mik
1370 '
1380 '*** Start of Main Program *********************************************
1390 '
1400 'Error Handling Routine
1410 '
1420 ON Error GOTO 2230
1430 PRINT
1440 PRINT
1450 PRINT"Program FPL: Definition of the microscope's focal plane"
1460 PRINT
1470 PRINT"Version: 0.1"
1480 PRINT
1490 OPEN "FPL.Log" FOR OUTPUT AS #2
1500 '
1510 'Interactive Input of Microphone to be shut off and Number of Sparks to fire
1520 '
1530 PRINT
1540 PRINT"Which microphone do you want to be ignored [1-4] ";
1550 INPUT ShutOffMike
1560 IF (ShutOffMike<1) OR (ShutOffMike>4) GOTO 1540
1570 IF ShutOffMike>1 THEN PRINT"Sorry, but currently only microphone#1 can be switched off.": GOTO 1540
1580 PRINT
1590 PRINT"How many sparks per sparkgap do you want to fire [Max.=300] ";
1600 INPUT Sparks
1610 IF (Sparks<1) OR (Sparks>300) GOTO 1590
1620 '
1630 PRINT
1640 PRINT"Switch on the digitizer and the sparkgap multiplexer."
1650 PRINT"If the communication between the digitizer and the"
1660 PRINT"IBM XT fails initially then the program will restart"
1670 PRINT"itself. It can therefore happen, that the fourth"
1680 PRINT"sparkgap is fired twice."
1690 '
1700 'Step 1: Determination of the relative Focal Point Position
1710 '
1720 GOSUB 5000
1730 '
1740 'Record the Data in the File Resume.Dat
1750 '
1760
1770 PRINT
1780 PRINT"The relative focal point position is determined."
1790 PRINT"Factor for the X-Axis vector: ";XFac(1)
1800 PRINT"Factor for the Y-Axis vector: ";YFac(1)
1810 PRINT"Factor for the Z-Axis vector: ";ZFac(1)
1820 '
1830 'Step 2: Determination of the relative Normal Point Position
1840 '
1850 GOSUB 30000
1860
1870 PRINT
1880 PRINT"The relative normal point position is determined."
1890 PRINT"Factor for the X-Axis vector: ";XFac(2)
1900 PRINT"Factor for the Y-Axis vector: ";YFac(2)
1910 PRINT"Factor for the Z-Axis vector: ";ZFac(2)
1920 '
1930 'Step 3: Dtermination of the relative Orientation Point Position
1940 '
1950 GOSUB 40000
1960
1970 PRINT
1980 PRINT"The relative orientation point position is determined."
1990 PRINT"Factor for the X-Axis vector: ";XFac(3)
2000 PRINT"Factor for the Y-Axis vector: ";YFac(3)
2010 PRINT"Factor for the Z-Axis vector: ";ZFac(3)
2020
2030 CLOSE #2
2040 '
2050 'Save the Factors in the File 'FPL.DAT' for the Program REG
2060 '
2070 OPEN "Fpl.Dat" FOR OUTPUT AS #2
2080 PRINT#2,Date$
2090 PRINT#2,Time$
2100 PRINT#2,ShutOffMike
2110 PRINT#2,Sparks
2120 FOR I=1 TO 3
2130    PRINT#2,XFac(I)
2140    PRINT#2,YFac(I)
```

```
2150    PRINT#2,ZFac(I)
2160 NEXT I
2170 CLOSE #2
2180
2190 PRINT
2200 PRINT"The focal, normal and orientation point data are stored in"
2210 PRINT"the file 'FPL.DAT'."
2220 '
2230 'Error Handling Routine
2240 '
2250 IF (Err=57) AND (Erl<10490) THEN PRINT: PRINT"The communication with the digitizer failed.": PRINT
     "The program has been reset and restarted.": GapToFire=1: GOTO 10210
2260
2270 ON Error GOTO 0 'For all the error not trapped here
2280
2290 END
5000 '
5010 'Subroutine: Relative Focal Point Location
5020 '
5030 'This subroutine determines the relative location of the microscope's focal
5040 'point with respect to the sparkgap triangle. This is achieved by calcu-
5050 'lating the scalar factors with which the XAxis, YAxis and ZAxis vectors
5060 'have to be multiplied in order to point from the sparkgap #1 to the focal
5070 'point.
5080 '
5090 'Programmer: Johann Kettenberger
5100 '
5110 'Date: September 11, 1985
5120 '
5130 '*** Start of Subroutine ******************************************************
5140 '
5150 'User Guidance
5160 '
5170 PRINT
5180 PRINT"Please connect the 4. sparkgap to the sparkgap multiplexer"
5190 PRINT"output #1. Make sure that there is a clear line of sight"
5200 PRINT"between the 4. sparkgap and each one of the used microphones."
5210 '
5220 'Collect and Process the Slantranges
5230 '
5240 GapToFire=1
5250 GOSUB 10000
5260 '
5270 'Calculate the Position of the 4. Sparkgap in Microphone Coordinates
5280 '
5290 Focal(1)=(MikeDist(ShutOffMike,1)^2+SlantMean(Index(ShutOffMike,2),1)^2-SlantMean(Index(ShutOffMike,
     1),1)^2)/(2*MikeDist(ShutOffMike,1))
5300 Focal(2)=(MikeDist(ShutOffMike,2)^2+SlantMean(Index(ShutOffMike,2),1)^2-SlantMean(Index(ShutOffMike,
     3),1)^2)/(2*MikeDist(ShutOffMike,2))
5310 Focal(2)=(Focal(2)-Focal(1)*CosA(ShutOffMike))/SinA(ShutOffMike)
5320 Focal(3)=-SQR(SlantMean(Index(ShutOffMike,2),1)^2-Focal(1)^2-Focal(2)^2)
5330 '
5340 'Determine the Position of the Sparkgap Triangle when the Microscope is focused
5350 ' on the 4. Sparkgap
5360 '
5370 PRINT
5380 PRINT"Connect all three sparkgaps to the sparkgap multiplexer and focus"
5390 PRINT"on the 4. sparkgap. Be sure that the microscope's magnification"
5400 PRINT"setting is at 2.5 and the microscope in its high position."
5410
5420 FOR GapToFire = 1 TO 3
5430    GOSUB 10000
5440 NEXT GapToFire
5450 '
5460 'Calculate the Coordinates of the Sparkgaps in Microphone Coordinates
5470 '
5480 GOSUB 20000
5490 '
5500 'Determine the Relative Position of the Focal Point
5510 'Calculate the Vector Sparkgap#1 - Focal Point
5520 '
5530 Focal(1)=Focal(1)-GapCoord(1,1)
5540 Focal(2)=Focal(2)-GapCoord(1,2)
5550 Focal(3)=Focal(3)-GapCoord(1,3)
5560 '
5570 'Determine the Oblique Focal Point Coordinates
5580 '
5590 GOSUB 25000
5600 '
5610 'Store the Solution
5620 '
5630 XFac(1)=XFactor
5640 YFac(1)=YFactor
5650 ZFac(1)=ZFactor
5660
5670 RETURN
10000 '
10010 'Subroutine: Slantrange Input
10020 '
10030 'This subroutine inputs the slantranges measured by the ultrasonic digitizer
10040 'via the RS-232 serial port of the IBM XT. The parallel port of the IBM XT
10050 'is used to set the sparkgap multiplexer.
10060 '
```

```
10070 'Programmer: John F. Hutch (William J. Murray, Johann Kettenberger)
10080 '
10090 'Date: September 11, 1985
10100 '
10110 '*** Start of Subroutine ***********************************************
10120 '
10130 IF GapToFire <> 1 GOTO 10210      'decide whether or not to display message
10140 PRINT
10150 PRINT"*** Press any key when ready ***"
10160 AnyKey$=INKEY$
10170 IF AnyKey$="" GOTO 10160
10180 '
10190 'Translate the Gap to be fired into the proper Multiplexer Code
10200 '
10210 IF GapToFire=1 THEN MuxCode=0
10220 IF GapToFire=2 THEN MuxCode=2
10230 IF GapToFire=3 THEN MuxCode=1
10240 '
10250 'Set the Multiplexer via the parallel Port
10260 '
10270 OUT &H3BC,MuxCode        'H3BC: hexadecimal address of parallel port
10280 '
10290 'Set serial Port for Digitizer Communication
10300 '
10310 OPEN "COM1:9600,0,7,1" AS #1
10320 '
10330 'Search for ASCII line feed in incoming data
10340 '
10350 InData$="a"
10360 WHILE (ASC(InData$)<>10)
10370    InData$=INPUT$(1,#1)
10380 WEND
10390 '
10400 'Ignore the first Set of Data
10410 '
10420 InData$=INPUT$(26,#1)
10430 '
10440 'Collect the Slantranges from the current Sparkgap
10450 '
10460 FOR I=1 TO Sparks
10470    IF LOC(1)>200 THEN OUT &H3FC,10 ELSE OUT &H3FC,11 'avoid comm.buffer overflow
10480    InData$=INPUT$(26,#1)  'input the slantranges
10490    FOR J=1 TO 4           'convert the strings into real numbers
10500       IF J=ShutOffMike GOTO 10550
10510       Value$=MID$(InData$,(J*6-5),6)
10520       Whole$=LEFT$(Value$,3)
10530       Decimal$=RIGHT$(Value$,3)
10540       MikeGapSlant(J,GapToFire,I)=Val(Whole$+"."+Decimal$)
10550    Next J
10560 NEXT I
10570 CLOSE #1      'suppress communication
10580 '
10590 'Analyze the Slantrange Data statistically
10600 '
10610 Repeat=0
10620 GOSUB 15000
10630 '
10640 'Check if the Data are o.k.
10650 '
10660 IF Repeat=1 THEN Print"Slantranges between microphone ";Mike;" and sparkgap#";GapToFire;" are
      greater than 200cm.": PRINT"Try again": GOTO 10140
10670 IF Repeat=2 THEN PRINT"Too much variance in slantranges between microphone ";Mike;" and sparkgap#";
      GapToFire: PRINT"Try again": GOTO 10140
10680 '
10690 'Store the Mean Slantranges and add the Counter Delay
10700 '
10710 FOR Mike=1 TO 4
10720    SlantMean(Mike,GapToFire)=SlantMean(Mike,GapToFire)+4.45 'add counter delay
10730 NEXT Mike
10740 '
10750 RETURN
15000 '
15010 'Subroutine: Statistical Analysis of Slantrange Data
15020 '
15030 'This subroutine calculates the mean from the total number of slantranges
15040 'collected. It sorts out the slantranges which are +/-0.5mm off the mean
15050 'and calculates thereof an improved mean. The slantranges are classified
15060 'in a histogram which is recorded in the file 'FPL.Log'.
15070 '
15080 'Programmer: Johann Kettenberger
15090 '
15100 'Date: September 11, 1985
15110 '
15120 '*** Start of Subroutine ***********************************************
15130 '
15140 'Calculation of the 1. Estimate of the Mean
15150 '
15160 FOR Mike=1 TO 4
15170    IF Mike=ShutOffMike GOTO 15720
15180    SortedOut=0
15190    SlantSum=0
15200    FOR I=1 TO Sparks
15210       IF MikeGapSlant(Mike,GapToFire,I)<245 THEN SlantSum=SlantSum+MikeGapSlant(Mike,GapToFire,I)
          ELSE SortedOut=SortedOut+1
```

```
15220    NEXT I
15230    IF SortedOut>(0.1*Sparks) THEN Repeat=1: GOTO 15730
15240    SlantMean(Mike,GapToFire)=SlantSum/(Sparks-SortedOut)
15250  '
15260  'Calculation of the Standard Deviation
15270  '
15280    SlantSum=0
15290    FOR I=1 TO Sparks
15300      IF MikeGapSlant(Mike,GapToFire,I)<245 THEN SlantSum=SlantSum+(MikeGapSlant(Mike,GapToFire,I)-
         SlantMean(Mike,GapToFire))^2
15310    NEXT I
15320    StdDev=SlantSum/(Sparks-SortedOut)
15330  '
15340  'Calculation of improved Mean
15350  '
15360    SortedOut=0
15370    SlantSum=0
15380    FOR I=1 TO Sparks
15390      Dif=ABS(MikeGapSlant(Mike,GapToFire,I)-SlantMean(Mike,GapToFire))
15400      IF Dif<0.05 THEN SlantSum=SlantSum+MikeGapSlant(Mike,GapToFire,I) ELSE SortedOut=SortedOut+1
15410    NEXT I
15420    IF SortedOut>(0.3*Sparks) THEN Repeat=2: GOTO 15730
15430    SlantMean(Mike,GapToFire)=SlantSum/(Sparks-SortedOut)
15440  '
15450  'Classification of the Slantranges in the Histogram
15460  '
15470    FOR I=1 TO 7
15480      Class(I)=0
15490    NEXT I
15500
15510    FOR I=1 TO Sparks
15520      IF MikeGapSlant(Mike,GapToFire,I)>(SlantMean(Mike,GapToFire)+.05) THEN Class(1)=Class(1)+1:
         GOTO 15590
15530      IF MikeGapSlant(Mike,GapToFire,I)>(SlantMean(Mike,GapToFire)+.03) THEN Class(2)=Class(2)+1:
         GOTO 15590
15540      IF MikeGapSlant(Mike,GapToFire,I)>(SlantMean(Mike,GapToFire)+.01) THEN Class(3)=Class(3)+1:
         GOTO 15590
15550      IF MikeGapSlant(Mike,GapToFire,I)>(SlantMean(Mike,GapToFire)-.01) THEN Class(4)=Class(4)+1:
         GOTO 15590
15560      IF MikeGapSlant(Mike,GapToFire,I)>(SlantMean(Mike,GapToFire)-.03) THEN Class(5)=Class(5)+1:
         GOTO 15590
15570      IF MikeGapSlant(Mike,GapToFire,I)>(SlantMean(Mike,GapToFire)-.05) THEN Class(6)=Class(6)+1:
         GOTO 15590
15580      Class(7)=Class(7)+1
15590    NEXT I
15600  '
15610  'Record Histogram
15620  '
15630    PRINT #2, GapToFire
15640    PRINT #2, Mike
15650    PRINT #2, Sparks
15660    PRINT #2, SlantMean(Mike,GapToFire)
15670    PRINT #2, StdDev
15680    FOR I=1 TO 7
15690      PRINT #2, Class(I)
15700    NEXT I
15710
15720  NEXT Mike
15730
15740  RETURN
20000  '
20010  'Subroutine: Sparkgap Coordinates
20020  '
20030  'This subroutine calculates the coordinates of the sparkgaps in the micro-
20040  'phone system. An iterative procedure is used to correct for random errors
20050  'in the slantranges.
20060  'The iteration starts by calculating the sparkgap positions. It checks then
20070  'if the calculated sparkgap positions form a triangle which corresponds to
20080  'the triangle known from measurements of the distances between the spark-
20090  'gaps. If this is not the case, then the center of gravity of the precise
20100  'sparkgap triangle is located at the center of gravity of the calculated
20110  'triangle and improved sparkgap locations are determined. The orientation
20120  'of the precise sparkgap triangle with respect to the calculated one is
20130  'given through the sparkgap-center of gravity vectors of the calculated
20140  'sparkgap triangle. Since there are three of those vectors three different
20150  'orientations of the precise sparkgap triangle are to be considered. This
20160  'results in three improved estimates of the sparkgap locations and three
20170  'sets of improved slantranges. The improved slantranges for each micro-
20180  'phone-sparkgap combination are averaged and used to compute new sparkgap
20190  'positions. This iterative refinement of the sparkgap locations goes on
20200  'until the convergence criterium is met.
20210  '
20220  'Programmer: Johann Kettenberger
20230  '
20240  'Date: September 12, 1985
20250  '
20260  '*** Start of Subroutine ***************************************************
20270  '
20280  'Initial Calculation of the Sparkgap Coordinates
20290  '
20300  FOR Gap=1 TO 3
20310    GapCoord(Gap,1)=(MikeDist(ShutOffMike,1)^2+SlantMean(Index(ShutOffMike,2),Gap)^2-SlantMean(Index
         (ShutOffMike,1),Gap)^2)/(2*MikeDist(ShutOffMike,1))
20320    GapCoord(Gap,2)=(MikeDist(ShutOffMike,2)^2+SlantMean(Index(ShutOffMike,2),Gap)^2-SlantMean(Index
         (ShutOffMike,3),Gap)^2)/(2*MikeDist(ShutOffMike,2))
```

```
20330     GapCoord(Gap,2)=(GapCoord(Cap,2)-GapCoord(Cap,1)*CosA(ShutOffMike))/SinA(ShutOffMike)
20340     GapCoord(Gap,3)=-SQR(SlantMean(Index(ShutOffMike,2),Gap)^2-GapCoord(Gap,1)^2-GapCoord(Gap,2)^2)
20350 NEXT Gap
20360 '
20370 'Start Iteration
20380 '
20390 Busy=1
20400 WHILE Busy
20410 '
20420 'Calculate the Center of Gravity and the vectors from each Sparkgap through
20430 'the Center of Gravity (Orientation vectors)
20440 '
20450   FOR Coord=1 TO 3  'Center of Gravity and Orientation vector from gap#1
20460     GapToCoG(1,Coord)=GapCoord(2,Coord)+.5*(GapCoord(3,Coord)-GapCoord(2,Coord))-GapCoord(1,Coord)
20470     CoG(Coord)=GapCoord(1,Coord)+2/3*GapToCoG(1,Coord)
20480   NEXT Coord
20490   FOR Coord=1 TO 3  'Orientation vector from gap#2
20500     GapToCoG(2,Coord)=GapCoord(3,Coord)+.5*(GapCoord(1,Coord)-GapCoord(3,Coord))-GapCoord(2,Coord)
20510   NEXT Coord
20520   FOR Coord=1 TO 3  'Orientation vector from gap#3
20530     GapToCoG(3,Coord)=GapCoord(1,Coord)+.5*(GapCoord(2,Coord)-GapCoord(1,Coord))-GapCoord(3,Coord)
20540   NEXT Coord
20550 '
20560 'Calculate the improved Sparkgap Positions lying on the Orientation vectors
20570 '
20580   FOR Gap=1 TO 3
20590     FOR Coord=1 TO 3
20600       NewGap(Gap,Gap,Coord)=CoG(Coord)-GapToCoG(Gap,Coord)/SQR(GapToCoG(Gap,1)^2+GapToCoG(Gap,2)
      ^2+GapToCoG(Gap,3)^2)*DisG(Gap)
20610     NEXT Coord
20620   NEXT Gap
20630 '
20640 'Calculate the Normal of the Sparkgap Triangle
20650 '
20660   TriNorm(1)=GapToCoG(2,2)*GapToCoG(1,3)-GapToCoG(2,3)*GapToCoG(1,2)
20670   TriNorm(2)=GapToCoG(2,3)*GapToCoG(1,1)-GapToCoG(2,1)*GapToCoG(1,3)
20680   TriNorm(3)=GapToCoG(2,1)*GapToCoG(1,2)-GapToCoG(2,2)*GapToCoG(1,1)
20690 '
20700 'Calculate Vec1 = TriNorm x GapToCoG; Vec2 = Vec1 x TriNorm
20710 '
20720   FOR Gap=1 TO 3
20730     Vec1(Gap,1)=TriNorm(2)*GapToCoG(Gap,3)-TriNorm(3)*GapToCoG(Gap,2)
20740     Vec1(Gap,2)=TriNorm(3)*GapToCoG(Gap,1)-TriNorm(1)*GapToCoG(Gap,3)
20750     Vec1(Gap,3)=TriNorm(1)*GapToCoG(Gap,2)-TriNorm(2)*GapToCoG(Gap,1)
20760     NormVec1(Gap)=SQR(Vec1(Gap,1)^2+Vec1(Gap,2)^2+Vec1(Gap,3)^2)
20770     Vec2(Gap,1)=Vec1(Gap,2)*TriNorm(3)-Vec1(Gap,3)*TriNorm(2)
20780     Vec2(Gap,2)=Vec1(Gap,3)*TriNorm(1)-Vec1(Gap,1)*TriNorm(3)
20790     Vec2(Gap,3)=Vec1(Gap,1)*TriNorm(2)-Vec1(Gap,2)*TriNorm(1)
20800     NormVec2(Gap)=SQR(Vec2(Gap,1)^2+Vec2(Gap,2)^2+Vec2(Gap,3)^2)
20810   NEXT Gap
20820 '
20830 'Calculate the improved Sparkgap Positions off the Orientation vector
20840 '
20850   FOR Coord=1 TO 3  'Orientation given by Sparkgap#1
20860     NewGap(1,2,Coord)=NewGap(1,1,Coord)+30.041*(SinA12*Vec2(1,Coord)/NormVec2(1)+CosA12*Vec1(1,
      Coord)/NormVec1(1))
20870     NewGap(1,3,Coord)=NewGap(1,1,Coord)+29.657*(SinA13*Vec2(1,Coord)/NormVec2(1)-CosA13*Vec1(1,
      Coord)/NormVec1(1))
20880   NEXT Coord
20890   FOR Coord=1 TO 3  'Orientation given by Sparkgap#2
20900     NewGap(2,1,Coord)=NewGap(2,2,Coord)+30.041*(SinA21*Vec2(2,Coord)/NormVec2(2)-CosA21*Vec1(2,
      Coord)/NormVec1(2))
20910     NewGap(2,3,Coord)=NewGap(2,2,Coord)+29.995*(CosA23*Vec1(2,Coord)/NormVec1(2)+SinA23*Vec2(2,
      Coord)/NormVec2(2))
20920   NEXT Coord
20930   FOR Coord=1 TO 3  'Orientation given by Sparkgap#3
20940     NewGap(3,1,Coord)=NewGap(3,3,Coord)+29.657*(CosA31*Vec1(3,Coord)/NormVec1(3)+SinA31*Vec2(3,
      Coord)/NormVec2(3))
20950     NewGap(3,2,Coord)=NewGap(3,3,Coord)+29.995*(SinA32*Vec2(3,Coord)/NormVec2(3)-CosA32*Vec1(3,
      Coord)/NormVec1(3))
20960   NEXT Coord
20970 '
20980 'Calculate the improved Slantranges
20990 '
21000   FOR Gap=1 TO 3
21010     FOR Micro=1 TO 3
21020       SlantMean(Index(ShutOffMike,Micro),Gap)=0
21030       FOR OGap=1 TO 3
21040         NewSlant=0
21050         FOR Coord=1 TO 3
21060           NewSlant=NewSlant+(Mike(ShutOffMike,Micro,Coord)-NewGap(OGap,Gap,Coord))^2
21070         NEXT Coord
21080         NewSlant=SQR(NewSlant)
21090         SlantMean(Index(ShutOffMike,Micro),Gap)= SlantMean(Index(ShutOffMike,Micro),Gap)+NewSlant
21100       NEXT OGap
21110       SlantMean(Index(ShutOffMike,Micro),Gap)=SlantMean(Index(ShutOffMike,Micro),Gap)/3
21120     NEXT Micro
21130   NEXT Gap
21140 '
21150 'Calculate the new Sparkgap Coordinates resulting from the new Slantranges
21160 '
21170   FOR Gap=1 TO 3
21180     NewCoord(Gap,1)=(MikeDist(ShutOffMike,1)^2+SlantMean(Index(ShutOffMike,2),Gap)^2-SlantMean
      (Index(ShutOffMike,1),Gap)^2)/(2*MikeDist(ShutOffMike,1))
```

```
21190      NewCoord(Gap,2)=(MikeDist(ShutOffMike,2)^2+SlantMean(Index(ShutOffMike,2),Gap)^2-SlantMean
           (Index(ShutOffMike,3),Gap)^2)/(2*MikeDist(ShutOffMike,2))
21200      NewCoord(Gap,2)=(NewCoord(Gap,2)-NewCoord(Gap,1)*CosA(ShutOffMike))/SinA(ShutOffMike)
21210      NewCoord(Gap,3)=-SQR(SlantMean(Index(ShutOffMike,2),Gap)^2-NewCoord(Gap,1)^2-NewCoord(Gap,2)^2)
21220    NEXT Gap
21230 '
21240 'Determine the Difference to the previous Result
21250 '
21260    FOR Gap=1 TO 3
21270      Dif(Gap)=0
21280      FOR Coord=1 TO 3
21290        Dif(Gap)=Dif(Gap)+(GapCoord(Gap,Coord)-NewCoord(Gap,Coord))^2
21300      NEXT Coord
21310      Dif(Gap)=SQR(Dif(Gap))
21320    NEXT Gap
21330 '
21340 'Determine whether or not the Convergence Criteria is met
21350 '
21360    IF (Dif(1)<.01)AND(Dif(2)<.01)AND(Dif(3)<.01) THEN Busy=0
21370 '
21380 'Store the current Solution
21390 '
21400    FOR Gap=1 TO 3
21410      FOR Coord=1 TO 3
21420        GapCoord(Gap,Coord)=NewCoord(Gap,Coord)
21430      NEXT Coord
21440    NEXT Gap
21450
21460 WEND
21470
21480 RETURN
25000 '
25010 'Subroutine: Oblique Focal Point Coordinates
25020 '
25030 'All positions (focal point and sparkgaps) are known in microphone coordi-
25040 'nates. The relative location of the focal point is expressed as a linear
25050 'combination of the vectors XAxis (vector sparkgap#1-sparkgap#3), YAxis
25060 '(vector sparkgap#1-sparkgap#2) and ZAxis (crossproduct of XAxis x YAxis).
25070 'These vectors form an oblique righthanded coordinate system with origin
25080 'at sparkgap#1.
25090 'To solve is the vector equation:
25100 'Focal[1-3] = XFactor*XAxis[1-3] + YFactor*YAxis[1-3] + ZFactor*ZAxis[1-3]
25110 'This is done using the determinant method.
25120 '
25130 'Programmer: Johann Kettenberger
25140 '
25150 'Date: September 13, 1985
25160 '
25170 '*** Start of Subroutine ***************************************************
25180 '
25190 'Calculate the Vectors XAxis, YAxis, ZAxis
25200 '
25210 FOR Coord = 1 TO 3
25220    XAxis(Coord)=GapCoord(3,Coord)-GapCoord(1,Coord)
25230    YAxis(Coord)=GapCoord(2,Coord)-GapCoord(1,Coord)
25240 NEXT Coord
25250
25260 ZAxis(1)=(XAxis(2)*YAxis(3)-XAxis(3)*YAxis(2))/100
25270 ZAxis(2)=(XAxis(3)*YAxis(1)-XAxis(1)*YAxis(3))/100
25280 ZAxis(3)=(XAxis(1)*YAxis(2)-XAxis(2)*YAxis(1))/100
25290 '
25300 'Calculate Coefficient Determinant CD
25310 '
25320 CD=XAxis(1)*(YAxis(2)*ZAxis(3)-YAxis(3)*ZAxis(2))
25330 CD=CD-XAxis(2)*(YAxis(1)*ZAxis(3)-YAxis(3)*ZAxis(1))
25340 CD=CD+XAxis(3)*(YAxis(1)*ZAxis(2)-YAxis(2)*ZAxis(1))
25350 '
25360 'Calculate Determinant XD
25370 '
25380 XD=Focal(1)*(YAxis(2)*ZAxis(3)-YAxis(3)*ZAxis(2))
25390 XD=XD-Focal(2)*(YAxis(1)*ZAxis(3)-YAxis(3)*ZAxis(1))
25400 XD=XD+Focal(3)*(YAxis(1)*ZAxis(2)-YAxis(2)*ZAxis(1))
25410 '
25420 'Calculate Determinant YD
25430 '
25440 YD=XAxis(1)*(Focal(2)*ZAxis(3)-Focal(3)*ZAxis(2))
25450 YD=YD-XAxis(2)*(Focal(1)*ZAxis(3)-Focal(3)*ZAxis(1))
25460 YD=YD+XAxis(3)*(Focal(1)*ZAxis(2)-Focal(2)*ZAxis(1))
25470 '
25480 'Calculate Determinant ZD
25490 '
25500 ZD=XAxis(1)*(YAxis(2)*Focal(3)-YAxis(3)*Focal(2))
25510 ZD=ZD-XAxis(2)*(YAxis(1)*Focal(3)-YAxis(3)*Focal(1))
25520 ZD=ZD+XAxis(3)*(YAxis(1)*Focal(2)-YAxis(2)*Focal(1))
25530 '
25540 'Calculate the Factors
25550 '
25560 XFactor=XD/CD
25570 YFactor=YD/CD
25580 ZFactor=ZD/CD
25590
25600 RETURN
30000 '
30010 'Subroutine: Relative Normal Point Position
```

```
30020 '
30030 'This subroutine calculates the factors with which the vectors XAxis, YAxis
30040 'and ZAxis have to be multiplied in order to go from sparkgap#1 to the nor-
30050 'mal point.
30060 '
30070 'Programmer: Johann Kettenberger
30080 '
30090 'Date: September 14, 1985
30100 '
30110 '*** Start of Subroutine ****************************************************
30120 '
30130 'Save the current Sparkgap Coordinates
30140 '
30150 FOR Gap=1 TO 3
30160   FOR Coord=1 TO 3
30170     StoreGap(Gap,Coord)=GapCoord(Gap,Coord)
30180   NEXT Coord
30190 NEXT Gap
30200 '
30210 'User Guidance
30220 '
30230 PRINT
30240 PRINT"Please put the microscope in its low position for the determination
30250 PRINT"of the optical axis."
30260
30270 FOR GapToFire=1 TO 3
30280   GOSUB 10000
30290 NEXT GapToFire
30300 '
30310 'Determine the Coordinates of the Sparkgaps in the Microphone system
30320 '
30330 GOSUB 20000
30340 '
30350 'Determine the Coordinates of the Normal Point in the Microphone system
30360 '
30370 GOSUB 35000
30380 '
30390 'Calculate the Factors for XAxis, YAxis and ZAxis
30400 '
30410 FOR Gap=1 TO 3
30420   FOR Coord=1 TO 3
30430     GapCoord(Gap,Coord)=StoreGap(Gap,Coord)
30440   NEXT Coord
30450 NEXT Gap
30460 '
30470 'Calculate the Vector Sparkgap#1 - Normal Point
30480 '
30490 Focal(1)=Focal(1)-GapCoord(1,1)
30500 Focal(2)=Focal(2)-GapCoord(1,2)
30510 Focal(3)=Focal(3)-GapCoord(1,3)
30520 '
30530 'Determine relative Normal Point Position
30540 '
30550 GOSUB 25000
30560 '
30570 'Store the Result
30580 '
30590 XFac(2)=XFactor
30600 YFac(2)=YFactor
30610 ZFac(2)=ZFactor
30620
30630 RETURN
35000 '
35010 'Subroutine: Absolut Focal Point Coordinates
35020 '
35030 'This subroutine calculates the coordinates of the focal point in the
35040 'absolute microphone coordinate system
35050 '
35060 'Programmer: Johann Kettenberger
35070 '
35080 'Date: September 14, 1985
35090 '
35100 '*** Start of Subroutine ****************************************************
35110 '
35120 'Calculate XAxis, YAxis and ZAxis Vectors
35130 '
35140 FOR Coord=1 TO 3
35150   XAxis(Coord)=GapCoord(3,Coord)-GapCoord(1,Coord)
35160   YAxis(Coord)=GapCoord(2,Coord)-GapCoord(1,Coord)
35170 NEXT Coord
35180
35190 ZAxis(1)=(XAxis(2)*YAxis(3)-XAxis(3)*YAxis(2))/100
35200 ZAxis(2)=(XAxis(3)*YAxis(1)-XAxis(1)*YAxis(3))/100
35210 ZAxis(3)=(XAxis(1)*YAxis(2)-XAxis(2)*YAxis(1))/100
35220 '
35230 'Calculate the Focal Point Coordinates
35240 '
35250 FOR Coord=1 TO 3
35260   Focal(Coord)=GapCoord(1,Coord)+XFac(1)*XAxis(Coord)+YFac(1)*YAxis(Coord)+ZFac(1)*ZAxis(Coord)
35270 NEXT Coord
35280
35290 RETURN
40000 '
40010 'Subroutine: Relative Orientation Point Position
```

```
40020 '
40030 'This subroutine calculates the factors with which the vectors XAxis, YAxis
40040 'and ZAxis have to be multiplied. The orientation point is the projection
40050 'of sparkgap#1 onto the focal plane.
40060 '
40070 'Programmer: Johann Kettenberger
40080 '
40090 'Date: September 14, 1985
40100 '
40110 '*** Start of Subroutine *********************************************
40120 '
40130 'Calculate the Focal Point Coordinates
40140 '
40150 GOSUB 35000
40160 '
40170 'Determine the coordinates of the point in the middle between gaps 2&3
40180 '
40190 FOR Coord=1 TO 3
40200   Orient(Coord)=GapCoord(1,Coord)-Focal(Coord)
40210 NEXT Coord
40220 '
40230 'Calculate the Normal of the Focal Plane
40240 '
40250 FOR Coord=1 TO 3
40260   Normal(Coord)=GapCoord(1,Coord)+XFac(2)*XAxis(Coord)+YFac(2)*YAxis(Coord)+ZFac(2)*ZAxis(Coord)
40270   Normal(Coord)=Focal(Coord)-Normal(Coord)
40280 NEXT Coord
40290 '
40300 'Calculate Projection of Orient vector onto Focal Plane
40310 '
40320 Vec1(1,1)=(Orient(2)*Normal(3)-Orient(3)*Normal(2))/10
40330 Vec1(1,2)=(Orient(3)*Normal(1)-Orient(1)*Normal(3))/10
40340 Vec1(1,3)=(Orient(1)*Normal(2)-Orient(2)*Normal(1))/10
40350 '
40360 Orient(1)=(Normal(2)*Vec1(1,3)-Normal(3)*Vec1(1,2))/10+Focal(1)
40370 Orient(2)=(Normal(3)*Vec1(1,1)-Normal(1)*Vec1(1,3))/10+Focal(2)
40380 Orient(3)=(Normal(1)*Vec1(1,2)-Normal(2)*Vec1(1,1))/10+Focal(3)
40390 '
40400 'Calculate the vector Sparkgap#1 - Orientation Point
40410 '
40420 FOR Coord=1 TO 3
40430   Focal(Coord)=Orient(Coord)-GapCoord(1,Coord)
40440 NEXT Coord
40450 '
40460 'Determine the relative Orientation Point Position
40470 '
40480 GOSUB 25000
40490 '
40500 'Store the Result
40510 '
40520 XFac(3)=XFactor
40530 YFac(3)=YFactor
40540 ZFac(3)=ZFactor
40550 '
40560 RETURN
```

Appendix D

```
100 'Program REG: Spatial Registration of the Fiducials
110 '
120 'This program determines the coordinates of the fiducials in the microphone
130 'coordinate system. Additionally the fiducials are known in the testblock
140 'coordinate space and this allows to compute the conversion matrix which
150 'transforms the coordinates of a point known in the microphone system into
160 'testblock coordinates.
170 '
180 'Programmer: Johann Kettenberger
```

```
190 '
200 'Date: September 17, 1985
210 '
220 OPTION Base 1                    'start array indices with 1 instead of 0
230 '
240 '*** Array Declarations **********************************************
250 '
260 DIM MikeGapSlant(4,3,300)        'holds slantranges; 1.index: microphone,
270                                  '2.index: sparkgap, 3.index: # of slantranges
280                                  'to be collected (Max = 300)
290 DIM SlantMean(4,3)               'holds mean slantranges calculated from the
300                                  'slantranges in MikeGapSlant; 1 index: micro-
310                                  'phone, 2.index: sparkgap
320 DIM Class(7)                     'histogram classes for the statistical analysis
330                                  'of the slantrange distribution
340 DIM Focal(3)                     'coordinates of 4. sparkgap (focal point) in
350                                  'the microphone coordinate system
360 DIM MikeDist(4,3)                'distances between microphones, 1 index: micro-
370                                  'phone being shut off, 2.index: 1=distance ori-
380                                  'gin microphone - X-axis microphone, 2=distance
390                                  'origin microphone - Y-axis microphone, 3= dis-
400                                  'tance X-axis - Y-axis microphone
410 DIM Index(4,3)                   'changes indices depending on which microphone
420                                  'is shut off. This allows to use the same for-
430                                  'mulas independent of the microphone being shut
440                                  'off. 1.index: microphone shut off, 2.index:
450                                  '1=X-axis microphone, 2=Origin microphone,
460                                  '3=Y-axis microphone
470 DIM CosA(4)                      'cosine of angle between X-axis and Y-axis mi-
480                                  'crophone at origin. Index: microphone shut off
490 DIM SinA(4)                      'sine of the angle described above
500 DIM GapCoord(3,3)                'coordinates of sparkgaps in microphone system
510                                  '1.index: sparkgap, 2.index: coordinate (1=X,
520                                  '2=Y, 3=Z)
530 DIM GaptoCoG(3,3)                'vector from a sparkgap to the midpoint of the
540                                  'opposite sparkgap triangle side through the
550                                  'center of gravity of the triangle
560                                  '1.index: sparkgap, 2.index: coordinates
570 DIM CoG(3)                       'coordinates of center of gravity of sparkgap
580                                  'triangle
590 DIM DisG(3)                      'distances from center of gravity to sparkgaps
600 DIM TriNorm(3)                   'normal vector of sparkgap triangle
610 DIM Vec1(3,3)                    'auxiliary vector needed for determining the
620                                  'correct positions of the sparkgaps
630                                  '1.index: sparkgap, 2.index: coordinates
640 DIM Vec2(3,3)                    'as Vec1
650 DIM NewGap(3,3,3)                'set of corrected sparkgap coordinates
660                                  '1.index: sparkgap chosen to orient corrected
670                                  'sparkgap triangle, 2.index: sparkgap,
680                                  '3.index: coordinates
690 DIM NormVec1(3)                  'factors to normalize vectors Vec1
700 DIM NormVec2(3)                  'factors to normalize vectors Vec2
710 DIM Mike(4,3,3)                  'microphone coordinates depending on which one
720                                  'is shut off. 1.index: microphone shut off,
730                                  '2.index: 1=X-axis microphone, 2=Origin micro-
740                                  'phone, 3=Y-axis microphone, 3.index: coord's
750 DIM StoreGap(3,3)                'sparkgap coordinates when microscope is
760                                  'focused on 4. sparkgap. 1.index: sparkgap,
770                                  '2.index: coordinate
780 DIM NewCoord(3,3)                'improved sparkgap coordinates calculated from
790                                  'improved slantranges. 1.index: sparkgap,
800                                  '2.index: coordinates
810 DIM XAxis(3)                     'X-axis of oblique sparkgap based system to de-
820                                  'termine the relative position of focal, normal
830                                  'and orientation point. X-axis goes from spark-
840                                  'gap#1 (origin) to sparkgap#3
850 DIM YAxis(3)                     'goes from sparkgap#1 to sparkgap#2
860 DIM ZAxis(3)                     'cross product of XAxis x YAxis
870 DIM XFac(3)                      'factors with which XAxis,YAxis,ZAxis vectors
880 DIM YFac(3)                      'have to be multiplied to go from sparkgap#1
890 DIM ZFac(3)                      'to the focal(index=1), normal(index=2) or
900                                  'orientation point(index=3)
910 DIM Dif(3)                       'differences between successive calcu-
920                                  'lations of sparkgap coordinates
930 DIM Orient(3)                    'Orientation point coordinates
940 DIM Normal(3)                    'Normal vector of the focal plane
950 DIM Fiducial(3,3)                'Fiducial coordinates in microphone system
960                                  '1.index: fiducial, 2.index: coordinate
970 DIM TestPoint(5,3)               'Coordinates of test points in the test
980                                  'block coordinate system. 1.index: test point
990                                  '2.index: coordinate
1000 DIM FidPoint(3,3)               'Fiducial coordinates in the test block
1010                                 'coordinate system. 1.index: fiducial
1020                                 '2.index: coordinates
1030 DIM Test(3)                     'coordinates of currently selected test point
1040 DIM E(4)                        'Errors between true and measured test point
1050                                 'coordinates (subscripts 1-3) and total error
1060                                 '(subscript 4)
1070 DIM TranMat(2,4,3)              'coefficients for coordinate transformation
1080                                 'between microphone and test block system
1090                                 '1.index: 1=transformation of microphone
1100                                 'coordinates into test block coordinates
1110                                 '2=transformation of test block coordinates
1120                                 'into microphone coordinates. 2 index:
1130                                 '1-3=unity vectors; 4=origin
1140                                 '3.index: coordinates
1150 DIM FidToCoG(3,3)               'as GapToCoG only now the vectors refer to the
1160                                 'fiducial triangle
1170 DIM NewFid(3,3,3)               'as NewGap but now refering to fiducial triangle
```

```
1180 DIM NewSpark(3,3,3)              'improved sparkgap coordinates resulting from
1190                                  'the improved fiducial coordinates.
1200                                  '1. index: fiducial determining the orientation
1210                                  'of the fiducial triangle; 2. index: sparkgap;
1220                                  '3. index: coordinates
1230 DIM Axis(3,3,3)                  'Vectors needed to calculate the location
1240                                  'of the sparkgaps once the improved fiducials
1250                                  'are determined. 1. index: fiducial; 2. index:
1260                                  'axis 1=XAxis, 2=YAxis, 3=ZAxis; 3. index: co-
1270                                  'ordinates
1280 DIM CFid(3,3)                    'corrected fiducial coordinates. 1. index: fi-
1290                                  'ducial; 2. index: coordinates
1300 DIM DisF(3)                      'distances from the center of gravity of
1310                                  'the fiducial triangle to the fiducials
1320 DIM AuxVec(3)                    'auxiliary vector for coordinate trans-
1330                                  'formation
1340 DIM MiCo(4,3)                    'microphone coordinates as calculated
1350                                  'from the sparkgap triangle in order to
1360                                  'determine the microphone distances
1370 '
1380 '*** Array Initializations and Constants *****************************
1390 '
1400 'Order of Index Permutation
1410 '
1420 Index(1,1)=4:  Index(1,2)=3:  Index(1,3)=2
1430 Index(2,1)=1:  Index(2,2)=4:  Index(2,3)=3
1440 Index(3,1)=2:  Index(3,2)=1:  Index(3,3)=4
1450 Index(4,1)=3:  Index(4,2)=2:  Index(4,3)=1
1460 '
1470 'Measured Microphone Distances
1480 '
1490 MikeDist(1,1)=96.243:  MikeDist(1,2)=100.209:  MikeDist(1,3)=137.754  '[cm]
1500 MikeDist(2,1)=101.965: MikeDist(2,2)=96.243:  MikeDist(2,3)=140.962
1510 MikeDist(3,1)=95.697:  MikeDist(3,2)=101.965: MikeDist(3,3)=137.754
1520 MikeDist(4,1)=100.289: MikeDist(4,2)=95.697:  MikeDist(4,3)=140.962
1530 '
1540 'Cosine/Sine of Angle at Origin of Microphone Coordinate System
1550 '
1555 FOR Mik=1 TO 4
1560 CosA(Mik)=MikeDist(Mik,1)^2+MikeDist(Mik,2)^2-MikeDist(Mik,3)^2
1570 CosA(Mik)=CosA(Mik)/(2*MikeDist(Mik,1)*MikeDist(Mik,2))
1580 SinA(Mik)=SQR(1-CosA(Mik)*CosA(Mik))
1585 NEXT Mik
1590 '
1600 'Distances from the Center of Gravity of the Sparkgap Triangle to the Sparkgaps
1610 '
1620 DisG(1)=17.341285:  DisG(2)=17.204482:  DisG(3)=17.231647
1630 '
1640 'Angles needed to calculate corrected Sparkgap Positions
1650 '
1660 CosA12=0.4968336:  SinA12=0.8678458
1670 CosA13=0.5030557 : SinA13=0.8637878
1680 CosA21=0.4926918 : SinA21=0.8702039
1690 CosA23=0.4959331:  SinA23=0.8683607
1700 CosA31=0.5071646:  SinA31=0.8618492
1710 CosA32=0.5031794:  SinA32=0.864182
1720 '
1730 'Microphone Coordinates
1740 '
1745 FOR Mik=1 TO 4
1750 Mike(Mik,1,1)=MikeDist(Mik,1): Mike(Mik,1,2)=0:  Mike(Mik,1,3)=0
1760 Mike(Mik,2,1)=0: Mike(Mik,2,2)=0: Mike(Mik,2,3)=0
1770 Mike(Mik,3,1)=MikeDist(Mik,2)*CosA(Mik): Mike(Mik,3,2)=MikeDist(Mik,2)*SinA(Mik): Mike(Mik,3,3)=0
1775 NEXT Mik
1780 '
1790 'Test Block Coordinates of the Fiducials,
1800 '
1810 FidPoint(1,1)=0:  FidPoint(1,2)=0:  FidPoint(1,3)=0
1820 FidPoint(2,1)=-1.671: FidPoint(2,2)=7.62:  FidPoint(2,3)=4.854
1830 FidPoint(3,1)=1.016:  FidPoint(3,2)=15.867: FidPoint(3,3)=-1.75
1840 '
1850 'Test Block Coordinates of the Test Points
1860 '
1870 TestPoint(1,1)=-4.719:  TestPoint(1,2)=7.62:  TestPoint(1,3)=0.79
1880 TestPoint(2,1)=2.54  : TestPoint(2,2)=0   :  TestPoint(2,3)=0
1890 TestPoint(3,1)=5.949 : TestPoint(3,2)=7.62:  TestPoint(3,3)=4.854
1900 TestPoint(4,1)=6.096 : TestPoint(4,2)=0.247: TestPoint(4,3)=0
1910 TestPoint(5,1)=1.016 : TestPoint(5,2)=15.867: TestPoint(5,3)=.226
1920 '
1930 '*** Start of Main Program ***************************************
1940 '
1950 ON ERROR GOTO 4210               'avoid program crash for forseeable errors
1960 '
1970 'Print the Program Header
1980 '
1990 PRINT
2000 PRINT"Program TESTREG: Test of the registration system on the test block
2010 PRINT
2020 PRINT"Version 0.1"
2030 PRINT
2040 '
2050 'Read in the data from the file FPL.DAT if present
2060 '
2070 OPEN "Fpl.Dat" FOR INPUT AS #1
2080    INPUT#1, Datum$
2090    INPUT#1, Zeit$
2100    INPUT#1, ShutOffMike
2110    INPUT#1, Sparks
2120    FOR PlanePoint=1 TO 3
```

```
2130      INPUT#1, XFac(PlanePoint)
2140      INPUT#1, YFac(PlanePoint)
2150      INPUT#1, ZFac(PlanePoint)
2160   NEXT PlanePoint
2170 CLOSE #1
2180 '
2190 'Inform User
2200 '
2210 PRINT
2220 PRINT"The currently available focal plane definition has been done"
2230 PRINT Datum$;" at ";Zeit$;" with microphone #";ShutOffMike;" shut off and"
2240 PRINT Sparks;" Sparks fired per sparkgap."
2250 PRINT"Do you want to use this focal plane data [y/n]";
2260 INPUT Answer$
2270 IF (Answer$="n") OR (Answer$="N") THEN GOTO 4380
2280 IF (Answer$="y") OR (Answer$="Y") THEN GOTO 2320
2290 PRINT"Please answer 'y' or 'n'"
2300 GOTO 2260
2310 '
2320 'Read in the data from the file TRANMAT.DAT if present
2330 '
2340 OPEN "TranMat.Dat" FOR INPUT AS #1
2350    INPUT#1, Datum$
2360    INPUT#1, Zeit$
2370    INPUT#1, ShutOffMike
2380    FOR Case=1 TO 2
2390      FOR Ax=1 TO 4
2400        FOR Coord=1 TO 3
2410          INPUT#1, TranMat(Case,Ax,Coord)
2420        NEXT Coord
2430      NEXT Ax
2440    NEXT Case
2450 CLOSE #1
2460 '
2470 'Inform User
2480 '
2490 PRINT
2500 PRINT"It is possible to skip the registration procedure by using the"
2510 PRINT"transformation matrices calculated at ";Zeit$;" on ";Datum$
2520 PRINT"Are those matrices still valid [y/n]";
2530 INPUT Answer$
2540 IF (Answer$="y") OR (Answer$="Y") THEN OPEN "Reg.Log" FOR OUTPUT AS #2: GOTO 3480
2550 IF (Answer$="n") OR (Answer$="N") GOTO 2590
2560 PRINT"Please answer with 'y' or 'n'"
2570 GOTO 2530
2580 '
2590 'Start of Registration of Fiducials
2600 '
2610 PRINT
2620 PRINT"Which microphone do you want to be ignored [1-4]";
2630 INPUT ShutOffMike
2640 IF (ShutOffMike<1) OR (ShutOffMike>4) GOTO 2610
2650 IF ShutOffMike<>1 THEN PRINT"Sorry, but at the moment can only microphone #1 be switched off": GOTO 2610
2660 PRINT
2670 PRINT"How many sparks per sparkgap do you want to fire [Max.=300]";
2680 INPUT Sparks
2690 IF (Sparks<1) OR (Sparks>300) GOTO 2670
2700 PRINT
2710 PRINT"Please locate the test block under the microscope and focus on"
2720 PRINT"the fiducials successively."
2730 '
2740 'Open the File recording the statistical Data
2750 '
2760 OPEN "Reg.Log" FOR OUTPUT AS #2
2770 OPEN "Mike.Dis" FOR OUTPUT AS #3
2780 '
2790 'Input the Slantranges of the Fiducials
2800 '
2810 FOR Fid=1 TO 3
2820
2830 PRINT
2840 PRINT"Focus on fiducial #";Fid;"please."
2850    FOR GapToFire=1 TO 3
2860      GOSUB 10000
2870    NEXT GapToFire
2880 '
2890 'Calculate the microphone distances
2900 '
2910 GOSUB 55000
2920 '
2930 'Calculate the Sparkgap Coordinates in the Microphone System
2940 '
2950    GOSUB 20000
2960 '
2970 'Calculate the Coordinates of the current Fiducial in the Microphone System
2980 '
2990    GOSUB 35000
3000 '
3010 'Store the Fiducial Coordinates
3020 '
3030    Fiducial(Fid,1)=Focal(1)
3040    Fiducial(Fid,2)=Focal(2)
3050    Fiducial(Fid,3)=Focal(3)
3060 '
3070 'Store the Vectors XAxis,YAxis,ZAxis associated with each fiducial
3080 '
3090    FOR Coord=1 TO 3
3100      Axis(Fid,1,Coord)=XAxis(Coord)
3110      Axis(Fid,2,Coord)=YAxis(Coord)
```

```
3120        Axis(Fid,3,Coord)=ZAxis(Coord)
3130     NEXT Coord
3140
3150 NEXT Fid
3160 '
3170 'Improve the Fiducial Coordinates iteratively the same way the Sparkgap
3180 'Coordinates are improved
3190 '
3200 GOSUB 5000
3210
3220 IF Again=0 GOTO 3420
3230 PRINT
3240 PRINT"The fiducial coordinates did not converge after 10 iterations."
3250 PRINT"The differences between the last two fiducial locations"
3260 PRINT"calculated are:"
3270 PRINT"Fiducial#1: ";Dif(1)
3280 PRINT"Fiducial#2: ";Dif(2)
3290 PRINT"Fiducial#3: ";Dif(3)
3300 PRINT
3310 PRINT"Do you want to iterate 10 more times [i], use the current fiducial"
3320 PRINT"data [c], or stop the program [s]";
3330 INPUT Answer$
3340 IF (Answer$="i") OR (Answer$="I") GOTO 3200
3350 IF (Answer$="c") OR (Answer$="C") GOTO 3420
3360 IF (Answer$="s") OR (Answer$="S") GOTO 4360
3370 PRINT"Please answer with 'i', 'c', or 's'"
3380 GOTO 3330
3390 '
3400 'Calculate the Matrix converting Microphone into Test Block Coordinates
3410 'and vice versa
3420 '
3430 GOSUB 45000
3440 '
3450 'Focus on chosen Test Points and determine the Error between true and
3460 'calculated Test Point Coordinates
3470 '
3480    Testing=1
3490 WHILE Testing
3500    PRINT
3510    PRINT"Choose a test point please [T1-T5 or F1-F3]";
3520    INPUT Point$
3530    IF (Point$="T1") OR (Point$="t1") THEN P=1: GOTO 3660
3540    IF (Point$="T2") OR (Point$="t2") THEN P=2: GOTO 3660
3550    IF (Point$="T3") OR (Point$="t3") THEN P=3: GOTO 3660
3560    IF (Point$="T4") OR (Point$="t4") THEN P=4: GOTO 3660
3570    IF (Point$="T5") OR (Point$="t5") THEN P=5: GOTO 3660
3580    IF (Point$="F1") OR (Point$="f1") THEN P=1: GOTO 3620
3590    IF (Point$="F2") OR (Point$="f2") THEN P=2: GOTO 3620
3600    IF (Point$="F3") OR (Point$="f3") THEN P=3: GOTO 3620
3610    GOTO 3510
3620    FOR Coord=1 TO 3
3630       Test(Coord)=FidPoint(P,Coord)
3640    NEXT Coord
3650    GOTO 3690
3660    FOR Coord=1 TO 3
3670       Test(Coord)=TestPoint(P,Coord)
3680    NEXT Coord
3690    PRINT
3700    PRINT"Focus on test point ";Point$
3710 '
3720 'Input the Slantranges
3730 '
3740    FOR GapToFire=1 TO 3
3750       GOSUB 10000
3760    NEXT GapToFire
3770 '
3780 'Calculation of the microphone distances
3790 '
3800 GOSUB 55000
3810 '
3820 'Calculate the Sparkgap Coordinates
3830 '
3840    GOSUB 20000
3850 '
3860 'Calculate the Test Point Coordinates in the Microphone System
3870 '
3880    GOSUB 35000
3890 '
3900 'Convert the calculated Test Point Coordinates into the Test Block System
3910 '
3920 Case=1
3930    GOSUB 50000
3940 '
3950 'Determine the Discrepancies between the true and measured Point Coordinates
3960 '
3970    E(4)=0
3980    FOR Coord=1 TO 3
3990       E(Coord)=Focal(Coord)-Test(Coord)
4000       E(4)=E(4)+E(Coord)*E(Coord)
4010    NEXT Coord
4020    E(4)=SQR(E(4))
4030 '
4040 'Display the Errors
4050 '
4060    PRINT
4070    PRINT"The errors for the different coordinates are:"
4080    PRINT"X: ";E(1)*10;"mm"
4090    PRINT"Y: ";E(2)*10;"mm"
4100    PRINT"Z: ";E(3)*10;"mm"
4110    PRINT
```

```
4120    PRINT"The total error between measured and true test point is ";E(4)*10;"mm"
4130    PRINT
4140    PRINT"Enter 'c' to continue; 's' to stop the program";
4150    INPUT Answer$
4160    IF (Answer$="s") OR (Answer$="S") THEN Testing=0
4170  '
4180 WEND
4190 GOTO 4360
4200 '
4210 'Error handling Routine
4220 '
4230 IF (Err=53) AND (Erl=2070) THEN PRINT"The file FPL.DAT does not exist. The registration": PRINT"procedure
     cannot be done without it.": PRINT"Please run the program FPL to create the file FPL.DAT.": GOTO 4380
4240 '
4250 IF (Err=62) AND (Erl<2160) THEN PRINT"The file FPL.DAT is incomplete. Please run the program": PRINT"FPL
     to create a new complete file.": GOTO 4380
4260 '
4270 IF (Err=53) AND (Erl=2340) GOTO 2590
4280 '
4290 IF (Err=62) AND (Erl<2420) GOTO 2590
4300 '
4310 IF (Err=57) AND (Erl<10490) THEN PRINT: PRINT"The communication with the digitizer failed.": PRINT"The
     program has been reset and restarted.": GapToFire=1: GOTO 10210
4320 '
4330 ON ERROR GOTO 0  'For all the Errors not trapped here
4340
4350
4360 CLOSE #2
4370 CLOSE #3
4380 END
5000 '
5010 'Subroutine: Iterative Improvement of Fiducial Locations
5020 '
5030 'This subroutine improves the fiducial coordinates using the same approach
5040 'as was used previously for improving the sparkgap coordinates.
5050 'Now the iteration goes one step further because both the sparkgap triangles
5060 'associated with each fiducial as well as the fiducial triangle have to
5070 'match their counterparts known through measurement (sparkgap triangle) or
5080 'from testblock coordinates (fiducial triangle).
5090 '
5100 'Programmer: Johann Kettenberger
5110 '
5120 'Date: September 21, 1985
5130 '
5140 '*** Start of Subroutine ***********************************************
5150 '
5160 'Determine the data defining the fiducial triangle
5170 '
5180 GOSUB 30000
5190 '
5200 'Start the iteration
5210 '
5220 Inaccurate=1
5230
5240 WHILE Inaccurate
5250 '
5260 'Calculate the improved fiducial coordinates resulting from locating the
5270 'correct fiducial triangle at the center of gravity of the through the
5280 'acoustic system determined triangle and orienting it via the vectors from
5290 'the fiducial position through the center of gravity.
5300 '
5310    GOSUB 40000
5320 '
5330 'Calculate the three sets of improved sparkgap coordinates belonging to
5340 'the current fiducial
5350 '
5360    FOR Fid=1 TO 3
5370      FOR Orient=1 TO 3
5380        FOR Coord=1 TO 3
5390          NewSpark(Orient,1,Coord)=NewFid(Orient,Fid,Coord)-XFac(1)*Axis(Fid,1,Coord)-YFac(1)*Axis(Fid,2,
       Coord)-ZFac(1)*Axis(Fid,3,Coord)
5400          NewSpark(Orient,2,Coord)=NewSpark(Orient,1,Coord)+Axis(Fid,2,Coord)
5410          NewSpark(Orient,3,Coord)=NewSpark(Orient,1,Coord)+Axis(Fid,1,Coord)
5420        NEXT Coord
5430      NEXT Orient
5440
5450 '
5460 'Calculate the set of slantranges resulting from the improved sparkgaps
5470 '
5480    FOR Gap=1 TO 3
5490      FOR Micro=1 TO 3
5500        SlantMean(Index(ShutOffMike,Micro),Gap)=0
5510        FOR Orient=1 TO 3
5520          NewSlant=0
5530          FOR Coord=1 TO 3
5540            NewSlant=NewSlant+(Mike(ShutOffMike,Micro,Coord)-NewSpark(Orient,Gap,Coord))^2
5550          NEXT Coord
5560          NewSlant=SQR(NewSlant)
5570          SlantMean(Index(ShutOffMike,Micro),Gap)=SlantMean(Index(ShutOffMike,Micro),Gap)+NewSlant
5580        NEXT Orient
5590        SlantMean(Index(ShutOffMike,Micro),Gap)=SlantMean(Index(ShutOffMike,Micro),Gap)/3
5600      NEXT Micro
5610    NEXT Gap
5620 '
5630 'Calculate the corrected sparkgap coordinates determined by the new slantranges
5640 '
5650    GOSUB 20000
5660 '
5670 'Calculate the fiducial coordinates from the corrected sparkgaps
```

```
5680 '
5690     GOSUB 35000
5700 '
5710 'Store the corrected fiducial coordinates
5720 '
5730     CFid(Fid,1)=Focal(1)
5740     CFid(Fid,2)=Focal(2)
5750     CFid(Fid,3)=Focal(3)
5760 '
5770 'Store the axis vectors for the next iteration step
5780 '
5790     FOR Coord=1 TO 3
5800        Axis(Fid,1,Coord)=XAxis(Coord)
5810        Axis(Fid,2,Coord)=YAxis(Coord)
5820        Axis(Fid,3,Coord)=ZAxis(Coord)
5830     NEXT Coord
5840
5850   NEXT Fid
5860 '
5870 'Determine if the iteration can be stopped
5880 '
5890   FOR Fid=1 TO 3
5900     Dif(Fid)=0
5910     FOR Coord=1 TO 3
5920       Dif(Fid)=Dif(Fid)+(CFid(Fid,Coord)-Fiducial(Fid,Coord))^2
5930     NEXT Coord
5940     Dif(Fid)=SQR(Dif(Fid))
5950   NEXT Fid
5960
5970   IF (Dif(1)<.01) AND (Dif(2)<.01) AND (Dif(3)<.01) THEN Inaccurate=0
5980 '
5990 'Store the corrected fiducial positions
6000 '
6010   FOR Fid=1 TO 3
6020     FOR Coord=1 TO 3
6030       Fiducial(Fid,Coord)=CFid(Fid,Coord)
6040     NEXT Coord
6050   NEXT Fid
6060
6070 WEND
6080
6090 RETURN
10000 '
10010 'Subroutine: Slantrange Input
10020 '
10030 'This subroutine inputs the slantranges measured by the ultrasonic digitizer
10040 'via the RS-232 serial port of the IBM XT. The parallel port of the IBM XT
10050 'is used to set the sparkgap multiplexer.
10060 '
10070 'Programmer: John F. Hatch (William J. Murray, Johann Kettenberger)
10080 '
10090 'Date: September 11, 1985
10100 '
10110 '*** Start of Subroutine *****************************************************
10120 '
10130 IF GapToFire <> 1 GOTO 10210     'decide whether or not to display message
10140 PRINT
10150 PRINT"*** Press any key when ready ***"
10160 AnyKey$=INKEY$
10170 IF AnyKey$="" GOTO 10160
10180 '
10190 'Translate the Gap to be fired into the proper Multiplexer Code
10200 '
10210 IF GapToFire=1 THEN MuxCode=0
10220 IF GapToFire=2 THEN MuxCode=2
10230 IF GapToFire=3 THEN MuxCode=1
10240 '
10250 'Set the Multiplexer via the parallel Port
10260 '
10270 OUT &H3BC,MuxCode       'H3BC: hexadecimal address of parallel port
10280 '
10290 'Set serial Port for Digitizer Communication
10300 '
10310 OPEN "COM1:9600,0,7,1" AS #1
10320 '
10330 'Search for ASCII line feed in incoming data
10340 '
10350 InData$="a"
10360 WHILE (ASC(InData$)<>10)
10370    InData$=INPUT$(1,#1)
10380 WEND
10390 '
10400 'Ignore the first Set of Data
10410 '
10420 InData$=INPUT$(26,#1)
10430 '
10440 'Collect the Slantranges from the current Sparkgap
10450 '
10460 FOR I=1 TO Sparks
10470    IF LOC(1)>200 THEN OUT &H3FC,10 ELSE OUT &H3FC,11 'avoid comm.buffer overflow
10480    InData$=INPUT$(26,#1) 'input the slantranges
10490    FOR J=1 TO 4          'convert the strings into real numbers
10500      IF J=ShutOffMike GOTO 10550
10510      Value$=MID$(InData$,(J*6-5),6)
10520      Whole$=LEFT$(Value$,3)
10530      Decimal$=RIGHT$(Value$,3)
10540      MikeGapSlant(J,GapToFire,I)=Val(Whole$+"."+Decimal$)
10550    Next J
10560 NEXT I
```

```
10570 CLOSE #1      'suppress communication
10580 '
10590 'Analyze the Slantrange Data statistically
10600 '
10610 Repeat=0
10620 GOSUB 15000
10630 '
10640 'Check if the Data are o.k.
10650 '
10660 IF Repeat=1 THEN Print"Slantranges between microphone ";Mike;" and sparkgap#";GapToFire;" are greater
      than 200cm.": PRINT"Try again": GOTO 10140
10670 IF Repeat=2 THEN PRINT"Too much variance in slantranges between microphone ";Mike;" and sparkgap#";
      GapToFire: PRINT"Try again": GOTO 10140
10680 '
10690 'Store the Mean Slantranges and add the Counter Delay
10700 '
10710 FOR Mike=1 TO 4
10720    SlantMean(Mike,GapToFire)=SlantMean(Mike,GapToFire)+4.45 'add counter delay
10730 NEXT Mike
10740 '
10750 RETURN
15000 '
15010 'Subroutine: Statistical Analysis of Slantrange Data
15020 '
15030 'This subroutine calculates the mean from the total number of slantranges
15040 'collected. It sorts out the slantranges which are +/-0.5mm off the mean
15050 'and calculates thereof an improved mean. The slantranges are classified
15060 'in a histogram which is recorded in the file 'FPL.Log'.
15070 '
15080 'Programmer: Johann Kettenberger
15090 '
15100 'Date: September 11, 1985
15110 '
15120 '*** Start of Subroutine ***********************************************
15130 '
15140 'Calculation of the 1. Estimate of the Mean
15150 '
15160 FOR Mike=1 TO 4
15170    IF Mike=ShutOffMike GOTO 15720
15180    SortedOut=0
15190    SlantSum=0
15200    FOR I=1 TO Sparks
15210       IF MikeGapSlant(Mike,GapToFire,I)<245 THEN SlantSum=SlantSum+MikeGapSlant(Mike,GapToFire,I)
          ELSE SortedOut=SortedOut+1
15220    NEXT I
15230    IF SortedOut>(0.1*Sparks) THEN Repeat=1: GOTO 15730
15240    SlantMean(Mike,GapToFire)=SlantSum/(Sparks-SortedOut)
15250 '
15260 'Calculation of the Standard Deviation
15270 '
15280    SlantSum=0
15290    FOR I=1 TO Sparks
15300       IF MikeGapSlant(Mike,GapToFire,I)<245 THEN SlantSum=SlantSum+(MikeGapSlant(Mike,GapToFire,I)-
          SlantMean(Mike,GapToFire))^2
15310    NEXT I
15320    StdDev=SlantSum/(Sparks-SortedOut)
15330 '
15340 'Calculation of improved Mean
15350 '
15360    SortedOut=0
15370    SlantSum=0
15380    FOR I=1 TO Sparks
15390       Dif=ABS(MikeGapSlant(Mike,GapToFire,I)-SlantMean(Mike,GapToFire))
15400       IF Dif<0.05 THEN SlantSum=SlantSum+MikeGapSlant(Mike,GapToFire,I) ELSE SortedOut=SortedOut+1
15410    NEXT I
15420    IF SortedOut>(0.3*Sparks) THEN Repeat=2: GOTO 15730
15430    SlantMean(Mike,GapToFire)=SlantSum/(Sparks-SortedOut)
15440 '
15450 'Classification of the Slantranges in the Histogram
15460 '
15470    FOR I=1 TO 7
15480       Class(I)=0
15490    NEXT I
15500
15510    FOR I=1 TO Sparks
15520       IF MikeGapSlant(Mike,GapToFire,I)>(SlantMean(Mike,GapToFire)+.05) THEN Class(1)=Class(1)+1: GOTO 15590
15530       IF MikeGapSlant(Mike,GapToFire,I)>(SlantMean(Mike,GapToFire)+.03) THEN Class(2)=Class(2)+1: GOTO 15590
15540       IF MikeGapSlant(Mike,GapToFire,I)>(SlantMean(Mike,GapToFire)+.01) THEN Class(3)=Class(3)+1: GOTO 15590
15550       IF MikeGapSlant(Mike,GapToFire,I)>(SlantMean(Mike,GapToFire)-.01) THEN Class(4)=Class(4)+1: GOTO 15590
15560       IF MikeGapSlant(Mike,GapToFire,I)>(SlantMean(Mike,GapToFire)-.03) THEN Class(5)=Class(5)+1: GOTO 15590
15570       IF MikeGapSlant(Mike,GapToFire,I)>(SlantMean(Mike,GapToFire)-.05) THEN Class(6)=Class(6)+1: GOTO 15590
15580       Class(7)=Class(7)+1
15590    NEXT I
15600 '
15610 'Record Histogram
15620 '
15630    PRINT #2, GapToFire
15640    PRINT #2, Mike
15650    PRINT #2, Sparks
15660    PRINT #2, SlantMean(Mike,GapToFire)
15670    PRINT #2, StdDev
15680    FOR I=1 TO 7
15690       PRINT #2, Class(I)
15700    NEXT I
15710
15720 NEXT Mike
15730
15740 RETURN
20000 '
```

```
20010 'Subroutine: Sparkgap Coordinates
20020 '
20030 'This subroutine calculates the coordinates of the sparkgaps in the micro-
20040 'phone system. An iterative procedure is used to correct for random errors
20050 'in the slantranges.
20060 'The iteration starts by calculating the sparkgap positions. It checks then
20070 'if the calculated sparkgap positions form a triangle which corresponds to
20080 'the triangle known from measurements of the distances between the spark-
20090 'gaps. If this is not the case, then the center of gravity of the precise
20100 'sparkgap triangle is located at the center of gravity of the calculated
20110 'triangle and improved sparkgap locations are determined. The orientation
20120 'of the precise sparkgap triangle with respect to the calculated one is
20130 'given through the sparkgap-center of gravity vectors of the calculated
20140 'sparkgap triangle. Since there are three of those vectors three different
20150 'orientations of the precise sparkgap triangle are to be considered. This
20160 'results in three improved estimates of the sparkgap locations and three
20170 'sets of improved slantranges. The improved slantranges for each micro-
20180 'phone-sparkgap combination are averaged and used to compute new sparkgap
20190 'positions. This iterative refinement of the sparkgap locations goes on
20200 'until the convergence criterium is met.
20210 '
20220 'Programmer: Johann Kettenberger
20230 '
20240 'Date: September 12, 1985
20250 '
20260 '*** Start of Subroutine ************************************************
20270 '
20280 'Initial Calculation of the Sparkgap Coordinates
20290 '
20300 FOR Gap=1 TO 3
20310   GapCoord(Gap,1)=(MikeDist(ShutOffMike,1)^2+SlantMean(Index(ShutOffMike,2),Gap)^2-SlantMean(Index
      (ShutOffMike,1),Gap)^2)/(2*MikeDist(ShutOffMike,1))
20320   GapCoord(Gap,2)=(MikeDist(ShutOffMike,2)^2+SlantMean(Index(ShutOffMike,2),Gap)^2-SlantMean(Index
      (ShutOffMike,3),Gap)^2)/(2*MikeDist(ShutOffMike,2))
20330   GapCoord(Gap,2)=(GapCoord(Gap,2)-GapCoord(Gap,1)*CosA(ShutOffMike))/SinA(ShutOffMike)
20340   GapCoord(Gap,3)=-SQR(SlantMean(Index(ShutOffMike,2),Gap)^2-GapCoord(Gap,1)^2-GapCoord(Gap,2)^2)
20350 NEXT Gap
20360 '
20370 'Start Iteration
20380 '
20390 Busy=1
20400 WHILE Busy
20410 '
20420 'Calculate the Center of Gravity and the vectors from each Sparkgap through
20430 'the Center of Gravity (Orientation vectors)
20440 '
20450   FOR Coord=1 TO 3   'Center of Gravity and Orientation vector from gap#1
20460     GapToCoG(1,Coord)=GapCoord(2,Coord)+.5*(GapCoord(3,Coord)-GapCoord(2,Coord))-GapCoord(1,Coord)
20470     CoG(Coord)=GapCoord(1,Coord)+2/3*GapToCoG(1,Coord)
20480   NEXT Coord
20490   FOR Coord=1 TO 3   'Orientation vector from gap#2
20500     GapToCoG(2,Coord)=GapCoord(3,Coord)+.5*(GapCoord(1,Coord)-GapCoord(3,Coord))-GapCoord(2,Coord)
20510   NEXT Coord
20520   FOR Coord=1 TO 3   'Orientation vector from gap#3
20530     GapToCoG(3,Coord)=GapCoord(1,Coord)+.5*(GapCoord(2,Coord)-GapCoord(1,Coord))-GapCoord(3,Coord)
20540   NEXT Coord
20550 '
20560 'Calculate the improved Sparkgap Positions lying on the Orientation vectors
20570 '
20580   FOR Gap=1 TO 3
20590     FOR Coord=1 TO 3
20600       NewGap(Gap,Gap,Coord)=CoG(Coord)-GapToCoG(Gap,Coord)/SQR(GapToCoG(Gap,1)^2+GapToCoG(Gap,2)^2+Gap
      ToCoG(Gap,3)^2)*DisG(Gap)
20610     NEXT Coord
20620   NEXT Gap
20630 '
20640 'Calculate the Normal of the Sparkgap Triangle
20650 '
20660   TriNorm(1)=GapToCoG(2,2)*GapToCoG(1,3)-GapToCoG(2,3)*GapToCoG(1,2)
20670   TriNorm(2)=GapToCoG(2,3)*GapToCoG(1,1)-GapToCoG(2,1)*GapToCoG(1,3)
20680   TriNorm(3)=GapToCoG(2,1)*GapToCoG(1,2)-GapToCoG(2,2)*GapToCoG(1,1)
20690 '
20700 'Calculate Vec1 = TriNorm x GapToCoG; Vec2 = Vec1 x TriNorm
20710 '
20720   FOR Gap=1 TO 3
20730     Vec1(Gap,1)=TriNorm(2)*GapToCoG(Gap,3)-TriNorm(3)*GapToCoG(Gap,2)
20740     Vec1(Gap,2)=TriNorm(3)*GapToCoG(Gap,1)-TriNorm(1)*GapToCoG(Gap,3)
20750     Vec1(Gap,3)=TriNorm(1)*GapToCoG(Gap,2)-TriNorm(2)*GapToCoG(Gap,1)
20760     NormVec1(Gap)=SQR(Vec1(Gap,1)^2+Vec1(Gap,2)^2+Vec1(Gap,3)^2)
20770     Vec2(Gap,1)=Vec1(Gap,2)*TriNorm(3)-Vec1(Gap,3)*TriNorm(2)
20780     Vec2(Gap,2)=Vec1(Gap,3)*TriNorm(1)-Vec1(Gap,1)*TriNorm(3)
20790     Vec2(Gap,3)=Vec1(Gap,1)*TriNorm(2)-Vec1(Gap,2)*TriNorm(1)
20800     NormVec2(Gap)=SQR(Vec2(Gap,1)^2+Vec2(Gap,2)^2+Vec2(Gap,3)^2)
20810   NEXT Gap
20820 '
20830 'Calculate the improved Sparkgap Positions off the Orientation vector
20840 '
20850   FOR Coord=1 TO 3   'Orientation given by Sparkgap#1
20860     NewGap(1,2,Coord)=NewGap(1,1,Coord)+30.041*(SinA12*Vec2(1,Coord)/NormVec2(1)+CosA12*Vec1
      (1,Coord)/NormVec1(1))
20870     NewGap(1,3,Coord)=NewGap(1,1,Coord)+29.657*(SinA13*Vec2(1,Coord)/NormVec2(1)-CosA13*Vec1
      (1,Coord)/NormVec1(1))
20880   NEXT Coord
20890   FOR Coord=1 TO 3   'Orientation given by Sparkgap#2
20900     NewGap(2,1,Coord)=NewGap(2,2,Coord)+30.041*(SinA21*Vec2(2,Coord)/NormVec2(2)-CosA21*Vec1
      (2,Coord)/NormVec1(2))
20910     NewGap(2,3,Coord)=NewGap(2,2,Coord)+29.995*(CosA23*Vec1(2,Coord)/NormVec1(2)+SinA23*Vec2
      (2,Coord)/NormVec2(2))
```

```
20920     NEXT Coord
20930     FOR Coord=1 TO 3   'Orientation given by Sparkgap#3
20940        NewGap(3,1,Coord)=NewGap(3,3,Coord)+29.657*(CosA31*Vec1(3,Coord)/NormVec1(3)+SinA31*Vec2
          (3,Coord)/NormVec2(3))
20950        NewGap(3,2,Coord)=NewGap(3,3,Coord)+29.995*(SinA32*Vec2(3,Coord)/NormVec2(3)-CosA32*Vec1
          (3,Coord)/NormVec1(3))
20960     NEXT Coord
20970   '
20980   'Calculate the improved Slantranges
20990   '
21000     FOR Gap=1 TO 3
21010        FOR Micro=1 TO 3
21020           SlantMean(Index(ShutOffMike,Micro),Gap)=0
21030           FOR OGap=1 TO 3
21040              NewSlant=0
21050              FOR Coord=1 TO 3
21060                 NewSlant=NewSlant+(Mike(ShutOffMike,Micro,Coord)-NewGap(OGap,Gap,Coord))^2
21070              NEXT Coord
21080              NewSlant=SQR(NewSlant)
21090              SlantMean(Index(ShutOffMike,Micro),Gap)= SlantMean(Index(ShutOffMike,Micro),Gap)+NewSlant
21100           NEXT OGap
21110           SlantMean(Index(ShutOffMike,Micro),Gap)=SlantMean(Index(ShutOffMike,Micro),Gap)/3
21120        NEXT Micro
21130     NEXT Gap
21140   '
21150   'Calculate the new Sparkgap Coordinates resulting from the new Slantranges
21160   '
21170     FOR Gap=1 TO 3
21180        NewCoord(Gap,1)=(MikeDist(ShutOffMike,1)^2+SlantMean(Index(ShutOffMike,2),Gap)^2-SlantMean
          (Index(ShutOffMike,1),Gap)^2)/(2*MikeDist(ShutOffMike,1))
21190        NewCoord(Gap,2)=(MikeDist(ShutOffMike,2)^2+SlantMean(Index(ShutOffMike,2),Gap)^2-SlantMean
          (Index(ShutOffMike,3),Gap)^2)/(2*MikeDist(ShutOffMike,2))
21200        NewCoord(Gap,2)=(NewCoord(Gap,2)-NewCoord(Gap,1)*CosA(ShutOffMike))/SinA(ShutOffMike)
21210        NewCoord(Gap,3)=-SQR(SlantMean(Index(ShutOffMike,2),Gap)^2-NewCoord(Gap,1)^2-NewCoord(Gap,2)^2)
21220     NEXT Gap
21230   '
21240   'Determine the Difference to the previous Result
21250   '
21260     FOR Gap=1 TO 3
21270        Dif(Gap)=0
21280        FOR Coord=1 TO 3
21290           Dif(Gap)=Dif(Gap)+(GapCoord(Gap,Coord)-NewCoord(Gap,Coord))^2
21300        NEXT Coord
21310        Dif(Gap)=SQR(Dif(Gap))
21320     NEXT Gap
21330   '
21340   'Determine whether or not the Convergence Criteria is met
21350   '
21360     IF (Dif(1)<.01)AND(Dif(2)<.01)AND(Dif(3)<.01) THEN Busy=0
21370   '
21380   'Store the current Solution
21390   '
21400     FOR Gap=1 TO 3
21410        FOR Coord=1 TO 3
21420           GapCoord(Gap,Coord)=NewCoord(Gap,Coord)
21430        NEXT Coord
21440     NEXT Gap
21450
21460   WEND
21470
21480   RETURN
25000   '
25010   'Subroutine: Oblique Focal Point Coordinates
25020   '
25030   'All positions (focal point and sparkgaps) are known in microphone coordi-
25040   'nates. The relative location of the focal point is expressed as a linear
25050   'combination of the vectors XAxis (vector sparkgap#1-sparkgap#3), YAxis
25060   '(vector sparkgap#1-sparkgap#2) and ZAxis (crossproduct of XAxis x YAxis).
25070   'These vectors form an oblique righthanded coordinate system with origin
25080   'at sparkgap#1.
25090   'To solve is the vector equation:
25100   'Focal[1-3] = XFactor*XAxis[1-3] + YFactor*YAxis[1-3] + ZFactor*ZAxis[1-3]
25110   'This is done using the determinant method.
25120   '
25130   'Programmer: Johann Kettenberger
25140   '
25150   'Date: September 13, 1985
25160   '
25170   '*** Start of Subroutine ****************************************************
25180   '
25190   'Calculate the Vectors XAxis, YAxis, ZAxis
25200   '
25210   FOR Coord = 1 TO 3
25220      XAxis(Coord)=GapCoord(3,Coord)-GapCoord(1,Coord)
25230      YAxis(Coord)=GapCoord(2,Coord)-GapCoord(1,Coord)
25240   NEXT Coord
25250   '
25260   ZAxis(1)=(XAxis(2)*YAxis(3)-XAxis(3)*YAxis(2))/100
25270   ZAxis(2)=(XAxis(3)*YAxis(1)-XAxis(1)*YAxis(3))/100
25280   ZAxis(3)=(XAxis(1)*YAxis(2)-XAxis(2)*YAxis(1))/100
25290   '
25300   'Calculate Coefficient Determinant CD
25310   '
25320   CD=XAxis(1)*(YAxis(2)*ZAxis(3)-YAxis(3)*ZAxis(2))
25330   CD=CD-XAxis(2)*(YAxis(1)*ZAxis(3)-YAxis(3)*ZAxis(1))
25340   CD=CD+XAxis(3)*(YAxis(1)*ZAxis(2)-YAxis(2)*ZAxis(1))
25350   '
25360   'Calculate Determinant XD
25370   '
```

```
25380 XD=Focal(1)*(YAxis(2)*ZAxis(3)-YAxis(3)*ZAxis(2))
25390 XD=XD-Focal(2)*(YAxis(1)*ZAxis(3)-YAxis(3)*ZAxis(1))
25400 XD=XD+Focal(3)*(YAxis(1)*ZAxis(2)-YAxis(2)*ZAxis(1))
25410 '
25420 'Calculate Determinant YD
25430 '
25440 YD=XAxis(1)*(Focal(2)*ZAxis(3)-Focal(3)*ZAxis(2))
25450 YD=YD-XAxis(2)*(Focal(1)*ZAxis(3)-Focal(3)*ZAxis(1))
25460 YD=YD+XAxis(3)*(Focal(1)*ZAxis(2)-Focal(2)*ZAxis(1))
25470 '
25480 'Calculate Determinant ZD
25490 '
25500 ZD=XAxis(1)*(YAxis(2)*Focal(3)-YAxis(3)*Focal(2))
25510 ZD=ZD-XAxis(2)*(YAxis(1)*Focal(3)-YAxis(3)*Focal(1))
25520 ZD=ZD+XAxis(3)*(YAxis(1)*Focal(2)-YAxis(2)*Focal(1))
25530 '
25540 'Calculate the Factors
25550 '
25560 XFactor=XD/CD
25570 YFactor=YD/CD
25580 ZFactor=ZD/CD
25590 '
25600 RETURN
30000 '
30010 'Subroutine: Fiducial Triangle Dimensions and Angles
30020 '
30030 'This subroutine calculates the distances between the fiducial points and the
30040 'angles enclosed between the vectors from the fiducials through the center of
30050 'gravity of the fiducial triangle and to neighbouring fiducials.
30060 'This data is needed for the iterative correction of the fiducial coordinates.
30070 '
30080 'Programmer: Johann Kettenberger
30090 '
30100 'Date: September 20, 1985
30110 '
30120 '*** Start of Subroutine *********************************************
30130 '
30140 'Calculate the distances between the fiducials
30150 '
30160 F12=0: F13=0: F23=0
30170
30180 FOR Coord=1 TO 3
30190   F12=F12+(FidPoint(2,Coord)-FidPoint(1,Coord))^2
30200   F13=F13+(FidPoint(3,Coord)-FidPoint(1,Coord))^2
30210   F23=F23+(FidPoint(3,Coord)-FidPoint(2,Coord))^2
30220 NEXT Coord
30230 F12=SQR(F12)
30240 F13=SQR(F13)
30250 F23=SQR(F23)
30260 '
30270 'Calculate the coordinates of the center of gravity of the fiducial triangle
30280 'and the distances from the center of gravity to the fiducials
30290 '
30300 DisF(1)=0: DisF(2)=0: DisF(3)=0
30310
30320 FOR Coord=1 TO 3
30330   CoG(Coord)=(FidPoint(1,Coord)+FidPoint(2,Coord)+FidPoint(3,Coord))/3
30340   DisF(1)=DisF(1)+(FidPoint(1,Coord)-CoG(Coord))^2
30350   DisF(2)=DisF(2)+(FidPoint(2,Coord)-CoG(Coord))^2
30360   DisF(3)=DisF(3)+(FidPoint(3,Coord)-CoG(Coord))^2
30370 NEXT Coord
30380 DisF(1)=SQR(DisF(1))
30390 DisF(2)=SQR(DisF(2))
30400 DisF(3)=SQR(DisF(3))
30410 '
30420 'Calculate the angles between the vector from the fiducial through the center
30430 'of gravity and the vector to the other fiducial
30440 '
30450 'Angles at fiducial #1 corner
30460 '
30470 CosB12=(F12^2+DisF(1)^2-DisF(2)^2)/(2*F12*DisF(1))
30480 SinB12=SQR(1-CosB12*CosB12)
30490 CosB13=(F13^2+DisF(1)^2-DisF(3)^2)/(2*F13*DisF(1))
30500 SinB13=SQR(1-CosB13*CosB13)
30510 '
30520 'Angles at fiducial #2 corner
30530 '
30540 CosB21=(F12^2+DisF(2)^2-DisF(1)^2)/(2*F12*DisF(2))
30550 SinB21=SQR(1-CosB21*CosB21)
30560 CosB23=(F23^2+DisF(2)^2-DisF(3)^2)/(2*F23*DisF(2))
30570 SinB23=SQR(1-CosB23*CosB23)
30580 '
30590 'Angles at fiducial #3 corner
30600 '
30610 CosB31=(F13^2+DisF(3)^2-DisF(1)^2)/(2*F13*DisF(3))
30620 SinB31=SQR(1-CosB31*CosB31)
30630 CosB32=(F23^2+DisF(3)^2-DisF(2)^2)/(2*F23*DisF(3))
30640 SinB32=SQR(1-CosB32*CosB32)
30650 '
30660 RETURN
35000 '
35010 'Subroutine: Absolut Focal Point Coordinates
35020 '
35030 'This subroutine calculates the coordinates of the focal point in the
35040 'absolute microphone coordinate system
35050 '
35060 'Programmer: Johann Kettenberger
35070 '
35080 'Date: September 14, 1985
```

```
35090 '
35100 '*** Start of Subroutine *************************************************
35110 '
35120 'Calculate XAxis, YAxis and ZAxis Vectors
35130 '
35140 FOR Coord=1 TO 3
35150    XAxis(Coord)=GapCoord(3,Coord)-GapCoord(1,Coord)
35160    YAxis(Coord)=GapCoord(2,Coord)-GapCoord(1,Coord)
35170 NEXT Coord
35180
35190 ZAxis(1)=(XAxis(2)*YAxis(3)-XAxis(3)*YAxis(2))/100
35200 ZAxis(2)=(XAxis(3)*YAxis(1)-XAxis(1)*YAxis(3))/100
35210 ZAxis(3)=(XAxis(1)*YAxis(2)-XAxis(2)*YAxis(1))/100
35220 '
35230 'Calculate the Focal Point Coordinates
35240 '
35250 FOR Coord=1 TO 3
35260    Focal(Coord)=GapCoord(1,Coord)+XFac(1)*XAxis(Coord)+YFac(1)*YAxis(Coord)+ZFac(1)*ZAxis(Coord)
35270 NEXT Coord
35280
35290 RETURN
40000 '
40010 'Subroutine: Improved Fiducial Coordinates
40020 '
40030 'This subroutine calculates the improved estimates of the fiducial locations
40040 'using the data provided through the subroutine "Fiducial Triangle Dimensions
40050 'and Angles".
40060 'The calculations follow the same scheme as is used for determining the im-
40070 'proved sparkgap positions.
40080 '
40090 'Programmer: Johann Kettenberger
40100 '
40110 'Date: September 21, 1985
40120 '
40130 '*** Start of Subroutine *************************************************
40140 '
40150 'Calculate the Center of Gravity and the vectors from each Fiducial through
40160 'the Center of Gravity (Orientation vectors)
40170 '
40180    FOR Coord=1 TO 3   'Center of Gravity and Orientation vector from Fid#1
40190       FidToCoG(1,Coord)=Fiducial(2,Coord)+.5*(Fiducial(3,Coord)-Fiducial(2,Coord))-Fiducial(1,Coord)
40200       CoG(Coord)=Fiducial(1,Coord)+2/3*FidToCoG(1,Coord)
40210    NEXT Coord
40220    FOR Coord=1 TO 3   'Orientation vector from Fid#2
40230       FidToCoG(2,Coord)=Fiducial(3,Coord)+.5*(Fiducial(1,Coord)-Fiducial(3,Coord))-Fiducial(2,Coord)
40240    NEXT Coord
40250    FOR Coord=1 TO 3   'Orientation vector from Fid#3
40260       FidToCoG(3,Coord)=Fiducial(1,Coord)+.5*(Fiducial(2,Coord)-Fiducial(1,Coord))-Fiducial(3,Coord)
40270    NEXT Coord
40280 '
40290 'Calculate the improved Fiducial Positions lying on the Orientation vectors
40300 '
40310    FOR Fid=1 TO 3
40320       FOR Coord=1 TO 3
40330          NewFid(Fid,Fid,Coord)=CoG(Coord)-FidToCoG(Fid,Coord)/SQR(FidToCoG(Fid,1)^2+FidToCoG
              (Fid,2)^2+FidToCoG(Fid,3)^2)*DisF(Fid)
40340       NEXT Coord
40350    NEXT Fid
40360 '
40370 'Calculate the Normal of the Fiducial Triangle
40380 '
40390    TriNorm(1)=FidToCoG(2,2)*FidToCoG(1,3)-FidToCoG(2,3)*FidToCoG(1,2)
40400    TriNorm(2)=FidToCoG(2,3)*FidToCoG(1,1)-FidToCoG(2,1)*FidToCoG(1,3)
40410    TriNorm(3)=FidToCoG(2,1)*FidToCoG(1,2)-FidToCoG(2,2)*FidToCoG(1,1)
40420 '
40430 'Calculate Vec1 = TriNorm x FidToCoG; Vec2 = Vec1 x TriNorm
40440 '
40450    FOR Fid=1 TO 3
40460       Vec1(Fid,1)=TriNorm(2)*FidToCoG(Fid,3)-TriNorm(3)*FidToCoG(Fid,2)
40470       Vec1(Fid,2)=TriNorm(3)*FidToCoG(Fid,1)-TriNorm(1)*FidToCoG(Fid,3)
40480       Vec1(Fid,3)=TriNorm(1)*FidToCoG(Fid,2)-TriNorm(2)*FidToCoG(Fid,1)
40490       NormVec1(Fid)=SQR(Vec1(Fid,1)^2+Vec1(Fid,2)^2+Vec1(Fid,3)^2)
40500       Vec2(Fid,1)=Vec1(Fid,2)*TriNorm(3)-Vec1(Fid,3)*TriNorm(2)
40510       Vec2(Fid,2)=Vec1(Fid,3)*TriNorm(1)-Vec1(Fid,1)*TriNorm(3)
40520       Vec2(Fid,3)=Vec1(Fid,1)*TriNorm(2)-Vec1(Fid,2)*TriNorm(1)
40530       NormVec2(Fid)=SQR(Vec2(Fid,1)^2+Vec2(Fid,2)^2+Vec2(Fid,3)^2)
40540    NEXT Fid
40550 '
40560 'Calculate the improved Fiducial Positions off the Orientation vector
40570 '
40580    FOR Coord=1 TO 3   'Orientation given by Fiducial#1
40590       NewFid(1,2,Coord)=NewFid(1,1,Coord)+F12*(CosB12*Vec2(1,Coord)/NormVec2(1)+SinB12*Vec1
              (1,Coord)/NormVec1(1))
40600       NewFid(1,3,Coord)=NewFid(1,1,Coord)+F13*(CosB13*Vec2(1,Coord)/NormVec2(1)-SinB13*Vec1
              (1,Coord)/NormVec1(1))
40610    NEXT Coord
40620    FOR Coord=1 TO 3   'Orientation given by Fiducial#2
40630       NewFid(2,1,Coord)=NewFid(2,2,Coord)+F12*(CosB21*Vec2(2,Coord)/NormVec2(2)-SinB21*Vec1
              (2,Coord)/NormVec1(2))
40640       NewFid(2,3,Coord)=NewFid(2,2,Coord)+F23*(SinB23*Vec1(2,Coord)/NormVec1(2)+CosB23*Vec2
              (2,Coord)/NormVec2(2))
40650    NEXT Coord
40660    FOR Coord=1 TO 3   'Orientation given by Fiducial#3
40670       NewFid(3,1,Coord)=NewFid(3,3,Coord)+F13*(SinB31*Vec1(3,Coord)/NormVec1(3)+CosB31*Vec2
              (3,Coord)/NormVec2(3))
40680       NewFid(3,2,Coord)=NewFid(3,3,Coord)+F23*(CosB32*Vec2(3,Coord)/NormVec2(3)-SinB32*Vec1
              (3,Coord)/NormVec1(3))
40690    NEXT Coord
```

```
40700
40710 RETURN
45000 '
45010 'Subroutine: Transformation Matrix
45020 '
45030 'This subroutine calculates first the test block (microphone) coordinates
45040 'of the microphone (test block) coordinate system origin in order to de-
45050 'termine the shift between the two coordinate systems. Then it expresses
45060 'the unity vectors of the microphone (test block) system in terms of test
45070 'block (microphone) coordinates. This allows then to convert microphone
45080 '(test block) coordinates into test block (microphone) coordinates.
45090 '
45100 'Programmer: Johann Kettenberger
45110 '
45120 'Date: September 19, 1985
45130 '
45140 '*** Start of Subroutine *************************************************
45150 '
45160 FOR Case=1 TO 2    'Case1: Calculate the transformation matrix to go from the
45170                    '       microphone to the test block coordinate space
45180                    'Case2: Calculate the transformation matrix to go from the
45190                    '       test block to the microphone coordinate space
45200 '
45210 'Load the fiducial coordinates
45220 '
45230    IF Case=2, GOTO 45310
45240 .
45250    FOR Gap=1 TO 3
45260      FOR Coord=1 TO 3
45270        GapCoord(Gap,Coord)=Fiducial(Gap,Coord)
45280      NEXT Coord
45290    NEXT Gap
45300    GOTO 45380
45310
45320    FOR Gap=1 TO 3
45330      FOR Coord=1 TO 3
45340        GapCoord(Gap,Coord)=FidPoint(Gap,Coord)
45350      NEXT Coord
45360    NEXT Gap
45370 '
45380 'Calculate the shift between the origins and the unity vectors
45390 '
45400    FOR Ax=4 TO 1 STEP -1
45410 '
45420 'Calculate the vector from fiducial#1 to the microphone (test block) origin
45430 '
45440      Focal(1)=-GapCoord(1,1)
45450      Focal(2)=-GapCoord(1,2)
45460      Focal(3)=-GapCoord(1,3)
45470 '
45480 'Alter the vector to the origin to go to point 100 on the axis as soon as the
45490 'origin is determined (Ax=4: Calculate the shift between the coord. systems
45500 '3<Ax<1: Express the X-,Y-,Z-axis vectors of the one system in coordinates of
45510 'the other system.
45520 '
45530      IF Ax<4 THEN Focal(Ax)=Focal(Ax)+100
45540 '
45550 'Calculate the factors with which the vectors XAxis (Vector from fiducial#1
45560 'to fiducial#3), YAxis (vector from fiducial#1 to fiducial#2) and ZAxis
45570 '(crossproduct XAxis x YAxis) have to be multiplied to go from fiducial#1 to
45580 'the origin or the points at 100 from the origin on the axis. Since the
45590 'fiducials are known in both coordinate systems this factors are then used
45600 'with the same XAxis, YAxis and ZAxis vectors but now expressed in the other
45610 'coordinate system to determine the coordinates of the origin or the points
45620 'at 100 from the origin in this system.
45630 '
45640      GOSUB 25000
45650 '
45660 'Calculate the vectors XAxis, YAxis, ZAxis in the test block (microphone)
45670 'coordinate system
45680 '
45690      IF Case=2 GOTO 45770
45700
45710      FOR Coord=1 TO 3
45720        XAxis(Coord)=FidPoint(3,Coord)-FidPoint(1,Coord)
45730        YAxis(Coord)=FidPoint(2,Coord)-FidPoint(1,Coord)
45740        Focal(Coord)=FidPoint(1,Coord)
45750      NEXT Coord
45760      GOTO 45830
45770 .
45780      FOR Coord=1 TO 3
45790        XAxis(Coord)=Fiducial(3,Coord)-Fiducial(1,Coord)
45800        YAxis(Coord)=Fiducial(2,Coord)-Fiducial(1,Coord)
45810        Focal(Coord)=Fiducial(1,Coord)
45820      NEXT Coord
45830
45840      ZAxis(1)=(XAxis(2)*YAxis(3)-XAxis(3)*YAxis(2))/100
45850      ZAxis(2)=(XAxis(3)*YAxis(1)-XAxis(1)*YAxis(3))/100
45860      ZAxis(3)=(XAxis(1)*YAxis(2)-XAxis(2)*YAxis(1))/100
45870 '
45880 'Store the results
45890 '
45900      IF Ax<4 GOTO 45960
45910
45920      FOR Coord=1 TO 3
45930        TranMat(Case,Ax,Coord)=XFactor*XAxis(Coord)+YFactor*YAxis(Coord)+ZFactor*ZAxis(Coord)+Focal(Coord)
45940      NEXT Coord
45950      GOTO 46000
45960
```

```
45970      FOR Coord=1 TO 3
45980         TranMat(Case,Ax,Coord)=(XFactor*XAxis(Coord)+YFactor*YAxis(Coord)+ZFactor*ZAxis(Coord)+Focal
           (Coord)-TranMat(Case,4,Coord))/100
45990      NEXT Coord
46000
46010    NEXT Ax
46020
46030 NEXT Case
46040 '
46050 'Write the transformation matrices into file TRANMAT.DAT
46060 '
46070 OPEN "TranMat.DAT" FOR OUTPUT AS #1
46080    PRINT#1, Date$
46090    PRINT#1, Time$
46100    PRINT#1, ShutOffMike
46110    FOR Case=1 TO 2
46120      FOR Ax=1 TO 4
46130         FOR Coord=1 TO 3
46140            PRINT#1, TranMat(Case,Ax,Coord)
46150         NEXT Coord
46160      NEXT Ax
46170    NEXT Case
46180 CLOSE #1
46190
46200 RETURN
50000 '
50010 'Subroutine: Coordinate Transformation
50020 '
50030 'This subroutine transforms microphone system coordinates into test block
50040 'coordinates and vice versa. The direction of the transformation is deter-
50050 'mined by the flag "Case".
50060 'Case=1 : Transformation of microphone coordinates into test block coordinates
50070 'Case=2 : Transformation of test block coordinates into microphone coordinates
50080 '
50090 'Programmer: Johann Kettenberger
50100 '
50110 'Date: September 22, 1985
50120 '
50130 '*** Start of Subroutine ****************************************************
50140 '
50150 'Transformation of the coordinates
50160 '
50170 FOR Coord=1 TO 3
50180    AuxVec(Coord)=0
50190    FOR Ax=1 TO 3
50200       AuxVec(Coord)=AuxVec(Coord)+Focal(Ax)*TranMat(Case,Ax,Coord)
50210    NEXT Ax
50220    AuxVec(Coord)=AuxVec(Coord)+TranMat(Case,4,Coord)  'add shift between systems
50230 NEXT Coord
50240 '
50250 'Reassign the transformed coordinates
50260 '
50270 Focal(1)=AuxVec(1)
50280 Focal(2)=AuxVec(2)
50290 Focal(3)=AuxVec(3)
50300
50310 RETURN
55000 '
55010 'Subroutine: Microphone Distances
55020 '
55030 'This subroutine calculates the distances between the microphones currently
55040 'being used. This data are stored in the file MIKE.DIS and are used to im-
55050 'prove the accuracy with which the distances are known.
55060 '
55070 'Programmer: Johann Kettenberger
55080 '
55090 'Date: October 2, 1985
55100 '
55110 '*** Start of Subroutine ****************************************************
55120 '
55130 'Calculation of angle 2-1-3 of sparkgap triangle
55140 '
55150 CosW=(30.041^2+29.657^2-29.995^2)/(2*30.041*29.657)
55160 SinW=SQR(1-CosW*CosW)
55170 '
55180 'Calculation of the microphone coordinates
55190 '
55200 FOR Phone=1 TO 3
55210    IF Phone=ShutOffMike GOTO 55260
55220    MiCo(Phone,1)=(SlantMean(Phone,1)^2+29.657^2-SlantMean(Phone,3)^2)/59.314
55230    MiCo(Phone,2)=(SlantMean(Phone,1)^2+30.041^2-SlantMean(Phone,2)^2)/60.082
55240    MiCo(Phone,2)=(MiCo(Phone,2)-MiCo(Phone,1)*CosW)/SinW
55250    MiCo(Phone,3)=SQR(SlantMean(Phone,1)^2-MiCo(Phone,1)^2-MiCo(Phone,2)^2)
55260 NEXT Phone
55270 '
55280 'Calculate the distances between the microphones
55290 '
55300 FOR D=1 TO 3
55310    IF D=1 THEN From=1: Bis=2
55320    IF D=2 THEN From=1: Bis=3
55330    IF D=3 THEN From=2: Bis=3
55340    Dist=0
55350    FOR Coord=1 TO 3
55360       Dist=Dist+(MiCo(Index(ShutOffMike,From),Coord)-MiCo(Index(ShutOffMike,Bis),Coord))^2
55370    NEXT Coord
55380    Dist=SQR(Dist)
55390    PRINT#3,Index(ShutOffMike,From),Index(ShutOffMike,Bis),Dist
55400 NEXT D
55410
```

```
55420 RETURN
60000 '
60010 'Subroutine: Focal Plane Coefficients
60020 '
60030 'This subroutine calculates the coefficients of the focal plane in the
60040 'CT coordinate space. This data are needed by the reconstruction programs
60050 'to calculate the intersection between the tumor and the focal plane
60060 '
60070 'Programmer: John F. Hatch
60080 '            Johann Kottenberger
60090 '
60100 'Date: October 3, 1985
60110 '
60120 '*** Start of Subroutine ********************************************
60130 '
60140 'Find out where the surgeon is looking
60150 '
60160 FOR GapToFire=1 TO 3
60170   GOSUB 10000
60180 NEXT GapToFire
60190 '
60200 'Calculate the microphone distances
60210 '
60220 GOSUB 55000
60230 '
60240 'Calculate the sparkgap coordinates
60250 '
60260 GOSUB 20000
60270 '
60280 'Calculate the focal point
60290 '
60300 GOSUB 35000
60310 '
60320 'Calculate the normal and the orientation vectors
60330 '
60340 FOR Coord=1 TO 3
60350   Normal(Coord)=Focal(Coord)-(XFac(2)*XAxis(Coord)+YFac(2)*YAxis(Coord)+ZFac(2)*ZAxis(Coord))
60360   Orient(Coord)=XFac(3)*XAxis(Coord)+YFac(3)*YAxis(Coord)+ZFac(3)*ZAxis(Coord)-Focal(Coord)
60370 NEXT Coord
60380 '
60390 'Transformation of the focal point and the normal and orientation vectors into
60400 'the CT coordinate space
60410 '
60420 Case=1
60430 GOSUB 50000
60440 '
60450 'Store converted focal coordinates
60460 '
60470 FOR Coord=1 TO 3
60480   Vec1(1,Coord)=Focal(Coord)
60490   Focal(Coord)=Normal(Coord)
60500 NEXT Coord
60510 GOSUB 50000
60520 '
60530 'Store the converted normal point coordinates
60540 '
60550 FOR Coord=1 TO 3
60560   Normal(Coord)=Focal(Coord)
60570   Focal(Coord)=Orient(Coord)
60580 NEXT Coord
60590 GOSUB 50000
60600 '
60610 'Store the converted orientation vector
60620 '
60630 FOR Coord=1 TO 3
60640   Orient(Coord)=Focal(Coord)
60650   Focal(Coord)=Vec1(1,Coord)
60660 NEXT Coord
60670 '
60680 'Calculate the constant coefficient in the focal plane equation
60690 '
60700 D=0
60710 FOR Coord=1 TO 3
60720   D=D+Normal(Coord)*Focal(Coord)
60730 NEXT Coord
60740 '
60750 'Calculate the direction cosines for the orientation vector
60760 '
60770 Norm=0
60780 FOR Coord=1 TO 3
60790   Norm=Norm+Orient(Coord)^2
60800 NEXT Coord
60810 Norm=SQR(Norm)
60820 FOR Coord=1 TO 3
60830   Orient(Coord)=Orient(Coord)/Norm
60840 NEXT Coord
60850 '
60860 'Output the data into the file RECI.DAT
60870 '
60880 OPEN "Reci.Dat" FOR OUTPUT AS #4
60890   PRINT#4,USING"####.########";Normal(1)
60900   PRINT#4,USING"####.########";Normal(2)
60910   PRINT#4,USING"####.########";Normal(3)
60920   PRINT#4,USING"####.########";D
60930   PRINT#4,USING"####.########";Focal(1)
60940   PRINT#4,USING"####.########";Focal(2)
60950   PRINT#4,USING"####.########";Focal(3)
60960   PRINT#4,USING"####.########";Orient(1)
60970   PRINT#4,USING"####.########";Orient(2)
```

```
60980    PRINT#4,USING"####.########";Orient(3)
60990 CLOSE #4
61000
61010 PRINT*
61020 PRINT"The registration procedure is completed. The focal plane data are"
61030 PRINT"stored in the file RECI.DAT."
61040
61050 RETURN
```

*Appendix E*

```
          FFFFF  TTTTT  PPPP
          F        T    P   P
          F        T    P   P
          FFFF     T    PPPP
          F        T    P
          F        T    P
          F        T    P

FFFFFFFFFF    IIIIII    DDDDDDDD      UU      UU    CCCCCCC
   FFFFFFFFFF    IIIIII    DDDDDDDD      UU      UU    CCCCCCC
   FF             II       DD     DD     UU      UU    CC
   FF             II       DD     DD     UU      UU    CC
   FF             II       DD     DD     UU      UU    CC
   FF             II       DD     DD     UU      UU    CC
   FFFFFFFF       II       DD     DD     UU      UU    CC
   FFFFFFFF       II       DD     DD     UU      UU    CC
   FF             II       DD     DD     UU      UU    CC
   FF             II       DD     DD     UU      UU    CC
   FF             II       DD     DD     UU      UU    CC
   FF           IIIIII     DDDDDDDD      UUUUUUUU      CCCCCCC
   FF           IIIIII     DDDDDDDD      UUUUUUUU      CCCCCCC

RRRRRRR
                           RRRRRRRR
                           RR    RR       ....      1111
                           RR    RR       ....      1111
                           RR    RR                   11
                           RR    RR                   11
                           RRRRRRRR       ....        11
                           RRRRRRRR       ....        11
                           RR  RR         ....        11
                           RR   RR        ....        11
                           RR    RR        ..         11
                           RR    RR        ..         11
                           RR    RR        ..      111111
                           RR    RR        ..      111111
```

File _DUA2:[PUBLIC.FTP.PRINTING]FIDUC.R;1 (4833,21,0), last revised on 14-NOV-1985 13:47, is a 20 block sequential file owned by UIC [FTP]. The records are variable length with implied (CR) carriage control. The longest record is 94 bytes.

Job FIDUC (1199) queued to LCAO on 14-NOV-1985 13:47 by user FTP, UIC [FTP], under account SYSTEM at priority 4, started on printer _LCAO: on 14-NOV-1985 13:49 from queue LCAO.

```
FILE NAME:    fiduc.r

VERSION:   1.0

PROGRAMMER:   William J. Murray

DATE OF CREATION:   2/10/85

ENTRY POINTS:   program fiduc

INPUT/OUTPUT FILES:   infile, fidout.dat

INCLUDE FILES #####

dir4.h
```

```
#    hdr4.h
slc4.h

GLOBAL DATA STRUCTURES AND VARIABLES: #####

# an include file for the directory header block
# integer*4    revnum,
#              outsecu,
#              cpsecu,
#              outnum(306),
#              outstar(306)
# common /direct/revnum,outsecu,cpsecu,outnum,outstar

# an include file for the outline set header block
# integer*4    olinum,
#              day,
#              month,
#              year,
#              picdkey,
#              totslic,
#              slicnum(10),
#              routbln(10),
#              refdist(10)

# common /headi/olinum,day,month,year,
# picdkey,totslic,slicnum,routbln,refdist

# character*65    patient
# character*65    scancode
# character*65    hospital
# character*65    consult
# character*65    tumsite
# character*65    comment

# common /headc/patient,scancode,hospital,consult,tumsite,comment

# an include file containing all slice parameters
# integer*4    ctlcx,
#              ctlcy,
#              cxleng,
#              cyleng,
#              ctwsdat,
#              ctypnum(8),
#              creldens(8),
#              cptscnt(8),
#              cx(8,500),
#              cy(8,500)

# common /slicei/ctlcx,ctlcy,cxleng,cyleng,ctwsdat,
# ctypnum,creldens,cptscnt,cx,cy

# character*65 cdumname(8)

# common /slicec/cdumname

# an include file for the reconstruction routines
# real fpeqna,fpeqnb,fpeqnc,fpeqnd
# real xfpt,yfpt,zfpt
# real lmb(3),mu(3),nu(3)
# real oddfpx(8,250),oddfpy(8,250),oddfpz(8,250)
# real evnfpx(8,250),evnfpy(8,250),evnfpz(8,250)

# common /rcnsr/fpeqna,fpeqnb,fpeqnc,fpeqnd,xfpt,yfpt,zfpt,
# lmb,mu,nu,oddfpx,oddfpy,oddfpz,evnfpx,evnfpy,evnfpz

# integer*4 oddpts(8),evnpts(8),ist,jsto,jste
# integer*4 fstptx(8),fstpty(8)

# common /rcnsi/oddpts,evnpts,ist,jsto,jste,fstptx,fstpty

################################################################
##########################################################
########################################################## program fiduc
character*15 infile
character*1 chgans,chgfid
```

```
logical*4 filex1,filex2
integer*4   i,j,scsl,lbsgn
real zspace real fidx(3),fidy(3),fidz(3)

include '../h/dir4.h'
include '../h/hdr4.h'
include '../h/slc4.h' chgans = 'y'
chgfid = 'n'

# What files exist?
inquire(file='fidout.dat',exist=filex2)
if(filex2 & .true.) {
    open(2, file='fidout.dat', status='old',
        access='sequential',form='formatted')
    read(2,'(a15)') infile
    read(2,'(i8)') lbsgn
# read the directory
call rfdirect(1)

i=1
scsl = 0
while (outnum(i) != 0) {
    # read the outline header
    call rfouth(1,outstar(i))
    do j=1,totslic {
        # read the slice
        call rfslic(1, outstar(i), j)
        # write out the fiducials
        call wffidu(scsl,zspace)
        scsl = scsl+1
        }
    i = i+1
    } close the slice data file
close(1)

# Input the desired fiducials to write to a file
write(6,'(" ")')
write(6,'("From the list of possible fiducials above, select")')
write(6,'("three - fid1(x,y,z),fid2(x,y,z),fid3(x,y,z).")')
write(6,'("Input the fiducials as follows:")')
write(6,'("EXAMPLE ")')
write(6,'("fid1 ? 0.,2.5,5.0")')
write(6,'(" ")')
do i=1,3 {
    write(6,'("fid",i1," ? ",$)') i
    read(5,'(3(f12.8))') fidx(i),fidy(i),fidz(i)
    } write(6,'(" ")')

write to fidout.dat
rewind 2
write(2,'(a15)') infile
write(2,'(i8)') lbsgn
write(2,'(f12.8)') zspace
do i=1,3 {
    write(2,'(i2,",",2(f12.8,","),f12.8)') i,fidx(i),fidy(i),fidz(i)
    } close(2)
end routine to read a formatted directory sector
subroutine rfdirect(fdes)
integer*2   fdes
integer*4   i
character*1 start
character*2 finish include '../h/dir4.h' read(fdes,'(a1)') start
```

```
read(fdes,'(i8,1x,i8,1x,i8)') revnum,outsecu,cpsecu
i=1
repeat {
    read(fdes,'(i8,1x,i8)') outnum(i),outstar(i)
    i = i+1
    } until (outnum(i-1) == 0)

read(fdes,'(a2)') finish return
end routine to read an unformatted outline header
subroutine rfouth(fdes, sectnum)
integer*2   fdes
integer*4   sectnum,i character*1 start
character*2 finish include '../h/dir4.h'
include '../h/hdr4.h' read(fdes,'(a1)') start read(fdes,'(i8)') olinum
read(fdes,'(i8,1x,i8,1x,i8)') day,month,year
read(fdes,'(i8)') picdkey read(fdes,'(a)') patient
read(fdes,'(a)') scancode
read(fdes,'(a)') hospital
read(fdes,'(a)') consult
read(fdes,'(a)') tumsite
read(fdes,'(a)') comment read(fdes,'(i8)') totslic do i=1,totslic {
    read(fdes,'(i8,1x,i8,1x,i8)') slicnum(i),routbln(i),refdist(i)
    } read(fdes,'(a2)') finish return
end routine to read a formatted outline slice
subroutine rfslic(fdes, sectnum, nslice)
integer*2   fdes
integer*4   sectnum,
            nslice,
            i,j character*1 start
character*2 finish include '../h/dir4.h'
include '../h/hdr4.h'
include '../h/slc4.h' read(fdes,'(a1,1x,i8)') start,nslice read(fdes,'(i8,1x,i8,1x,i8,1x,i8)') ctlcx,ctlcy,cxleng,cyleng read(fdes,'(i8)') ctwsdat i=1
read(fdes,'(i8)') ctypnum(i)
while(ctypnum(i) != 0)  { if(ctypnum(i) == 1) {
        read(fdes,'(i8)') cptscnt(i)
        }
```

```
    else if(ctypnum(i) == 2) {
        read(fdes,'(a)') cdumname(i)
        read(fdes,'(i8)') creldens(i)
        read(fdes,'(i8)') cptscnt(i)
        } else if(ctypnum(i) == 3) {
        read(fdes,'(a)') cdumname(i)
        read(fdes,'(i8)') creldens(i)
        read(fdes,'(i8)') cptscnt(i)
        } else if(ctypnum(i) == 4) {
        read(fdes,'(a)') cdumname(i)
        read(fdes,'(i8)') cptscnt(i)
        } else {
        write(6,'("Illegal Type Number = ",i8)') ctypnum(i)
        stop 'rfslic error'
        } do j=1,cptscnt(i) {
        read(fdes,'(i8,1x,i8)') cx(i,j),cy(i,j)
        } i = i+1 read(fdes,'(i8)') ctypnum(i)
    } read(fdes,'(a2)') finish return
end routine to write a formatted fiducial data set
subroutine wffidu(scsl, zspace)
integer*4   scsl,
            i, j
real xcoord,ycoord,zcoord,zspace
integer*2 setx,sety include '../h/dir4.h'
include '../h/hdr4.h'
include '../h/slc4.h' setx=0
sety=0 zcoord = real(scsl)*zspace/10.

i=1
while(ctypnum(i) != 0) { if((ctypnum(i) == 4)&&(cptscnt(i) == 2)) { do j=1,cptscnt(i) { if( (cx(i,j) > (-1900)) && (cx(i,j) < 1900)) {
            xcoord = real(cx(i,j))/160.
            setx = setx+1
            if(setx > 1) {
                write(6,'("error:   undetermined x coordinate")')
                stop 'fiduc error'
                }
            } if( (cy(i,j) > (-1800)) && (cy(i,j) < 1800)) {
            ycoord = real(cy(i,j))/160.
            sety = sety+1
            if(sety > 1) {
                write(6,'("error:   undetermined y coordinate")')
                stop 'fiduc error'
                }
            }
```

```
        }
# to maintain right hand coord sys yet make up y positive
ycoord = -1.*ycoord write(6,'("",a12,"FID => (",2(f10.4,","),f10.4,")")') cdumname(i),
     xcoord,ycoord,zcoord)

setx=0
sety=0
i = i+1
} return
end
```

Appendix F

```
FILE NAME:   recon.r

VERSION:   1.0

PROGRAMMER:   William J. Murray

DATE OF CREATION:   2/10/85

ENTRY POINTS:   program recon

INPUT/OUTPUT FILES:   reci.dat, reco.dat

INCLUDE FILES #####

dir4.h
hdr4.h
```

```
#    slc4.h

GLOBAL DATA STRUCTURES AND VARIABLES: #####

# an include file for the directory header block
# integer*4    revnum,
#              outsecu,
#              cpsecu,
#              outnum(306),
#              outstar(306)
# common /direct/revnum,outsecu,cpsecu,outnum,outstar

# an include file for the outline set header block
# integer*4    olinum,
#              day,
#              month,
#              year,
#              picdkey,
#              totslic,
#              slicnum(10),
#              routbln(10),
#              refdist(10)

# common /headi/olinum,day,month,year,
# picdkey,totslic,slicnum,routbln,refdist

# character*65    patient
# character*65    scancode
# character*65    hospital
# character*65    consult
# character*65    tumsite
# character*65    comment

# common /headc/patient,scancode,hospital,consult,tumsite,comment

# an include file containing all slice parameters
# integer*4    ctlcx,
#              ctlcy,
#              cxleng,
#              cyleng,
#              ctwsdat,
#              ctypnum(8),
#              creldens(8),
#              cptscnt(8),
#              cx(8,500),
#              cy(8,500)

# common /slicei/ctlcx,ctlcy,cxleng,cyleng,ctwsdat,
# ctypnum,creldens,cptscnt,cx,cy

# character*65 cdumname(8)

# common /slicec/cdumname

# an include file for the reconstruction routines
# real fpeqna,fpeqnb,fpeqnc,fpeqnd
# real xfpt,yfpt,zfpt
# real lmb(3),mu(3),nu(3)
# real oddfpx(8,250),oddfpy(8,250),oddfpz(8,250)
# real evnfpx(8,250),evnfpy(8,250),evnfpz(8,250)

# common /rcnsr/fpeqna,fpeqnb,fpeqnc,fpeqnd,xfpt,yfpt,zfpt,
# lmb,mu,nu,oddfpx,oddfpy,oddfpz,evnfpx,evnfpy,evnfpz

# integer*4 oddpts(8),evnpts(8),ist,jsto,jste
# integer*4 fstptx(8),fstpty(8)

# common /rcnsi/oddpts,evnpts,ist,jsto,jste,fstptx,fstpty

################################################################
##########################################################
########################################################## program recon
      character*15 infile
      character*1 chgans
```

```
integer*4    i,j,k,tns,tmpns,slipts,dslipts,lbsgn
logical*4 filex1,filex2 real magabc,eterm,zspace
real fpla,fplb,fplc
real fplsx(10),fplsy(10),fplsz
real mfplsx(10),mfplsy(10),mfplsz(10)
real dfplsx(10),dfplsy(10)

include '../h/dir4.h'
include '../h/hdr4.h'
include '../h/slc4.h'
include '../h/recon.h' chgans = 'n'

What files exist?
inquire(file='fidout.dat',exist=filex2)
if(filex2 & .true.) {
    open(2, file='fidout.dat', status='old',
         access='sequential',form='formatted')
    read(2,'(a15)') infile
    read(2,'(i8)') lbsgn
# zspace in mm convert to cm
    read(2,'(f12.8)') zspace write(6,'("RECON")')
    write(6,'("Current slice data file:   ",a15)') infile
    write(6,'("Number of reconstruction slices:   ",i8)') lbsgn
    write(6,'("Current z spacing(mm):   ",f12.8)') zspace
    write(6,'(" ")')
    write(6,'("Change current slice data(y or n)?   ",$)')
    read(5,'(a)') chgans

} close(2)

Interactive input inquiry
if((chgans == 'y') || (filex2 & .false.)) {
    write(6,'("Changing current slice parameters...")')
    write(6,'("Slice data file?   ",$)')
    read(5,'(a15)') infile
    write(6,'("Number of reconstruction slices?   ",$)')
    read(5,'(i8)') lbsgn
    write(6,'("Enter the slice z-spacing:   ",$)')
    read(5,'(f12.8)') zspace
    write(6,'(" ")')
    chgans = 'n'
    }
else {
    write(6,'("Slice data file and z spacing remain unchanged")')
    write(6,'(" ")')
    } inquire(file=infile,exist=filex1)

if(filex1 & .true.) {
    open(1, file=infile, status='old',
         access='sequential',form='formatted')
    }
else {
    write(6,'("The slice data file ",a15," does not exist")') infile
    stop 'open error'
    } inquire(file='reci.dat',exist=filex2)
if(filex2 & .true.) {
    open(2, file='reci.dat', status='old',
         access='sequential',form='formatted')

read(2,'(f12.8)') fpeqna
    read(2,'(f12.8)') fpeqnb
    read(2,'(f12.8)') fpeqnc
    read(2,'(f12.8)') fpeqnd
    read(2,'(f12.8)') xfpt
```

```
            read(2,'(f12.8)') yfpt
            read(2,'(f12.8)') zfpt
            read(2,'(f12.8)') lmb(2)
            read(2,'(f12.8)') mu(2)
            read(2,'(f12.8)') nu(2)

write(6,'("The equation of the focal plane is:")')
        write(6,'("A*x + B*y + C*z = D")')
        write(6,'(" ")')
        write(6,'("Current information:")')
        write(6,'("     The coefficients (A,B,C,D):")')
        write(6,'(3(f12.8,","),f12.8)') fpeqna,fpeqnb,fpeqnc,fpeqnd
        write(6,'(" ")')
        write(6,'("     The focal point (X,Y,Z):")')
        write(6,'(2(f12.8,","),f12.8)') xfpt,yfpt,zfpt
        write(6,'(" ")')
        write(6,'("     The direction cosines (aX,aY,aZ):   ")')
        write(6,'(2(f12.8,","),f12.8)') lmb(2),mu(2),nu(2)
        write(6,'(" ")')

write(6,'("Change current information(y or n)?   ",$)')
        read(5,'(a)') chgans
        }
    else {
        # Interactive input inquiry
        write(6,'("The input file RECI.DAT was not found")')
        write(6,'(" ")')
        chgans = 'y'
        } if(chgans == 'y') {
        write(6,'("The equation of the focal plane is:")')
        write(6,'("A*x + B*y + C*z = D")')
        write(6,'(" ")')
        write(6,'("Enter the following information:")')
        write(6,'("     The coefficients (A,B,C,D):   ",$)')
        read(5,'(4f12.8)') fpeqna,fpeqnb,fpeqnc,fpeqnd
        write(6,'("     The focal point (X,Y,Z):   ",$)')
        read(5,'(3f12.8)') xfpt,yfpt,zfpt
        write(6,'("     The direction cosines (aX,aY,aZ):   ",$)')
        read(5,'(3f12.8)') lmb(2),mu(2),nu(2)
        write(6,'(" ")')
        } assumes a blank floppy...
starts with the first outline block
# trys to read up to 10 slices per block
# then goes on to the next outline block
# until tns is exhausted
tns = lbsgn
zspace = zspace/10.

# open the data files
open(1, file=infile, status='old', access='sequential',
form='formatted')

inquire(file='reco.dat',exist=filex2)
if(filex2 & .true.) {
    open(2, file='reco.dat',status='old', access='sequential',
    form='formatted')
    rewind 2
    }
else {
    open(2, file='reco.dat',status='new', access='sequential',
    form='formatted')
    } initialize some static array indicies
do i=1,8 {
    oddpts(i) = 0
    evnpts(i) = 0
    }
ist = 1
jsto = 1
jste = 1
```

```
# calculate the direction cosines for the +k' axis
input units cm
magabc = (fpeqna*fpeqna)+(fpeqnb*fpeqnb)+(fpeqnc*fpeqnc)
magabc = sqrt(magabc)
lmb(3) = fpeqna/magabc
mu(3) = fpeqnb/magabc
nu(3) = fpeqnc/magabc orientation check for direction
cosine to find the e term
# if(fpeqnc == 0.) {
#     if(fpeqnb == 0.) {
#         eterm = fpeqna
#         }
else {
#         eterm = fpeqnb
#         }
}
else {
#     eterm = fpeqnc
#     }

# if(eterm > 0.) {
#     eterm = 1.
#     }
else {
#     eterm = -1.
#     }

# The above logic was to select the orientation of the z'
# axis; however in practice the procedure supplied an
# interesting random sequence of mirror images.  This was
# corrected by making eterm = 1 permenantly.
eterm = 1.

# set direction
lmb(3) = lmb(3)*eterm
mu(3) = mu(3)*eterm
nu(3) = nu(3)*eterm

#.calculate the direction cosines
# for the +i' axis
# Also the t term is chosen to be -1
# to orient the plane correctly
# for display
lmb(1) = 1.*( mu(2)*nu(3) - mu(3)*nu(2) )
mu(1) = 1.*( nu(2)*lmb(3) - nu(3)*lmb(2) )
nu(1) = 1.*( lmb(2)*mu(3) - lmb(3)*mu(2) )

call rfdirect(1)

i=1
tmpns = tns
fplsz = 0.
while ((outnum(i) != 0) && (tmpns != 0))  { call rfouth(1,outstar(i))

do j=1,totslic {
        call rfslic(1, outstar(i), j)

# on a per slice basis
        fpla = fpeqna
        fplb = fpeqnb
        fplc = fpeqnc*fplsz - fpeqnd call perslic(fpla,fplb,fplc,fplsx,fplsy,slipts)

call coordt(fplsx,fplsy,fplsz,mfplsx,mfplsy,mfplsz,slipts)

# here is where we insert the proper sorting technique
whatever it may be, such as a store delay procedure if j > 1 then delay system is primed
        if(j > 1) {
            call grsort(mfplsx,mfplsy,dfplsx,dfplsy,slipts,dslipts)
            }
```

```
        # delay step forward
        dslipts = slipts
        do k=1,dslipts {
            dfplsx(k) = mfplsx(k)
            dfplsy(k) = mfplsy(k)
            } fplsz = fplsz + zspace
        } flush the last points from the delay array
    call grsort(mfplsx,mfplsy,dfplsx,dfplsy,slipts,dslipts)

tmpns = tmpns-totslic
    i = i+1
    } initialize ctypnum and cptscnt
do i=1,8 {
    ctypnum(i) = 0
    cptscnt(i) = 0
    } do i=1,ist {
    ctypnum(i) = 1
    cptscnt(i) = oddpts(i) + evnpts(i)
    } do i=1,ist {
    do j=1,oddpts(i) {
        if(j == 1) {
            fstptx(i) = int(oddfpx(i,j)*160.)
            fstpty(i) = int(oddfpy(i,j)*160.)
            } cx(i,j) = int(oddfpx(i,j)*160.)
        cy(i,j) = int(oddfpy(i,j)*160.)
        } do j=(oddpts(i)+1),cptscnt(i) {
        cx(i,j) = int(evnfpx(i,(cptscnt(i)+1-j))*160.)
        cy(i,j) = int(evnfpy(i,(cptscnt(i)+1-j))*160.)
        }
    } make the connection to complete the contour
do i=1,ist {
    cptscnt(i) = cptscnt(i) + 1
    cx(i,cptscnt(i)) = fstptx(i)
    cy(i,cptscnt(i)) = fstpty(i)
    } call wrecdir(2)
call wrecoh(2)
call wrecsl(2)

close(1)
close(2)
end routine to read a formatted directory sector
subroutine rfdirect(fdes)
integer*2    fdes
integer*4    i
character*1 start
character*2 finish include '../h/dir4.h' read(fdes,'(a1)') start read(fdes,'(i8,1x,i8,1x,i8)') revnum,outsecu,cpsecu i=1
repeat {
    read(fdes,'(i8,1x,i8)') outnum(i),outstar(i)
```

```
        i = i+1
        } until (outnum(i-1) == 0)

read(fdes,'(a2)') finish return
end routine to write a formatted directory
subroutine wfdirect(fdes)
integer*2    fdes
integer*4    i include '../h/dir4.h' write(fdes,'("d")')

write(fdes,'(i8,",",i8,",",i8)') revnum,outsecu,cpsecu i=1
repeat {
    write(fdes,'(i8,",",i8)') outnum(i),outstar(i)
    i = i+1
    } until (outnum(i-1) == 0)

write(fdes,'("dd")')

return
end routine to read an unformatted outline header
subroutine rfouth(fdes, sectnum)
integer*2    fdes
integer*4    sectnum,i character*1 start
character*2 finish include '../h/dir4.h'
include '../h/hdr4.h' read(fdes,'(a1)') start read(fdes,'(i8)') olinum
read(fdes,'(i8,1x,i8,1x,i8)') day,month,year
read(fdes,'(i8)') picdkey read(fdes,'(a)') patient
read(fdes,'(a)') scancode
read(fdes,'(a)') hospital
read(fdes,'(a)') consult
read(fdes,'(a)') tumsite
read(fdes,'(a)') comment read(fdes,'(i8)') totslic do i=1,totslic {
    read(fdes,'(i8,1x,i8,1x,i8)') slicnum(i),routbln(i),refdist(i)
    } read(fdes,'(a2)') finish return
end routine to write a formatted outline header
subroutine wfouth(fdes, sectnum)
integer*2    fdes
integer*4    sectnum,i include '../h/dir4.h'
include '../h/hdr4.h' write(fdes,'("h")')
```

```
write(fdes,'(iQ)') olinum
write(fdes,'(i8,",",i8,",",i8)') day,month,year
write(fdes,'(i8)') picdkey write(fdes,'(a)') patient
write(fdes,'(a)') scancode
write(fdes,'(a)') hospital
write(fdes,'(a)') consult
write(fdes,'(a)') tumsite
write(fdes,'(a)') comment write(fdes,'(i8)') totslic do i=1,totslic {
    write(fdes,'(i8,",",i8,",",i8)') slicnum(i),
    routbln(i),refdist(i)
    } write(fdes,'("hh")')

return
end routine to read a formatted outline slice
subroutine rfslic(fdes, sectnum, nslice)
integer*2   fdes
integer*4   sectnum,
            nslice,
            i,j character*1 start
character*2 finish include '../h/dir4.h'
include '../h/hdr4.h'
include '../h/slc4.h' read(fdes,'(a1,1x,i8)') start,nslice read(fdes,'(i8,1x,i8,1x,i8,1x,i8)') ctlcx,ctlcy,cxlong,cyleng read(fdes,'(i8)') ctwsdat i=1
read(fdes,'(i8)') ctypnum(i)
while(ctypnum(i) != 0)  { if(ctypnum(i) == 1) {
        read(fdes,'(i8)') cptscnt(i)
        } else if(ctypnum(i) == 2)  {
        read(fdes,'(a)') cdumname(i)
        read(fdes,'(i8)') creldens(i)
        read(fdes,'(i8)') cptscnt(i)
        } else if(ctypnum(i) == 3)  {
        read(fdes,'(a)') cdumname(i)
        read(fdes,'(i8)') creldens(i)
        read(fdes,'(i8)') cptscnt(i)
        } else if(ctypnum(i) == 4)  {
        read(fdes,'(a)') cdumname(i)
        read(fdes,'(i8)') cptscnt(i)
        } else {
        write(6,'("Illegal Type Number = ",i8)') ctypnum(i)
        stop 'rfslic error'
        } do j=1,cptscnt(i) {
        read(fdes,'(i8,1x,i8)') cx(i,j),cy(i,j)
        }
```

```
    i = i+1 read(fdes,'(i8)') ctypnum(i)
    } read(fdes,'(a2)') finish return
end routine to find the intersection(s)
of the line representing the focal plane
# on a per slice basis and the contour(s)
# within a desired slice
# output is returned within the arrays fplsx and fplsy
subroutine perslic(fpla,fplb,fplc,fplsx,fplsy,numpts)
integer*4   i, j
integer*4   numpts real fpla,fplb,fplc
real fplsx(10),fplsy(10)
real x1,y1,x2,y2,xseg,yseg
real a1,b1,c1,a2,b2,c2,deta include '../h/dir4.h'
include '../h/hdr4.h'
include '../h/slc4.h' numpts = 0 a2 = fpla
b2 = fplb
c2 = -1.*fplc i=1
while(ctypnum(i) != 0)  { if((ctypnum(i) != 4)&&(cptscnt(i) > 4))  { x1 = real(cx(i,1))/160.
        y1 = real(cy(i,1))/160.
        do j=2,cptscnt(i) {
            x2 = real(cx(i,j))/160.
            y2 = real(cy(i,j))/160.

a1 = y1 - y2
            b1 = x2 - x1
            c1 = y1*b1 + x1*a1 deta = a1*b2 - a2*b1
            if(deta != 0.)  {
                xseg = (b2*c1 - b1*c2)/deta
                yseg = (a1*c2 - a2*c1)/deta
                if( ( (xseg >= min(x1,x2)) && (xseg < max(x1,x2)) ) ||
                    ( (yseg >= min(y1,y2)) && (yseg < max(y1,y2)) ) )  {
                    numpts = numpts+1
                    fplsx(numpts) = xseg
                    fplsy(numpts) = yseg
                }
            } if((deta == 0.)&&(b1==b2)&&(c1==c2))  { if(numpts == 0)  {
                    numpts = numpts+1
                    fplsx(numpts) = x1
                    fplsy(numpts) = y1
                } if((numpts > 0) && (fplsx(numpts) != x1) && (fplsy(numpts) != y1) )  {
                    numpts = numpts+1
                    fplsx(numpts) = x1
                    fplsy(numpts) = y1
                } if( (fplsx(numpts) == x1) && (fplsy(numpts) == y1) )  {
```

```
                    fplsx(numpts) = x2
                    fplsy(numpts) = y2
                    }
                else {
                    numpts = numpts+1
                    fplsx(numpts) = x2
                    fplsy(numpts) = y2
                    }
                }
# the end of the points loop
            x1 = x2
            y1 = y2
            }
# end of the if a legal outline section
        }
    i = i+1
    } return
end
# subroutine to translate the 3-D CT focal plane
# points to focal plane coordinates
subroutine coordt(fplsx,fplsy,fplsz,mfplsx,mfplsy,mfplsz,numpts)
integer*4 i
integer*4 numpts real fplsx(10),fplsy(10)
real mfplsx(10),mfplsy(10)
real fplsz,mfplsz(10)

include '../h/recon.h' do i=1,numpts {
    mfplsx(i)=lmb(1)*(fplsx(i)-xfpt)+mu(1)*(fplsy(i)-yfpt)+nu(1)*(fplsz-zfpt)
    mfplsy(i)=lmb(2)*(fplsx(i)-xfpt)+mu(2)*(fplsy(i)-yfpt)+nu(2)*(fplsz-zfpt)
    mfplsz(i)=lmb(3)*(fplsx(i)-xfpt)+mu(3)*(fplsy(i)-yfpt)+nu(3)*(fplsz-zfpt)
    } return
end routine to write a formatted directory
subroutine wrecdir(fdes)
integer*2 fdes
integer*4 i include '../h/dir4.h' write(fdes,'("d")')
write(fdes,'(i8,",",i8,",",i8)') revnum,outsecu,cpsecu outnum(1) = 1
outstar(1) = 1
outnum(2) = 0
outstar(2) = 0 i=1
repeat {
    write(fdes,'(i8,",",i8)') outnum(i),outstar(i)
    i = i+1
    } until(outnum(i-1) == 0)

write(fdes,'("dd")')

return
end routine to write a formatted outline header
subroutine wrecoh(fdes)
integer*2 fdes include '../h/dir4.h'
include '../h/hdr4.h'
```

```
write(fdes,'("h")')

write(fdes,'(i8)') 1 write(fdes,'(i8,",",i8,",",i8)') 6,30,17 write(fdes,'(i8)') 26214 write(fdes,'(a)') patient
write(fdes,'(a)') scancode
write(fdes,'(a)') hospital
write(fdes,'(a)') consult
write(fdes,'(a)') tumsite
write(fdes,'(a)') comment write(fdes,'(i8)') 1 write(fdes,'(i8,",",i8,",",i8)') 1,1,0 write(fdes,'("hh")')

return
end routine to write a formatted outline slice
subroutine wrecsl(fdes)
integer*2 fdes
integer*4 i, j include '../h/dir4.h'
include '../h/hdr4.h'
include '../h/slc4.h' write(fdes,'("s ",i8)') 1 write(fdes,'(i8,",",i8,",",i8,",",i8)') 10,11,12,13 write(fdes,'(i8)') 14 i=1
while(ctypnum(i) != 0) { write(fdes,'(i8)') ctypnum(i)

if(ctypnum(i) == 1) {
        write(fdes,'(i8)') cptscnt(i)
        } else if(ctypnum(i) == 2) {
        write(fdes,'(a)') cdumname(i)
        write(fdes,'(i8)') creldens(i)
        write(fdes,'(i8)') cptscnt(i)
        } else if(ctypnum(i) == 3) {
        write(fdes,'(a)') cdumname(i)
        write(fdes,'(i8)') creldens(i)
        write(fdes,'(i8)') cptscnt(i)
        } else if(ctypnum(i) == 4) {
        write(fdes,'(a)') cdumname(i)
        write(fdes,'(i8)') cptscnt(i)
        } else {
        write(*,'("illegal type = ",i8)') ctypnum(i)
        stop 'wrecsl error'
        } if(cptscnt(i) != 0) {
        do j=1,cptscnt(i) {
            write(fdes,'(i8,",",i8)') cx(i,j),cy(i,j)
            }
        }
```

```
        i = i+1
        } write(fdes,'(i3)') ctypnum(i)
write(fdes,'("ss")')

return
end routine to sort graph points on a slice by slice basis
set up to use i(current) and i-1(previous) slice points
subroutine grsort(mfplsx,mfplsy,dfplsx,dfplsy,slipts,dslipts)

integer*4 slipts,dslipts,diff
real mfplsx(10),mfplsy(10)
real dfplsx(10),dfplsy(10)

include '../h/recon.h' diff = abs(slipts-dslipts)

switch(dslipts) { case 1 :
        oddfpx(ist,jsto) = dfplsx(1)
        oddfpy(ist,jsto) = dfplsy(1)
        oddpts(ist) = oddpts(ist) + 1 jsto=jsto+1 case 2 :
        oddfpx(ist,jsto) = dfplsx(1)
        oddfpy(ist,jsto) = dfplsy(1)
        oddpts(ist) = oddpts(ist) + 1 jsto=jsto+1 evnfpx(ist,jste) = dfplsx(2)
        evnfpy(ist,jste) = dfplsy(2)
        evnpts(ist) = evnpts(ist) + 1
        jste=jste+1 default :
        continue

} return
end
```

Appendix G

```
File _DUA2:[PUBLIC.FTP.PRINTING]XRECON.R;1 (7402,8,0), last revised on 14-NOV-1985 13:47, is a 41 block sequential file owned by
UIC [FTP]. The records are variable length with implied (CR) carriage control. The longest record is 86 bytes Job XRECON (1202) queued to LCAO on 14-NOV-1985 13:47 by user FTP, UIC [FTP], under account SYSTEM at priority 4, started on
printer _LCAO: on 14-NOV-1985 13:53 from queue LCAO.
```

```
ENTRY POINTS: program recon

INPUT/OUTPUT FILES: reci.dat, reco.dat

################################################################
##########################################################

INCLUDE FILES #####

dir4.h
hdr4.h
slc4.h

GLOBAL DATA STRUCTURES AND VARIABLES: #####

# an include file for the directory header block
# integer*4    revnum,
#              outsecu,
#              cpsecu,
#              outnum(306),
#              outstar(306)
# common /direct/revnum,outsecu,cpsecu,outnum,outstar

# an include file for the outline set header block
# integer*4    olinum,
#              day,
#              month,
#              year,
#              picdkey,
#              totslic,
#              slicnum(10),
#              routbln(10),
#              refdist(10)

# common /headi/olinum,day,month,year,
# picdkey,totslic,slicnum,routbln,refdist

# character*65    patient
# character*65    scancode
```

```
# character*65    hospital
# character*65    consult
# character*65    tumsite
# character*65    comment

# common /headc/patient,scancode,hospital,consult,tumsite,comment

# an include file containing all slice parameters
# integer*4    ctlcx,
#              ctlcy,
#              cxleng,
#              cyleng,
#              ctwsdat,
#              ctypnum(8),
#              creldens(8),
#              cptscnt(8),
#              cx(8,500),
#              cy(8,500)

# common /slicei/ctlcx,ctlcy,cxleng,cyleng,ctwsdat,
# ctypnum,creldens,cptscnt,cx,cy

# character*65 cdumname(8)

# common /slicec/cdumname

# an include file for the reconstruction routines
# real fpeqna,fpeqnb,fpeqnc,fpeqnd
# real xfpt,yfpt,zfpt
# real lmb(3),mu(3),nu(3)
# real oddfpx(8,250),oddfpy(8,250),oddfpz(8,250)
# real evnfpx(8,250),evnfpy(8,250),evnfpz(8,250)

# common /rcnsr/fpeqna,fpeqnb,fpeqnc,fpeqnd,xfpt,yfpt,zfpt,
# lmb,mu,nu,oddfpx,oddfpy,oddfpz,evnfpx,evnfpy,evnfpz

# integer*4 oddpts(8),evnpts(8),ist,jsto,jste
# integer*4 fstptx(8),fstpty(8)

# common /rcnsi/oddpts,evnpts,ist,jsto,jste,fstptx,fstpty

################################################################
##########################################################
########################################################## program recon
      character*15 infile
      character*1 chgans
      integer*4    i,j,k,tns,tmpns,slipts,dslipts,lbsgn
      logical*4 filex1,filex2 real magabc,eterm,zspace
      real fpla,fplb,fplc
      real fplsx(10),fplsy(10),fplsz
      real mfplsx(10),mfplsy(10),mfplsz(10)
      real dfplsx(10),dfplsy(10)
      real shift
      real norvecx, norvecy, norvecz include '../h/dir4.h'
      include '../h/hdr4.h'
      include '../h/slc4.h'
      include '../h/recon.h' chgans = 'n'

What files exist?
      inquire(file='fidout.dat',exist=filex2)
      if(filex2 & .true.) {
        open(2, file='fidout.dat', status='old',
     .       access='sequential',form='formatted')
        read(2,'(a15)') infile
        read(2,'(i8)') lbsgn
# zspace in mm convert to cm
        read(2,'(f12.8)') zspace write(6,'("RECON")')
```

```
        write(6,'("Current slice data file:   ",a15)') infile
        write(6,'("Number of reconstruction slices:   ",i8)') lbsgn
        write(6,'("Current z spacing(mm):   ",f12.8)') zspace
        write(6,'(" ")')
        write(6,'("Change current slice data(y or n)?   ",$)')
        read(5,'(a)') chgans

} close(2)

Interactive input inquiry
    if((chgans == 'y') !! (filex2 & .false.)) {
        write(6,'("Changing current slice parameters...")')
        write(6,'("Slice data file?   ",$)')
        read(5,'(a15)') infile
        write(6,'("Number of reconstruction slices?   ",$)')
        read(5,'(i8)') lbsgn
        write(6,'("Enter the slice z-spacing:   ",$)')
        read(5,'(f12.8)') zspace
        write(6,'(" ")')
        chgans = 'n'
        }
    else {
        write(6,'("Slice data file and z spacing remain unchanged")')
        write(6,'(" ")')
        } inquire(file=infile,exist=filex1)

if(filex1 & .true.) {
        open(1, file=infile, status='old',
            access='sequential',form='formatted')
        }
    else {
        write(6,'("The slice data file ",a15," does not exist")') infile
        stop 'open error'
        } inquire(file='reci.dat',exist=filex2)
    if(filex2 & .true.) {
        open(2, file='reci.dat', status='old',
            access='sequential',form='formatted')

read(2,'(f12.8)') fpeqna
        read(2,'(f12.8)') fpeqnb
        read(2,'(f12.8)') fpeqnc
        read(2,'(f12.8)') fpeqnd
        read(2,'(f12.8)') xfpt
        read(2,'(f12.8)') yfpt
        read(2,'(f12.8)') zfpt
        read(2,'(f12.8)') lmb(2)
        read(2,'(f12.8)') mu(2)
        read(2,'(f12.8)') nu(2)

write(6,'("The equation of the focal plane is:")')
        write(6,'("A*x + B*y + C*z = D")')
        write(6,'(" ")')
        write(6,'("Current information:")')
        write(6,'("     The coefficients (A,B,C,D):")')
        write(6,'(3(f12.8,","),f12.8)') fpeqna,fpeqnb,fpeqnc,fpeqnd
        write(6,'(" ")')
        write(6,'("     The focal point (X,Y,Z):")')
        write(6,'(2(f12.8,","),f12.8)') xfpt,yfpt,zfpt
        write(6,'(" ")')
        write(6,'("     The direction cosines (aX,aY,aZ):   ")')
        write(6,'(2(f12.8,","),f12.8)') lmb(2),mu(2),nu(2)
        write(6,'(" ")')

write(6,'("Change current information(y or n)?   ",$)')
        read(5,'(a)') chgans
        }
    else {
        # Interactive input inquiry
        write(6,'("The input file RECI.DAT was not found")')
```

```
        write(6,'(" ")')
        chgans = 'y'
        } if(chgans == 'y') {
    write(6,'("The equation of the focal plane is:")')
    write(6,'("A*x + B*y + C*z = D")')
    write(6,'(" ")')
    write(6,'("Enter the following information:")')
    write(6,'("     The coefficients (A,B,C,D):   ",$)')
    read(5,'(4f12.8)') fpeqna,fpeqnb,fpeqnc,fpeqnd
    write(6,'("     The focal point (X,Y,Z):   ",$)')
    read(5,'(3f12.8)') xfpt,yfpt,zfpt
    write(6,'("     The direction cosines (aX,aY,aZ):   ",$)')
    read(5,'(3f12.8)') lmb(2),mu(2),nu(2)
    write(6,'(" ")')
    } write(6,'("Do you want to shift the focal plane along the optical axis?",$)')
read(5,'(a)') chgans if (chgans == 'y') {
    write(6,'("Enter the desired shift in cm (+:up,-:down)",$)')
    read(5,'(f12.8)') shift
    # calculate the focal point coordinates for the shifted plane
    norvecx = fpeqna/SQRT(fpeqna*fpeqna+fpeqnb*fpeqnb+fpeqnc*fpeqnc)
    norvecy = fpeqnb/SQRT(fpeqna*fpeqna+fpeqnb*fpeqnb+fpeqnc*fpeqnc)
    norvecz = fpeqnc/SQRT(fpeqna*fpeqna+fpeqnb*fpeqnb+fpeqnc*fpeqnc)

xfpt = xfpt + norvecx * shift
    yfpt = yfpt + norvecy * shift
    zfpt = zfpt + norvecz * shift fpeqnd = fpeqna*xfpt + fpeqnb*yfpt + fpeqnc*zfpt
    }
assumes a blank floppy...
starts with the first outline block
# trys to read up to 10 slices per block
# then goes on to the next outline block
# until tns is exhausted
tns = lbsgn
zspace = zspace/10.

# open the data files
open(1, file=infile, status='old', access='sequential',
form='formatted')

inquire(file='reco.dat',exist=filex2)
if(filex2 & .true.) {
    open(2, file='reco.dat',status='old', access='sequential',
    form='formatted')
    rewind 2
    }
else {
    open(2, file='reco.dat',status='new', access='sequential',
    form='formatted')
    } initialize some static array indicies
do i=1,8 {
    oddpts(i) = 0
    evnpts(i) = 0
    }
ist = 1
jstu = 1
jstv = 1 calculate the direction cosines for the +k' axis
input units cm
magabc = (fpeqna*fpeqna)+(fpeqnb*fpeqnb)+(fpeqnc*fpeqnc)
magabc = sqrt(magabc)
lmb(3) = fpeqna/magabc
mu(3) = fpeqnb/magabc
nu(3) = fpeqnc/magabc
```

```
# orientation check for direction
cosine to find the e term
# if(fpeqnc == 0. ) {
#     if(fpeqnb == 0. ) {
#         eterm = fpeqna
#         }
else {
#         eterm = fpeqnb
#         }
}
else {
#     eterm = fpeqnc
#     }

# if(eterm > 0. ) {
#     eterm = 1.
#     }
else {
#     eterm = -1.
#     }

# The above logic was to select the orientation of the z'
# axis; however in practice the procedure supplied an
# interesting random sequence of mirror images.  This was
# corrected by making eterm = 1 permenantly.
eterm = 1.

# set direction
lmb(3) = lmb(3)*eterm
mu(3) = mu(3)*eterm
nu(3) = nu(3)*eterm calculate the direction cosines
for the +i' axis
# Also the t term is chosen to be -1
# to orient the plane correctly
# for display
lmb(1) = 1.*( mu(2)*nu(3) - mu(3)*nu(2) )
mu(1)  = 1.*( nu(2)*lmb(3) - nu(3)*lmb(2) )
nu(1)  = 1.*(.lmb(2)*mu(3) - lmb(3)*mu(2) )

call rfdirect(1)

i=1
tmpns = tns
fplsz = 0.
while ((outnum(i) != 0) && (tmpns != 0))  { call rfouth(1,outstar(i))

do j=1,totslic {
        call rfslic(1, outstar(i), j)

# on a per slice basis
        fpla = fpeqna
        fplb = fpeqnb
        fplc = fpeqnc*fplsz - fpeqnd call perslic(fpla,fplb,fplc,fplsx,fplsy,slipts)

call coordt(fplsx,fplsy,fplsz,mfplsx,mfplsy,mfplsz,slipts)

# here is where we insert the proper sorting technique
whatever it may be, such as a store delay procedure if j > 1 then delay system is primed
        if(j > 1) {
            call grsort(mfplsx,mfplsy,dfplsx,dfplsy,slipts,dslipts)
            } delay step forward
        dslipts = slipts
        do k=1,dslipts {
            dfplsx(k) = mfplsx(k)
            dfplsy(k) = mfplsy(k)
```

```
            fplsz = fplsz + zspace
            } flush the last points from the delay array
        call grsort(mfplsx,mfplsy,dfplsx,dfplsy,slipts,dslipts)

tmpns = tmpns-totslic
        i = i+1
        } initialize ctypnum and cptscnt
do i=1,8 {
    ctypnum(i) = 0
    cptscnt(i) = 0
    } do i=1,ist {
    ctypnum(i) = 1
    cptscnt(i) = oddpts(i) + evnpts(i)
    } do i=1,ist {
    do j=1,oddpts(i) {
        if(j == 1) {
            fstptx(i) = int(oddfpx(i,j)*160.)
            fstpty(i) = int(oddfpy(i,j)*160.)
            } cx(i,j) = int(oddfpx(i,j)*160.)
        cy(i,j) = int(oddfpy(i,j)*160.)
        } do j=(oddpts(i)+1),cptscnt(i) {
            cx(i,j) = int(evnfpx(i,(cptscnt(i)+1-j))*160.)
            cy(i,j) = int(evnfpy(i,(cptscnt(i)+1-j))*160.)
            }
        } make the connection to complete the contour
do i=1,ist {
    cptscnt(i) = cptscnt(i) + 1
    cx(i,cptscnt(i)) = fstptx(i)
    cy(i,cptscnt(i)) = fstpty(i)
    } call wrecdir(2)
call wrecoh(2)
call wrecsl(2)

close(1)
close(2)
end routine to read a formatted directory sector
subroutine ffdirect(fdes)
integer*2   fdes
integer*4   i
character*1 start
character*2 finish include '../h/dir4.h' read(fdes,'(a1)') start read(fdes,'(i8,1x,i8,1x,i8)') revnum,outsecu,cpsecu i=1
repeat {
    read(fdes,'(i8,1x,i8)') outnum(i),outstar(i)
    i = i+1
    } until (outnum(i-1) == 0)

read(fdes,'(a2)') finish return
end
```

```
# routine to write a formatted directory
subroutine wfdirect(fdes)
integer*2   fdes
integer*4   i include '../h/dir4.h' write(fdes,'("d")')

write(fdes,'(i8,",",i8,",",i8)') revnum,outsecu,cpsecu i=1
repeat {
    write(fdes,'(i8,",",i8)') outnum(i),outstar(i)
    i = i+1
    } until (outnum(i-1) == 0)

write(fdes,'("dd")')

return
end routine to read an unformatted outline header
subroutine rfouth(fdes, sectnum)
integer*2   fdes
integer*4   sectnum,i character*1 start
character*2 finish include '../h/dir4.h'
include '../h/hdr4.h' read(fdes,'(a1)') start read(fdes,'(i8)') olinum
read(fdes,'(i8,1x,i8,1x,i8)') day,month,year
read(fdes,'(a)') patient
read(fdes,'(a)') scancode
read(fdes,'(a)') hospital
read(fdes,'(a)') consult
read(fdes,'(a)') tumsite
read(fdes,'(a)') comment read(fdes,'(i8)') totslic do i=1,totslic {
    read(fdes,'(i8,1x,i8,1x,i8)') slicnum(i),routbln(i),refdist(i)
    } read(fdes,'(a2)') finish return
end routine to write a formatted outline header
subroutine wfouth(fdes, sectnum)
integer*2   fdes
integer*4   sectnum,i include '../h/dir4.h'
include '../h/hdr4.h' write(fdes,'("h")')

write(fdes,'(i8)') olinum
write(fdes,'(i8,",",i8,",",i8)') day,month,year
write(fdes,'(i8)') picdkey write(fdes,'(a)') patient
write(fdes,'(a)') scancode
write(fdes,'(a)') hospital
write(fdes,'(a)') consult
write(fdes,'(a)') tumsite
write(fdes,'(a)') comment
```

```
write(fdes,'(i8)') totslic do i=1,totslic {
    write(fdes,'(i8,",",i8,",",i8)') slicnum(i),
    routbln(i),refdist(i)
    } write(fdes,'("hh")')

return
end routine to read a formatted outline slice
subroutine rfslic(fdes, sectnum, nslice)
integer*2   fdes
integer*4   sectnum,
            nslice,
            i,j
# on a per slice basis and the contour(s)
# within a desired slice
# output is returned within the arrays fplsx and fplsy
subroutine perslic(fpla,fplb,fplc,fplsx,fplsy,numpts)
integer*4   i,j
integer*4   numpts real fpla,fplb,fplc
real fplsx(10),fplsy(10)
real x1,y1,x2,y2,xseg,yseg
real a1,b1,c1,a2,b2,c2,deta include '../h/dir4.h'
include '../h/hdr4.h'
include '../h/slc4.h' numpts = 0 a2 = fpla
b2 = fplb
c2 = -1.+fplc i=1
while(ctypnum(i) != 0)  { if((ctypnum(i) != 4)&&(cptscnt(i) > 4))  { x1 = real(cx(i,1))/160.
        y1 = real(cy(i,1))/160.
        do j=2,cptscnt(i) {
            x2 = real(cx(i,j))/160.
            y2 = real(cy(i,j))/160.

a1 = y1 - y2
            b1 = x2 - x1
            c1 = y1*b1 + x1*a1 deta = a1*b2 - a2*b1
            if(deta != 0.) {
                xseg = (b2*c1 - b1*c2)/deta
                yseg = (a1*c2 - a2*c1)/deta
                if( (( (xseg >= min(x1,x2)) && (xseg < max(x1,x2)) ) ||
                    ( (yseg >= min(y1,y2)) && (yseg < max(y1,y2)) ) ) {
                    numpts = numpts+1
                    fplsx(numpts) = xseg
                    fplsy(numpts) = yseg
                    }
                } if((deta == 0.)&&(b1==b2)&&(c1==c2))  { if(numpts == 0)  {
                    numpts = numpts+1
                    fplsx(numpts) = x1
                    fplsy(numpts) = y1
                    } if((numpts > 0) && (fplsx(numpts) != x1) && (fplsy(numpts) != y1) )  {
                    numpts = numpts+1
```

```
                fplsx(numpts) = x1
                fplsy(numpts) = y1
                } if( (fplsx(numpts) == x1) && (fplsy(numpts) == y1) )  {
                fplsx(numpts) = x2
                fplsy(numpts) = y2
                }
            else {
                numpts = numpts+1
                fplsx(numpts) = x2
                fplsy(numpts) = y2
                }
            }
# the end of the points loop
        x1 = x2
        y1 = y2
        }
# end of the if a legal outline section
        }
    i = i+1
    } return
end
# subroutine to translate the 3-D CT focal plane
# points to focal plane coordinates
subroutine coordt(fplsx,fplsy,fplsz,mfplsx,mfplsy,mfplsz,numpts)
integer*4 i
integer*4 numpts real fplsx(10),fplsy(10)
real mfplsx(10),mfplsy(10)
real fplsz,mfplsz(10)

include '../h/recon.h' do i=1,numpts {
    mfplsx(i)=lmb(1)*(fplsx(i)-xfpt)+mu(1)*(fplsy(i)-yfpt)+nu(1)*(fplsz-zfpt)
    mfplsy(i)=lmb(2)*(fplsx(i)-xfpt)+mu(2)*(fplsy(i)-yfpt)+nu(2)*(fplsz-zfpt)
    mfplsz(i)=lmb(3)*(fplsx(i)-xfpt)+mu(3)*(fplsy(i)-yfpt)+nu(3)*(fplsz-zfpt)
    } return
end routine to write a formatted directory
subroutine wrecdir(fdes)
integer*2 fdes
integer*4 i include '../h/dir4.h' write(fdes,'("d")')
write(fdes,'(i8,",",i8,",",i8)') revnum,outsecu,cpsecu outnum(1) = 1
outstar(1) = 1
outnum(2) = 0
outstar(2) = 0 i=1
repeat  {
    write(fdes,'(i8,",",i8)') outnum(i),outstar(i)
    i = i+1
    } until(outnum(i-1) == 0)

write(fdes,'("dd")')

return
end routine to write a formatted outline header
subroutine wrecoh(fdes)
integer*2 fdes
```

```
include '../h/dir4.h'
include '../h/hdr4.h' write(fdes,'("h")')

write(fdes,'(i8)') 1 write(fdes,'(i8,",",i8,",",i8)') 6,30,17 write(fdes,'(i8)') 26214 write(fdes,'(a)') patient
write(fdes,'(a)') scancode
write(fdes,'(a)') hospital
write(fdes,'(a)') consult
write(fdes,'(a)') tumsite
write(fdes,'(a)') comment write(fdes,'(i8)') 1 write(fdes,'(i8,",",i8,",",i8)') 1,1,0 write(fdes,'("hh")')

return
end routine to write a formatted outline slice
subroutine wrecsl(fdes)
integer*2 fdes
integer*4 i, j include '../h/dir4.h'
include '../h/hdr4.h'
include '../h/slc4.h' write(fdes,'("s ",i8)') 1 write(fdes,'(i8,",",i8,",",i8,",",i8)') 10,11,12,13
write(fdes,'(i8)') 14 i=1
while(ctypnum(i) != 0)  { write(fdes,'(i8)') ctypnum(i)

if(ctypnum(i) == 1) {
        write(fdes,'(i8)') cptscnt(i)
        } else if(ctypnum(i) == 2) {
        write(fdes,'(a)') cdumname(i)
        write(fdes,'(i8)') creldens(i)
        write(fdes,'(i8)') cptscnt(i)
        } else if(ctypnum(i) == 3) {
        write(fdes,'(a)') cdumname(i)
        write(fdes,'(i8)') creldens(i)
        write(fdes,'(i8)') cptscnt(i)
        } else if(ctypnum(i) == 4) {
        write(fdes,'(a)') cdumname(i)
        write(fdes,'(i8)') cptscnt(i)
        } else {
        write(*,'("illegal type = ",i8)') ctypnum(i)
        stop 'wrecsl error'
        } if(cptscnt(i) != 0) {
        do j=1,cptscnt(i) {
            write(fdes,'(i8,",",i8)') cx(i,j),cy(i,j)
```

```
            }
        }
        i = i+1
    } write(fdes,'(i8)') ctypnum(i)
write(fdes,'("ss")') .

return
end routine to sort graph points on a slice by slice basis
set up to use i(current) and i-1(previous) slice points
subroutine grsort(mfplsx,mfplsy,dfplsx,dfplsy,slipts,dslipts)

integer*4 slipts,dslipts,diff
real mfplsx(10),mfplsy(10)
real dfplsx(10),dfplsy(10)

include '../h/recon.h' diff = abs(slipts-dslipts)
switch(dslipts) { case 1 :
        oddfpx(ist,jsto) = dfplsx(1)
        oddfpy(ist,jsto) = dfplsy(1)
        oddpts(ist) = oddpts(ist) + 1 jsto=jsto+1 case 2 :
        oddfpx(ist,jsto) = dfplsx(1)
        oddfpy(ist,jsto) = dfplsy(1)
        oddpts(ist) = oddpts(ist) + 1 jsto=jsto+1 evnfpx(ist,jste) = dfplsx(2)
        evnfpy(ist,jste) = dfplsy(2)
        evnpts(ist) = evnpts(ist) + 1 jste=jste+1 default :
        continue

} return
end
```

Digital Equipment Corporation - VAX/VMS Version V4.1

```
FFFFF  TTTTT  PPPP
F        T    P   P
F        T    P   P
FFFF     T    PPPP
F        T    P
F        T    P
F        T    P
```

Appendix H.

```
DDDDDDD   IIIIII   SSSSSSSS  PPPPPPPP
DDDDDDD   IIIIII   SSSSSSSS  PPPPPPPP
DD   DD     II    SS         PP    PP
DD   DD     II    SS         PP    PP
DD   DD     II    SS         PP    PP
DD   DD     II    SS         PP    PP
DD   DD     II     SSSSSS    PPPPPPPP
DD   DD     II         SSSS  PPPPPPPP
DD   DD     II            SS PP
DD   DD     II            SS PP
DD   DD     II            SS PP
DD   DD     II    SS      SS PP
DDDDDDD   IIIIII   SSSSSSSS  PP
DDDDDDD   IIIIII   SSSSSSSS  PP
```

```
   RRRRRRR            ....        11
   RRRRRRR            ....        11
   RR    RR           ....       111
   RR    RR           ....      1111
   RR    RR           ....        11
   RR    RR           ....        11
   RRRRRRR            ....        11
   RRRRRRR            ....        11
   RR  RR             ....        11
   RR   RR            ....        11
   RR   RR            ..          11
   RR    RR           ..          11
   RR    RR           ..       111111
   RR     RR          ..       111111
```

File _DUA2:[PUBLIC.FTP.PRINTING]DISP.R;1 (1781,15,0), last revised on 14-NOV-1985 13:47, is a 29 block sequential file owned by UIC [FTP]. The records are variable length with implied (CR) carriage control. The longest record is 89 bytes.

Job DISP (1198) queued to LCAO on 14-NOV-1985 13:47 by user FTP, UIC [FTP], under account SYSTEM at priority 4, started on printer _LCAO: on 14-NOV-1985 13:50 from queue LCAO.

Digital Equipment Corporation - VAX/VMS Version V4.1

```
#############################################################
#############################################################
#############################################################

FILE NAME:  disp.r

VERSION:    1.0

PROGRAMMER:  William J. Murray

DATE OF CREATION:  2/10/85

ENTRY POINTS:  program disp

INPUT/OUTPUT FILES:  reco.dat

#############################################################
#############################################################
#############################################################

INCLUDE FILES #####

#   dir2.h
#   hdr2.h
#   slc2.h

GLOBAL DATA STRUCTURES AND VARIABLES: #####

# an include file for the floppy directory
# integer*2   revnum,           # revision number
#             outsecu,          # number of outline sectors used
#             cpsecu,           # number of C.P. Sectors used
#             outnum(306),      # Outline Number
#             outstar(306)      # Start Sector
# common /direct/revnum,outsecu,cpsecu,outnum,outstar

# an include file for the outline set header block
# integer*2   olinum,           # the outline number
#             day,              # the day
#             month,            # the month
```

```
#                       year,              # the (year - 1968)
#                       picdkey,           # the picture diameter key
#                       totslic,           # the total number of slices
#                       slicnum(10),       # the slice number
#                       routbln(10),       # Relative outline block number
#                       refdist(10)        # +/- distance from reference (mm/16)

# common /headi/olinum,day,month,year,
# picdkey,totslic,slicnum,routbln,refdist

# character*65      patient
# character*65      scancode
# character*65      hospital
# character*65      consult
# character*65      tumsite
# character*65      comment

# common /headc/patient,scancode,hospital,consult,tumsite,comment

# an include file for current slice data
# integer*2    ctlcx,                # current top left corner x (mm/16)
#              ctlcy,                # current top left corner y (mm/16)
#              cxleng,               # current x length (mm/16)
#              cyleng,               # current y length (mm/16)
#              ctwsdat,              # current total words of slice data
#              ctypnum(8),           # current type number
#              creldens(8),          # current relative density
#              cptscnt(8),           # current points count
#              cx(8,500),            # current x coordinate value
#              cy(8,500)             # current y coordinate value

# common /slicei/ctlcx,ctlcy,cxleng,cyleng,ctwsdat,
# ctypnum,creldens,cptscnt,cx,cy

# character*65 cdumname(8)

# common /slicec/cdumname

# integer*2 jcol1,jcol2,jrow1,jrow2,iopt

# common /ploti/ jcol1,jcol2,jrow1,jrow2,iopt

# real xmin,xmax,ymin,ymax
# real xorg,yorg,yoverx,aspect
# real arc(2,2),theta,tx,ty,txorg,tyorg
# real scalex,scaley,magfact
# real xpxl,ypxl,minxout,minyout

# common /plotr1/ xmin,xmax,ymin,ymax,xorg,yorg,yoverx,
# aspect,arc,theta,tx,ty,txorg,tyorg,scalex,scaley,magfact,
# xpxl,ypxl,minxout,minyout

###############################################################
#########################################################
######################################################### program disp
integer*4 chgflag
integer*2 gmode,tmode,fdes
character*1 answer
logical*4 filex include '../h/dir2.h'
include '../h/hdr2.h'
include '../h/slc2.h'
include '../h/plot.h' answer = 'y'
chgflag = 0
fdes = 2
gmode = 6
tmode = 2 text mode
call qsmode(tmode)

# file handling
```

```
open(1, file='reco.dat', status='old', access='sequential',
form='formatted')
if(filex & .true.)  { open(2, file='rotsctr.dat', status='old', access='sequential',
form='formatted')
    }
else  { open(2, file='rotsctr.dat', status='new', access='sequential',
form='formatted')

call pinit(2,chgflag)
close(2)

open(2, file='rotsctr.dat', status='old', access='sequential',
form='formatted')

} the outline number and slice number will always
be 1 and 1 in the reconstruction
call rfdirect(1)
call rfouth(1,outstar(1))
call rfslic(1, outstar(1), 1)

# read update of plot parameters
call plotrup(fdes,chgflag)

repeat {
    # graphics mode
    call qsmode(gmode)
    continue
    call plots(outstar(1),1)
    write(6,'("Change parameters(y or n)?  ",$)')
    read(5,'(a1)') answer
    if(answer == 'n')  break
    call qsmode(tmode)
    continue
    call menu(chgflag)
    } until(answer != 'y')

# text mode
call qsmode(tmode)
continue update the parameters if they have been changed
if(chgflag != 0)  {
    call plotwup(fdes,chgflag)
    } close(1)
close(2)
end routine to read a formatted directory sector
subroutine rfdirect(fdes)
integer*2   fdes
integer*4   i
character*1 start
character*2 finish include '../h/dir2.h' read(fdes,'(a1)') start read(fdes,'(i8,1x,i8,1x,i8)') revnum,outsecu,cpsecu i=1
repeat {
    read(fdes,'(i8,1x,i8)') outnum(i),outstar(i)
    i = i+1
    } until (outnum(i-1) == 0)
```

```
read(fdes,'(a2)') finish return
end routine to read a formatted outline header
subroutine rfouth(fdes, sectnum)
integer*2    fdes
integer*4    sectnum,i character*1 start
character*2 finish include '../h/dir2.h'
include '../h/hdr2.h' read(fdes,'(a1)') start read(fdes,'(i8)') olinum
read(fdes,'(i8,1x,i8,1x,i8)') day,month,year
read(fdes,'(i8)') picdkey read(fdes,'(a)') patient
read(fdes,'(a)') scancode
read(fdes,'(a)') hospital
read(fdes,'(a)') consult
read(fdes,'(a)') tumsite
read(fdes,'(a)') comment read(fdes,'(i8)') totslic do i=1,totslic {
    read(fdes,'(i8,1x,i8,1x,i8)') slicnum(i),routbln(i),refdist(i)
    } read(fdes,'(a2)') finish return
end routine to read a formatted outline slice
subroutine rfslic(fdes, sectnum, nslice)
integer*2    fdes
integer*4    sectnum,
             nslice,
             i,j character*1 start
character*2 finish include '../h/dir2.h'
include '../h/hdr2.h'
include '../h/slc2.h' read(fdes,'(a1,1x,i8)') start,nslice read(fdes,'(i8,1x,i8,1x,i8,1x,i8)') ctlcx,ctlcy,cxleng,cyleng read(fdes,'(i8)') ctwsdat i=1
read(fdes,'(i8)') ctypnum(i)
while(ctypnum(i) != 0) { if(ctypnum(i) == 1) {
        read(fdes,'(i8)') cptscnt(i)
        if(cptscnt(i) < 3) {
            write(*,*)' '
            write(*,*)'No intersection between focal plane and tumor'
            stop
            }
        } else if(ctypnum(i) == 2) {
        read(fdes,'(a)') cdumname(i)
```

```
            read(fdes,'(i8)') creldens(i)
            read(fdes,'(i8)') cptscnt(i)
            } else if(ctypnum(i) == 3) {
            read(fdes,'(a)') cdumname(i)
            read(fdes,'(i8)') creldens(i)
            read(fdes,'(i8)') cptscnt(i)
            } else if(ctypnum(i) == 4) {
            read(fdes,'(a)') cdumname(i)
            read(fdes,'(i8)') cptscnt(i)
            } else {
            write(6,'("Illegal Type Number = ",i8)') ctypnum(i)
            stop 'rfslic error'
            } do j=1,cptscnt(i) {
            read(fdes,'(i8,1x,i8)') cx(i,j),cy(i,j)
            } i = i+1
        read(fdes,'(i8)') ctypnum(i)
        } read(fdes,'(a2)') finish return
end routine to plot a formatted data set
subroutine plots(sectnum,nslice)
integer*4   sectnum,
            nslice,
            i,
            j,
            k,
            outbnd,
            arybnd
integer*2   npts,gmode,tmode,piop
real tmpx,tmpy,px1(500),py1(500),px2(500),py2(500),piy
real xprime,yprime include '../h/dir2.h'
include '../h/hdr2.h'
include '../h/slc2.h'
include '../h/plot.h' gmode = 6
tmode = 2
call qsmode(gmode)

piop = iopt
piy = ymax
outbnd = 0 call qplot plot setup
call qplot(jcol1,jcol2,jrow1,jrow2,xmin,xmax,ymin,piy,xorg,yorg,piop,yoverx,aspect)

xpxl = xmax/320.
ypxl = ymax/100.

i=1
while(ctypnum(i) != 0) { if(!(((ctypnum(i)==4)&&(cptscnt(i) == 2))) { minxout = 100000.
        minyout = 100000.
        do j=1,cptscnt(i) {
            tmpx=real(cx(i,j))
            tmpy=real(cy(i,j))
            px1(j)=xprime(tmpx,tmpy)
            py1(j)=yprime(tmpx,tmpy)
```

```
                if( (abs(px1(j)) < minxout) && (abs(py1(j)) < minyout) )  {
                    minxout = px1(j)
                    minyout = py1(j)
                    }
                } window the array values
            npts=0
            j=1
            k=1
            arybnd = 0
            while(j <= cptscnt(i))  { if((px1(j) >= xmin)&&(px1(j) <= xmax)&&(py1(j) >= ymin)&&(py1(j) <= ymax)) {
                    px2(k) = px1(j)
                    py2(k) = py1(j)
                    npts = npts+1
                    k = k+1
                    outbnd = 1
                    arybnd = 1
                    }
                else {
                    arybnd = 0
                    } if( ((npts > 0)&&(arybnd==0)) || ((npts > 0)&&(j == cptscnt(i))) )  {
                    call qtabl(1,npts,px2,py2)
                    npts = 0
                    k = 1
                    } j = j+1

}
            }
        i = i+1
        } if(outbnd == 0)  {
    call qsmode(tmode)
    continue
    write(6,'("All contour values fall outside window range")')
    write(6,'("Minimum x = ",f12.8)') minxout
    write(6,'("Minimum y = ",f12.8)') minyout
    } return
end routine to read a file containing the display parameters
subroutine plotrup(fdes, chgflag)
integer*2    fdes
integer*4    chgflag include '../h/plot.h' rewind 2 read(fdes,'(5i8)') jcol1,jcol2,jrow1,jrow2,iopt read(fdes,'(4f12.6)') xmin,xmax,ymin,ymax read(fdes,'(4f12.6)') xorg,yorg,yoverx,aspect read(fdes,'(2f12.6)') are(1,1),are(1,2)
read(fdes,'(2f12.6)') are(2,1),are(2,2)

read(fdes,'(2f12.6)') tx,ty
read(fdes,'(2f12.6)') txorg,tyorg
read(fdes,'(f12.6)') theta
read(fdes,'(3f12.6)') scalex,scaley,magfact chgflag = 0 return
end
```

```
# routine to write a file containing the display parameters
subroutine plotwup(fdes, chgflag)
integer*2    fdes
integer*4    chgflag include '../h/plot.h' rewind 2 write(fdes,'(5i8)') 0, 639, 0, 199, 1 write(fdes,'(4f12.6)') -2515.0, 2499.0, -1933.0, 1946.0 write(fdes,'(4f12.6)') 320.0, 100.0, 1.08, 1.28 write(fdes,'(2f12.6)') are(1,1),are(1,2)
write(fdes,'(2f12.6)') are(2,1),are(2,2)

write(fdes,'(2f12.6)') tx, ty write(fdes,'(2f12.6)') txorg, tyorg
write(fdes,'(f12.6)') theta
write(fdes,'(3f12.6)') scalex, scaley, magfact chgflag = 0 return
end routine to write a file containing the display parameters
subroutine pinit(fdes, chgflag)
integer*2    fdes
integer*4    chgflag include '../h/plot.h' write(fdes,'(5i8)') 0, 639, 0, 199, 1 write(fdes,'(4f12.6)') -2515.0, 2499.0, -1933.0, 1946.0 write(fdes,'(4f12.6)') 320.0, 100.0, 1.08, 1.28 write(fdes,'(2f12.6)') 1.0, 0.0
write(fdes,'(2f12.6)') 0.0, 1.0 write(fdes,'(2f12.6)') 0.0, 0.0 write(fdes,'(2f12.6)') 0.0, 0.0
write(fdes,'(f12.6)') 0.0
write(fdes,'(3f12.6)') 1.0, 1.0, 1.0 chgflag = 0 return
end menu interface routine
subroutine menu(chgflag)
integer*2 tmode
integer*4 chgflag, option
real phi
character*1 retr include '../h/plot.h' tmode = 2
call qtmode(tmode)

write(6,'("Select from below the number corresponding to")')
write(6,'("the parameters you wish to alter:")')
write(6,'(" ")')
write(6,'("     1  Translate ")')
write(6,'("     2  Scale ")')
write(6,'("     3  Rotate ")')
write(6,'("     4  Crosshair ")')
write(6,'("     5  Magnification Factor ")')
```

```
write(6,'("      6  Cancel change and redraw ")')
write(6,'(" ")')

write(6,'("Pixel X dimension = ",f12.8)') xpxl
write(6,'("Pixel Y dimension = ",f12.8)') ypxl
write(6,'("Enter option selection:   ",$)')
read(5,'(i8)') option switch(option) {
    case 1 :
    write(6,'("Current origin (x1,y1) = (",f12.6,",",f12.6,")")') txorg,tyorg
    write(6,'(" ")')
    write(6,'("Enter new origin x1,y1:   ",$)')
    read(5,'(f12.6,f12.6)') txorg,tyorg
    chgflag = 1 case 2 :
    write(6,'("Current scale factors (sx,sy) = (",f12.6,",",f12.6,")")') scalex,scaley
    write(6,'(" ")')
    write(6,'("Enter new scale factors sx,sy:   ",$)')
    read(5,'(f12.6,f12.6)') scalex,scaley
    chgflag = 1 case 3 :
    write(6,'("Rotation is given as a constant theta * pi")')
    write(6,'("where 0.5*pi = positive 90 degrees")')
    write(6,'("Current theta = ",f12.6)') theta
    write(6,'(" ")')
    write(6,'("Enter new theta value:   ",$)')
    read(5,'(f12.6)') theta
    chgflag = 1 case 4 :
    # the crosshair
    call qsmode(6)
    call qline(0,100,639,100,3)
    call qline(320,0,320,199,3)
    call qline(320,100,639,199,3)
    write(6,'("Hit a key to replot",$)')
    read(5,'(a)') retr case 5 :
    write(6,'("Magnification factor is a constant related to")')
    write(6,'("the magnification setting on the microscope")')
    write(6,'("Current magnification setting = ",f12.6)') magfact
    write(6,'(" ")')
    write(6,'("Enter new magnification setting:   ",$)')
    read(5,'(f12.6)') magfact
    chgflag = 1 default:
        continue

} if(chgflag == 1) {
    phi=3.1415927*theta
    are(1,1)=magfact*scalex*cos(phi)
    are(1,2)=magfact*scalex*sin(phi)
    are(2,1)=-1.*magfact*scaley*sin(phi)
    are(2,2)=magfact*scaley*cos(phi)
    tx=-1.*txorg*magfact*scalex*cos(phi)+tyorg*magfact*scaley*sin(phi)
    ty=-1.*tyorg*magfact*scaley*cos(phi)-txorg*magfact*scalex*sin(phi)
    } return
end x' function
function xprime(x,y)
real xprime,x,y include '../h/plot.h' xprime = x*are(1,1) + y*are(2,1) + tx return
end
```

```
if y' function
function yprime(x,y)
real yprime,x,y include '../h/plot.h' yprime = x*are(1,2) + y*are(2,2) + ty return
end
```

What is claimed is:

1. A method of integrating image information from an imaging device and an operating microscope during an operative procedure on body parts of a patient comprising:
   positioning an operating microscope in the course of said operative procedure at an operative location relative to the patient;
   establishing the spatial relationship among the image information, the patient, and the focal plane of the microscope;
   introducing the image information and spatial relationship to a computer and reformatting the image information to generate a computer-generated image of the body part at a determined plane related to the focal plane of the microscope; and
   projecting the computer-generated image into the optics of the operating microscope for coordinated viewing of the computer-generated image and the patient.

2. A method according to claim 1 that that includes providing a plurality of fiducials which are physically detectable and which are disposed at a position exposed to the microscope to permit positioning of the fiducials at a fixed point in the focal plane of the microscope.

3. A method according to claim 2 comprising providing at least three fiducials.

4. A method according to claim 2 comprising providing fiducials are spatially fixed with respect to the patient to permit accurate location of anatomic and/or pathologic structures of interest.

5. A method according to claim 4 that comprises establishing the spatial relationship between the microscope, the patient, and the imaging information using a three-dimensional ultrasonic range finder whose output is digitized, the microscope being positioned in space relative to the patient by placing each fiducial sequentially at the focal point and then using an acoustic range finder to determine each respective position of the microscope relative to the respective fiducial.

6. A method of referencing for integrating information received from an imaging device and an operating microscope during an operative procedure on a body part of a patient, that comprises:
   introducing said information to a computer which is operable to reformat the received information which is then presented as a computer-generated image of the body part at a determinable place;
   positioning an operating microscope in the course of said operative procedure at an operative location relative to the patient, the focal plane of the microscope being at said determinable plane;
   establishing the spatial relationship among the computer-generated image, the patient and the focal plane of the microscope; and
   projecting the computer-generated image into the optics of the operating microscope.

7. A reference display system to receive information from an imaging system that extracts three-dimensional information about a part of the body of a patient, the system comprising:
   an operating microscope positioned in an operative location relative to the patient;
   means for establishing the spatial relationship among the imaging system information, the patient, and the focal plane of the microscope;
   computer means connected to received the information from the imaging system and from said means for establishing the spatial relationship and programmed to reformat the information from the imaging system to provide an output signal representative of a computer-generated image corresponding to a determined plane having a predetermined relationship with the focal plane of the microscope; and
   means to project the computer-generated image for coordinated viewing of the computer-generated image and the patient through the operating microscope.

8. Apparatus that includes the reference display system according to claim 7 and that further includes an imaging system in the form of a CT scan.

9. Apparatus that includes the reference display system according to claim 7 and that further includes an imaging system in the form of a magnetic resonance imaging (MRI) scanner.

10. Apparatus that includes the reference display system according to claim 7 and that further includes an imaging system in the form of a position emission tomography (PET) scanner.

11. Apparatus that includes the reference display system according to claim 7 that further includes an imaging system in the form of an ultrasound imaging device.

12. A system according to claim 7 in which the means for establishing the spatial relationship comprises a three-dimensional ultrasonic range finder whose output is digitized.

13. A system according to claim 12 in which the range finder operates at about 50 to 60 kHz.

14. A system according to claim 12 in which the range finder comprises a spark gap that serves as a source of sound pulses, which spark gap is located on the microscope a fixed distance from the focal plane of the microscope.

15. A system according to claim 14 having at least three microphones to establish uniquely the location of the spark gap with respect to three microphones whose positions are fixed in the operating room.

16. A system according to claim 3 having three spark gaps to determine uniquely the position and orientation of the microscope with respect to the microphones.

17. A system according to claim 7 that includes a plurality of fiducials which are physically detectable by the imaging system and are disposed at a position exposed to the microscope to permit positioning of the fiducials at a fixed point in the focal plane of the microscope.

18. A system according to claim 17 comprising at least three fiducials.

19. A system according to claim 17 wherein the fiducials are spatially fixed with respect to the patient to permit accurate location of anatomic and/or pathologic structures of interest.

20. A system according to claim 17 wherein the means for establishing the spatial relationship between the microscope, the patient, and the imaging information comprises a three-dimensional ultrasonic range finder whose output is digitized and wherein the microscope is positioned in space relative to the patient by placing each fiducial sequentially at the focal point and then using the acoustic range finder to determine each respective position of the microscope relative to the respective fiducial.

21. A system according to claim 20 in which the determinable plane of the image data is established by slant-range information from the acoustic range finder which determines the position of the focal plane of the microscope, that is, slant-range information and orientation information which is fed as input information to the computer means which, on the basis of the input information, establishes the position of the focal plane of the microscope relative to the patient, the slant-range distance being the distance between any spark gap and any microphone.

22. A system according to claim 7 in which the appropriate reformatted image at the determined plane, based on the imaging system information, is displayed on a cathode ray tube (CRT) which is mounted on the operating microscope in conjunction with a beam-splitting assembly in a way that a person looking through the operating microscope sees both the operative field and the reformatted image superposed upon one another.

23. A system according to claim 22 that includes an optics system between the beam splitter and the screen of the CRT so that the plane of the screen is in focus to the surgeon.

24. A system according to claim 23 wherein the appropriate reformatted image is determined by the position of the microscope image plane or such other parallel (or other) plane that the surgeon may request.

25. A system according to claim 7 in which the means for establishing the spatial relationship comprises a three-dimensional magnetic range finder system whose output is digitized.

26. A system according to claim 25 in which the range finder comprises a source and a tracker (receiver), the source being located at a fixed spatial position and the tracker being located on the microscope.

27. A system according to claim 26 in which the source comprises three electrical coils, oriented at an angle to one another, each being excited sequentially to produce a three-state magnetic field.

28. A system according to claim 26 in which the tracker determines uniquely the position and orientation of the microscope with respect to the source, and comprises three electrical coils, oriented at an angle to one another, in which three voltages are induced in the tracker system by the magnetic field for each of the source coils.

29. A system according to claim 28 in which said angle is a right angle.

30. A system according to claim 25 in which the range finder comprises a source and a tracker, the tracker being located at a fixed spatial position and the source being located on the microscope.

31. A system according to claim 30 in which the source comprises three electric coils oriented at an angle to one another, each being excited sequentially to produce a three-state magnetic field, and in which the tracker comprises three electrical coils positioned at an angle to one another and adapted to generate a voltage derived from an induced field on the basis of electromagnetic wave energy received from the source coils.

32. A system according to claim 19 wherein the means for establishing the spatial relationship between the source, the patient, and the imaging information comprises a three-dimensional magnetic range finder whose output is digitized and wherein the microscope is positioned in space relative to the imaging system by placing each fiducial sequentially at the focal point and then using the magnetic range finder to determine the position of each fiducial relative to the fixed element of the source-tracker system.

33. A system according to claim 32 in which the determinable plane of the image data is established by information from the magnetic range finder which determines the position of the focal plane of the microscope which is fed as input information to the computer means which, on the basis of the input information, establishes the position of the focal plane of the microscope in CT coordinate space.

* * * * *